United States Patent
Ruggeri et al.

(10) Patent No.: US 6,369,075 B1
(45) Date of Patent: Apr. 9, 2002

(54) 7[4'-TRIFLUOROMETHYL-BIPHENYL-2-CARBONYL)AMINO]-QUINOLINE-3-CARBOXYLIC ACID AMIDES, AND METHOD OF INHIBITING THE SECRETION OF APOLIPOPROTEIN B

(75) Inventors: Roger Ruggeri, Waterford; Douglas Wilson, Groton, both of CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/711,281

(22) Filed: Nov. 9, 2000

Related U.S. Application Data

(60) Provisional application No. 60/224,956, filed on Aug. 11, 2000, and provisional application No. 60/164,803, filed on Nov. 10, 1999.

(51) Int. Cl.[7] ............. A61K 31/47; A61K 31/4709; C07D 215/54; C07D 401/12; C07D 401/14
(52) U.S. Cl. ............. 514/311; 514/314; 546/169; 546/170
(58) Field of Search ............. 546/169, 170; 514/311, 314

(56) References Cited

U.S. PATENT DOCUMENTS 5,919,795 A * 7/1999 Chang ............. 514/310

FOREIGN PATENT DOCUMENTS

WO     WO9726240     7/1997

* cited by examiner

Primary Examiner—Evelyn Mei Huang
(74) Attorney, Agent, or Firm—Peter C. Richardson; Gregg C. Benson; Todd M. Crissey

(57) ABSTRACT

This invention relates to compounds of Formula I

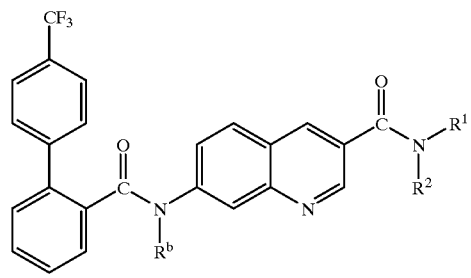

that inhibit the secretion of apolipoprotein B, to pharmaceutical compositions comprising the compounds, and to methods of treating and/or preventing atherosclerosis, obesity, diabetes, hyperlipidemia, hyperliproteinemia, hypercholesterolemia, hypertriglyceridemia, hypoalphalipoproteinemia, pancreatitis, myocardial infarction, stroke, restenosis, or Syndrome X. This invention also relates to methods of reducing the secretion of apolipoprotein B and/or inhibiting microsomal triglyceride transfer protein.

35 Claims, No Drawings

7[4'-TRIFLUOROMETHYL-BIPHENYL-2-CARBONYL)AMINO]-QUINOLINE-3-CARBOXYLIC ACID AMIDES, AND METHOD OF INHIBITING THE SECRETION OF APOLIPOPROTEIN B

CROSS REFERENCE TO RELATED APPLICATION

This application claims priority from of U.S. provisional application No. 60/164,803, filed Nov. 10, 1999 and U.S. provisional application No. 60/224,956, filed Aug. 11, 2000.

FIELD OF THE INVENTION

This invention relates to compounds that inhibit the secretion of apolipoprotein B, and to methods of treating and/or preventing atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X. This invention also relates to methods of reducing the secretion of apolipoprotein B and/or inhibiting microsomal triglyceride transfer protein.

BACKGROUND OF THE INVENTION

Microsomal triglyceride transfer protein (MTP) catalyzes the transport of triglycerides, cholesteryl esters and phospholipids, and MTP is involved in the assembly of lipoproteins that contain apolipoprotein B (apo B). Examples of lipoproteins that contain apo B include lipoprotein (a) [Lp(a)], low density lipoprotein (LDL), and very low density lipoprotein (VLDL), which is a precursor to LDL. Compounds that contain apo B are known to contribute to the formation of atherosclerotic lesions.

A noteworthy disease in which MTP plays a direct role is abetalipoproteinemia. This disease is characterized by the virtual absence of plasma lipoproteins containing apo B. For example, plasma triglyceride levels may be as low as a few mg/dl, and plasma cholesterol levels are often only 20–45 mg/dl. Interestingly, autopsies of patients having abetalipoproteinemia reveal that these patients are free of atherosclerosis. Recently, it has been discovered that this disease is caused by a defect in the MTP gene.

Compounds that inhibit MTP and/or apo B secretion are useful in the treatment and/or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, and Syndrome X. The inhibition of MTP and/or inhibition of apo B secretion typically results in the lowering of plasma concentrations of compounds that contain apo B.

In the treatment of obesity, one of the primary therapeutic goals is the suppression of caloric intake through appetite control. In order to effect practical appetite control, many therapeutic regimens have evolved such as the use of methodologies targeting certain central and peripheral biopsychological systems, including the use of periphery drugs that blunt either positive afferent information or intensify inhibitory afferent information. As such, these drugs may stimulate chemoreceptor activity in the gut or modulate gastrointestinal functioning via a network of neurotransmitters located in the enteric plexus. Other drugs may serve to mimic or perform surrogative functions for appetite-regulating factors in the blood, alter oxidative hepatic metabolism, adjust metabolic satiety signals or modify amino acid profiles. Finally, drugs may affect steroid levels reflecting energy metabolism, which, in turn, influences neuronal function, for example the corticosteroidal upregulation of adrenoreceptors in the paraventricular nucleus.

Generally, drugs affecting digestion or lipid absorption can be expected to alter the timing and pattern of nutritional information reaching the brain. Within the brain, drugs are believed to alter appetite via a number of neurotransmitter and neuromodulator systems at a variety of specific sites; however, the influence of central neurochemical activity on the expression of appetite is complex and involves numerous interactions between disparate loci and receptors resulting in shifts in the magnitude, direction and quality of feeding behavior.

While many cogent theories have been advanced based on data and direct observation, the physiology of the control of food intake is not well understood and interest in the development of safe and efficacious appetite controlling drugs remains high. See, for example, Kissilev et al., *Ann. Rev. Nutr.*, 2:371–418 (1981) and Russek, et al., *Appetite*, 2:137–143 (1981).

Conventional therapeutic approaches to the treatment of obesity have traditionally focused on the regulation of energy intake. Unfortunately, there is now a growing awareness that, while moderation of caloric intake is initially effective in reducing body weight, such regimens are not particularly effective over the long-term. In response, alternative strategies requiring less rigorous observation of caloric consumption have been developed, including the use of agents that alter the absorption of dietary fat from the gastrointestinal tract.

The gastrointestinal digestion and absorption of ingested lipids consists of several steps. Following dispersion of bulk fat into finely emulsified droplets in the stomach, fatty acid esters are hydrolyzed enzymatically, partially by the action of gastric lipase in the stomach, but predominantly by pancreatic lipase in the upper small intestine. In recent years, studies concerning certain inhibitors of pancreatic lipase, orlistat for example, have indicated that treatment with such inhibitors may hold promise in the treatment of obesity. However, in view of the complexity of the genetic component of obesity and the psychologic factors involved in maintaining lifestyle habits, the long-term efficacy of such drugs in managing body weight and decreasing obesity-related medical complications is unknown. Thus, the identification of alternative therapeutic regimens remains desirable.

The treatment of obesity is also an important therapeutic goal for the reduction of secondary disorders, including diabetes, peripheral vascular disease, hypertension, and the like. Dietary lipids represent a significant source of calories and therapeutic approaches that reduce the absorption of lipids may include, for example, reduction in the intake, digestion or absorption of lipids. In order for dietary lipids to be absorbed, they must initially be converted by hydrolysis into monoacylglycerides and free fatty acids. The inhibition of this hydrolytic cleavage of triglycerides by lipase inhibitors results in decreased absorption of monoacylglycerides and free fatty acids leading to the decreased consumption of fat with concomitant reduction or prevention of the abnormalities related thereto.

In one aspect, the present invention provides a method of treating or preventing obesity in a patient in need thereof using a compound of the present invention, or a combination of a compound of the present invention with one or more additional anti-obesity agents.

The present invention also provides a method of reducing intestinal fat absorption in a patient in need thereof using a compound of the present invention, or a combination of a compound of the present invention with one or more additional anti-obesity agents.

The present invention also provides a method for reducing food intake in a patient in need thereof using a compound of the present invention, or a combination of a compound of the present invention with one or more additional anti-obesity agents.

The glycoprotein apolipoprotein (a), [apo(a)], is synthesized and secreted by hepatic cells, and in humans, circulates largely in association with LDL in the form of a hybrid lipoprotein referred to as Lp(a). The association between apo(a) and the major protein moiety of LDL, namely apolipoprotein B100 (apo B100), is mediated through covalent linkage of a single unpaired cysteine residue in apo(a) to a complimentary unpaired cysteine residue in the extreme carboxyl terminus of apo B100.

Interest in the biology of this lipoprotein species is driven by the observation that an elevated plasma level of Lp(a) in humans is associated with an increased risk for atherosclerotic heart and vascular disease. The lowering of Lp(a) levels, however, has proven problematic since various conventional methods that are effective in reducing levels of LDL are not as efficacious or consistent in lowering levels of Lp(a). For example, it has been reported that neomycin, alone or in combination with niacin., is effective in reducing Lp(a) levels when administered over a period of several weeks to years. See Spinler, et al., *J. Ann. Pharmacother.*, 28: 343 (1994).

Alternatively, oral doses of fosinopril, an angiotensin-converting enzyme inhibitor, have been demonstrated to lower Lp(a) levels after 12 weeks of treatment; however, Lp(a) reduction was significant only in patients that showed improvement in renal function, and therefore, the Lp(a) lowering ability of fosinopril may simply be attributable to the indirect consequence of improved kidney function. See Keilani, et al., *Ann. Inter. Med.*, 118:246 (1993).

Additionally, certain steroidal hormones, estrogen for example, are known to down-regulate Lp(a) levels. See, for example, Frazer, et al., *Nature Genet.*, 9: 424 (1995). However, estrogen therapy alone is associated with an increased risk of endometrial carcinoma, and for this reason, estrogen is normally administered in combination with progesterone. Although short-term treatment with this estrogen/progesterone combination is an effective therapeutic strategy for reducing Lp(a) levels, long-term treatment, i.e. six months or more, does not result in the same degree of decreased inhibition as that observed for treatment with estrogen alone. See Soma, et al., *Arch. Internal. Med.*, 153:1462 (1993), and Soma, et al., *Chem. Phys. Lipids*, 345, 67 (1994).

Furthermore, LDL apheresis has been shown to be an effective means for lowering Lp(a) levels. See Koizumi, et al., *Atherosclerosis*, 100: 65 (1993). However, apheresis is an invasive approach requiring weekly treatments and, therefore, is not regarded as a treatment of choice. Accordingly, improved methods of reducing plasma Lp(a) levels, or formation of Lp(a) precursors will have utility in the treatment of conditions and diseases arising from hyperbetalipoproteinemia, including, for example, atherosclerosis, myocardial infarction, stroke, restenosis following coronary bypass surgery or angioplasty procedures, and so forth.

While the precise mechanisms governing blood levels of Lp(a) are presently unknown, there is evidence to suggest that Lp(a) levels are regulated at the level of synthesis rather than catabolism. Accordingly, because it is known that inhibition of hepatic secretion of VLDL and apo B results in the pre-secretory degradation of apo B and concomitant decrease in hepatic apo B levels and because each Lp(a) particle contains one copy of apo(a) bound to apo B, it is believed that decreasing the concentration of hepatic apo B, by the administration of an apo B secretion/MTP inhibitor, will result in a lowering of Lp(a) secreted, and thereby, a lowering of blood Lp(a) levels.

The treatment of diabetes and the related disease states historically involved a reduction in the amounts of ingested digestible carbohydrates by modification of dietary habits, control of nutrient entry or pharmacologically with inhibitors of carbohydrate digestive enzymes. In order for complex carbohydrates to be absorbed, they must first be metabolized into their respective monosaccharides through the action of glucosidases. The inhibition of this metabolism of complex carbohydrates by glucosidases results in decreased or delayed digestion of carbohydrates resulting in decreased absorption of glucose and in the delay or prevention of the development of diabetic complications including, for example, hyperglycemia, hyperinsulinemia, hypertriglyceridemia, and the like.

The abnormality known as "Syndrome X" is a metabolic disease characterized by insulin resistance with possible secondary abnormalities of obesity, hypertension, increased circulatory levels of triglyceride-containing VLDL's, and a reduction in HDL. cholesterol. Accordingly, the condition has been shown to be associated with an increased risk for, inter alia, hyperlipidemia, atherosclerosis and coronary artery disease. See, for example, D. N. Brindley, et al., *Progress in Obesity Research*, 7:505–510 (1996).

Some apolipoprotein B secretion inhibitors and/or MTP inhibitors are disclosed in commonly assigned U.S. Pat. No. 5,919,795 and PCT Publication WO 98/23593.

SUMMARY OF THE INVENTION

The present invention provides compounds of Formula I

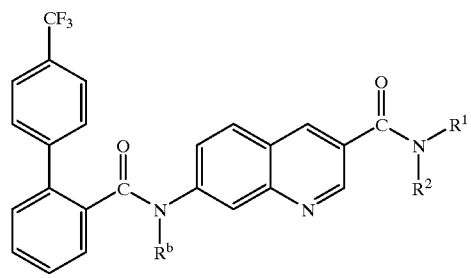

stereoisomers, pharmaceutically acceptable salts and prodrugs thereof, and pharmaceutically acceptable salts of the prodrugs,
wherein
  each $R^a$ and $R^b$ is independently hydrogen or $C_1$–$C_8$alkyl;
  each n is independently 0, 1, 2 or 3;
  each X is independently aryl, substituted aryl, heteroaryl, substituted heteroaryl, cycloalkyl, substituted cycloalkyl, heterocycloalkyl, or substitited heterocycloalkyl;
  $R^1$ is hydrogen or $C_1$–$C_8$alkyl; and
  $R^2$ is hydrogen, —$(CR^aR^a)_n$—X, $C_1$–$C_8$alkyl, $C_1$–$C_8$substituted alkyl,

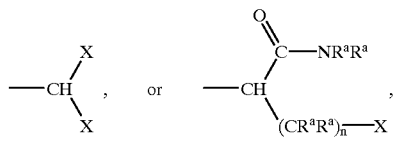

or R¹ and R² together with the nitrogen atom to which they are bonded form a 3 to 7 membered heterocycloalkyl ring comprising from 1 to 3 heteroatoms.

In a preferred embodiment of the compounds of Formula I, $R^b$ is hydrogen.

In another preferred embodiment of the compounds of Formula I, $R^b$ is hydrogen and $R^1$ is hydrogen.

In another preferred embodiment of the compounds of Formula I,
$R^b$ is hydrogen;
$R^1$ is hydrogen;
$R^2$ is

or —C(RᵃRᵃ)ₙ—X; and
each X is independently aryl or heteroaryl.

In a preferred embodiment of the compounds of Formula I, when X is aryl or heteroaryl, the aryl group is phenyl and the heteroaryl group is pyridyl.

In another preferred embodiment of the compounds of Formula I,
$R^2$ is —C(RᵃRᵃ)ₙ—X
each Rᵃ is independently methyl, ethyl or hydrogen; and
X is phenyl or pyridyl.

In another preferred embodiment of the compounds of Formula I,
$R^b$ is hydrogen;
$R^1$ is hydrogen;
$R^2$ is

and each X is independently phenyl or pyridyl.
Also provided are compounds of Formula I

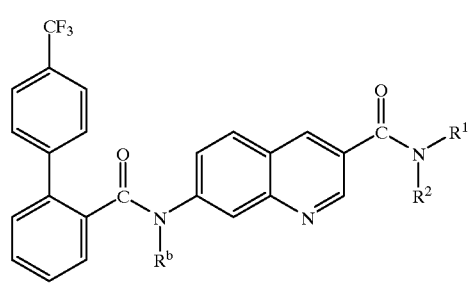

stereoisomers, pharmaceutically acceptable salts and prodrugs thereof, and pharmaceutically acceptable salts of the prodrugs, wherein $R^b$ is hydrogen;
$R^1$ is hydrogen;
$R^2$ is hydrogen, $C_1$–$C_8$alkyl, —$(CH_2)_n$—Q,

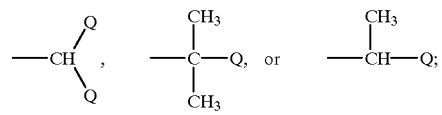

each Q is independently phenyl, pyridyl, substituted phenyl, substituted pyridyl, cycloalkyl, or heterocycloalkyl; and n is 0, 1, 2, or 3.

In a preferred embodiment of the compounds of Formula I, when Q is substituted phenyl or substituted pyridyl, the substituents are selected from —$OC_1$–$C_8$alkyl, $C_1$–$C_8$alkyl or halogen.

The present invention provides the compound:

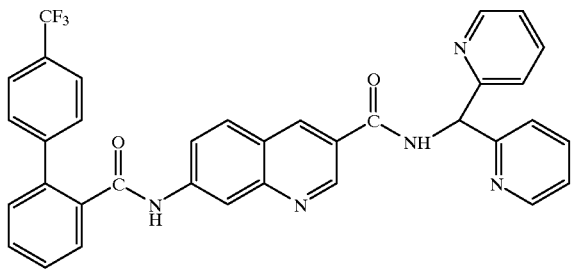

The present invention provides the compound:

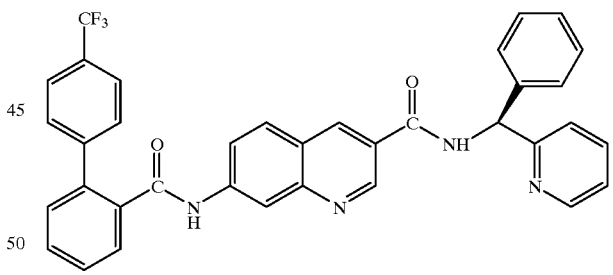

The present invention provides the compound:

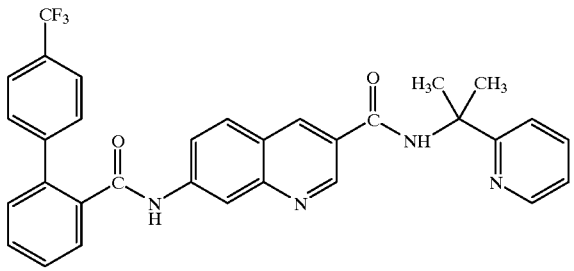

The present invention provides the compound:

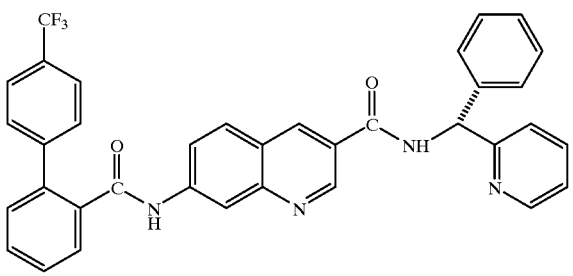

The present invention provides the compound:

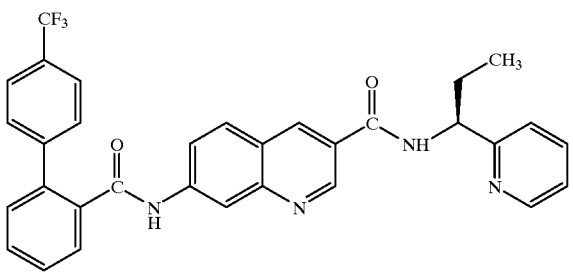

The present invention provides the compound:

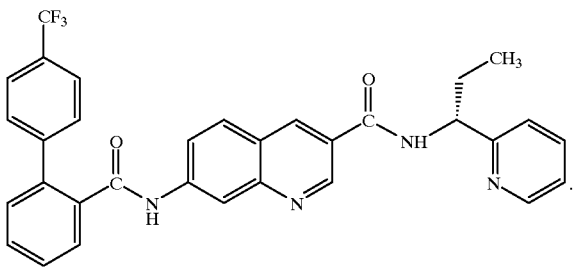

Also provided are methods of treating or preventing atherosclerosis, the methods comprising the step of administering to a patient having or at risk of having atherosclerosis a therapeutically effective amount of a compound of Formula I, stereoisomers, pharmaceutically acceptable salts and prodrugs thereof, and pharmaceutically acceptable salts of the prodrugs.

Also provided are methods of treating or preventing obesity, the methods comprising the step of administering to an obese patient or a patient at risk of becoming obese a therapeutically effective amount of a compound of Formula I, stereoisomers, pharmaceutically acceptable salts and prodrugs thereof, and pharmaceutically acceptable salts of the prodrugs.

Also provided are methods of treating or preventing hypercholesterolemia, the methods comprising the step of administering to a patient having or at risk of having hypercholesterolemia a therapeutically effective amount of a compound of Formula I, stereoisomers, pharmaceutically acceptable salts and prodrugs thereof, and pharmaceutically acceptable salts of the prodrugs.

Also provided are methods of treating or preventing hyperlipidemia, the methods comprising the step of administering to a patient having or at risk of having hyperlipidemia a therapeutically effective amount of a compound of Formula I, stereoisomers, pharmaceutically acceptable salts and prodrugs thereof, and pharmaceutically acceptable salts of the prodrugs.

Also provided are methods of treating or preventing hypertriglyceridemia, the methods comprising the step of administering to a patient having or at risk of having hypertriglyceridemia a therapeutically effective amount of a compound of Formula I, stereoisomers, pharmaceutically acceptable salts and prodrugs thereof, and pharmaceutically acceptable salts of the prodrug.

Also provided are methods of treating or preventing hypoalphalipoproteinemia, the methods comprising the step of administering to a patient having or at risk of having hypoalphalipoproteinemia a therapeutically effective amount of a compound of Formula I, stereoisomers, pharmaceutically acceptable salts and prodrugs thereof, and pharmaceutically acceptable salts of the prodrugs.

Also provided are methods of treating or preventing pancreatitis, the methods comprising the step of administering to a patient having or at risk of having pancreatitis a therapeutically effective amount of a compound of Formula I, stereoisomers, pharmaceutically acceptable salts and prodrugs thereof, and pharmaceutically acceptable salts of the prodrugs.

Also provided are methods of treating or preventing diabetes, the methods comprising the step of administering to a patient having or at risk of having diabetes a therapeutically effective amount of a compound of Formula I, stereoisomers, pharmaceutically acceptable salts and prodrugs thereof, and pharmaceutically acceptable salts of the prodrugs.

In a preferred embodiment of the method of treating diabetes, the diabetes is non-insulin dependent diabetes mellitus (Type II).

Also provided are methods of treating or preventing myocardial infarction, the methods comprising the step of administering to a patient having or at risk of having myocardial infarction a therapeutically effective amount of a compound of Formula I, stereoisomers, pharmaceutically acceptable salts and prodrugs thereof, and pharmaceutically acceptable salts of the prodrugs.

Also provided are methods method of treating or preventing a stoke, the methods comprising the step of administering to a patient having or at risk of having a stroke a therapeutically effective amount of a compound of Formula I, stereoisomers, pharmaceutically acceptable salts and prodrugs thereof, and pharmaceutically acceptable salts of the prodrugs.

Also provided are methods of treating or preventing restenosis, the methods comprising the step of administering to a patient having or at risk of having restenosis a therapeutically effective amount of a compound of Formula I, stereoisomers, pharmaceutically acceptable salts and prodrugs thereof, and pharmaceutically acceptable salts of the prodrugs.

Also provided are methods of treating or preventing Syndrome X, the methods comprising the step of administering to a patient having or at risk of having Syndrome X a therapeutically effective amount of a compound of Formula I, stereoisomers, pharmaceutically acceptable salts and prodrugs thereof, and pharmaceutically acceptable salts of the prodrugs.

Also provided are methods of inhibiting apolipoprotein B secretion, the methods comprising administering to a patient in need of apolipoprotein B secretion inhibition an apolipoprotein B secretion inhibiting amount of a compound of Formula I, stereoisomers, pharmaceutically acceptable salts and prodrugs thereof, and pharmaceutically acceptable salts of the prodrugs.

Also provided are methods of inhibiting microsomal triglyceride transfer protein, the methods comprising administering to a patient in need of microsomal triglyceride transfer protein inhibition a microsomal triglyceride transfer protein inhibiting amount of a compound of Formula I, stereoisomers, pharmaceutically acceptable salts and prodrugs thereof, and pharmaceutically acceptable salts of the prodrugs.

Also provided are pharmaceutical composition comprising a compound of Formula I, stereoisomers, pharmaceutically acceptable salts and prodrugs thereof, and pharmaceutically acceptable salts of the prodrugs.

The present invention provides the compounds:
7-amino-quinoline-3-carboxylic acid ethyl ester;
7-[(4'-trifluoromethyl-biphenyl-2-carbonyl)-amino]-quinoline-3-carboxylic acid ethyl ester;
7-[(4'-trifluoromethyl-biphenyl-2-carbonyl)-amino]-quinoline-3-carboxylic acid;
7-[(4'-trifluoromethyl-biphenyl-2-carbonyl)-amino]-quinoline-3-carboxylic acid (dipyridin-2-yl-methyl)-amide;
7-[(4'-trifluoromethyl-biphenyl-2-carbonyl)-amino]-quinoline-3-carboxylic acid (dipyridin-2-yl-methyl)-amide, ethanesulfonate;
7-[(4'-trifluoromethyl-biphenyl-2-carbonyl)-amino]-quinoline-3-carboxylic acid (dipyridin-2-yl-methyl)-amide, bis-ethanesulfonate;
7-[(4'-trifluoromethyl-biphenyl-2-carbonyl)-amino]-quinoline-3-carboxylic acid (phenyl-pyridin-2-yl-methyl)-amide;
7-[(4'-trifluoromethyl-biphenyl-2-carbonyl)-amino]-quinoline-3-carboxylic acid (phenyl-pyridin-2-yl-methyl)-amide, ethanesulfonate;
(S)-7-[(4'-trifluoromethyl-biphenyl-2-carbonyl)-amino]-quinoline-3-carboxylic acid (phenyl-pyridin-2-yl-methyl)-amide;
(S)-7-[(4'-trifluoromethyl-biphenyl-2-carbonyl)-amino]-quinoline-3-carboxylic acid (phenyl-pyridin-2-yl-methyl)-amide, ethanesulfonate;
(S)-7-[(4'-trifluoromethyl-biphenyl-2-carbonyl)-amino]-quinoline-3-carboxylic acid (phenyl-pyridin-2-yl-methyl)-amide, bis-ethanesulfonate;
(R)-7-[(4'-trifluoromethyl-biphenyl-2-carbonyl)-amino]-quinoline-3-carboxylic acid (phenyl-pyridin-2-yl-methyl)-amide;
(R)-7-[(4'-trifluoromethyl-biphenyl-2-carbonyl)-amino]-quinoline-3-carboxylic acid (phenyl-pyridin-2-yl-methyl)-amide, ethanesulfonate;
7-[(4'-trifluoromethyl-biphenyl-2-carbonyl)-amino]-quinoline-3-carboxylic acid (phenyl-pyridin-2-yl-methyl)-amide, bis-ethanesulfonate;
7-[(4'-trifluoromethyl-biphenyl-2-carbonyl)-amino]-quinoline-3-carboxylic acid (1-carbamoyl-2-phenyl-ethyl)-amide;
7-[(4'-trifluoromethyl-biphenyl-2-carbonyl)-amino]-quinoline-3-carboxylic acid (carbamoyl-phenyl-methyl)-amide;
7-[(4'-trifluoromethyl-biphenyl-2-carbonyl)-amino]-quinoline-3-carboxylic acid propylamide;
7-[(4'-trifluoromethyl-biphenyl-2-carbonyl)-amino]-quinoline-3-carboxylic acid (2,2,2-trifluoro-ethyl)-amide;
7-[(4'-trifluoromethyl-biphenyl-2-carbonyl)-amino]-quinoline-3-carboxylic acid (1-methyl-1-phenyl-ethyl)-amide;
7-[(4'-trifluoromethyl-biphenyl-2-carbonyl)-amino]-quinoline-3-carboxylic acid cyclopentylamide;
7-[(4'-trifluoromethyl-biphenyl-2-carbonyl)-amino]-quinoline-3-carboxylic acid (1-phenyl-propyl)-amide;
(R)-7-[(4'-trifluoromethyl-biphenyl-2-carbonyl)-amino]-quinoline-3-carboxylic acid (1-phenyl-ethyl)-amide, ethanesulfonate;
7-[(4'-trifluoromethyl-biphenyl-2-carbonyl)-amino]-quinoline-3-carboxylic acid (1-phenyl-ethyl)-amide, ethanesulfonate;
7-[(4'-trifluoromethyl-biphenyl-2-carbonyl)-amino]-quinoline-3-carboxylic acid (1-pyridin-2-yl-propyl)-amide;
(R)-7-[(4'-trifluoromethyl-biphenyl-2-carbonyl)-amino]-quinoline-3-carboxylic acid (1-pyridin-2-yl-propyl)-amide;
(R)-7-[(4'-trifluoromethyl-biphenyl-2-carbonyl)-amino]-quinoline-3carboxylic acid (1-pyridin-2-yl-propyl)-amide, ethanesulfonate;
(S)-7-[(4'-trifluoromethyl-biphenyl-2-carbonyl)-amino]-quinoline-3-carboxylic acid (1-pyridin-2-yl-propyl)-amide;
(S)-7-[(4'-trifluoromethyl-biphenyl-2-carbonyl)-amino]-quinoline-3-carboxylic acid (1-pyridin-2-yl-propyl)-amide ethanesulfonate;
7-[(4'-trifluoromethyl-biphenyl-2-carbonyl)-amino]-quinoline-3-carboxylic acid (1-pyridin-2-yl-propyl)-amide, ethanesulfonate;
7-[(4'-trifluoromethyl-biphenyl-2-carbonyl)-amino]-quinoline-3-carboxylic acid (pyridin-2-ylmethyl)-amide, ethanesulfonate;
7-[(4'-trifluoromethyl-biphenyl-2-carbonyl)-amino]-quinoline-3-carboxylic acid (2-pyridin-2-yl-ethyl)-amide, ethanesulfonate;
7-[(4'-trifluoromethyl-biphenyl-2-carbonyl)-amino]-quinoline-3-carboxylic acid ethylamide, ethanesulfonate;
7-[(4'-trifluoromethyl-biphenyl-2-carbonyl)-amino]-quinoline-3-carboxylic acid butylamide, ethanesulfonate;
7-[(4'-trifluoromethyl-biphenyl-2-carbonyl)-amino]-quinoline-3-carboxylic acid (thiophen-2-ylmethyl)-amide, ethanesulfonate;
7-[(4'-trifluoromethyl-biphenyl-2-carbonyl)-amino]-quinoline-3-carboxylic acid (1-methyl-1-pyridin-2-yl-ethyl)-amide;
(S)-7-[(4'-trifluoromethyl-biphenyl-2-carbonyl)-amino]-quinoline-3-carboxylic acid (1-pyridin-2-yl-ethyl)-amide;
(R)-7-[(4'-trifluoromethyl-biphenyl-2-carbonyl)-amino]-quinoline-3-carboxylic acid (1-pyridin-2-yl-ethyl)-amide ethanesulfonate;
7-[(4'-trifluoromethyl-biphenyl-2-carbonyl)-amino]-quinoline-3-carboxylic acid (1-pyridin-2-yl-ethyl)-amide;
7-[(4'-trifluoromethyl-biphenyl-2-carbonyl)-amino]-quinoline-3-carboxylic acid (1-pyridin-2-yl-ethyl)-amide ethanesulfonate;
7-[(4'-trifluoromethyl-biphenyl-2-carbonyl)-amino]-quinoline-3-carboxylic acid amide;
7-[(4'-trifluoromethyl-biphenyl-2-carbonyl)-amino]-quinoline-3-carboxylic acid benzylamide;
7-[(4'-trifluoromethyl-biphenyl-2-carbonyl)-amino]-quinoline-3-carboxylic acid 4-methoxy-benzylamide;
7-[(4'-trifluoromethyl-biphenyl-2-carbonyl)-amino]-quinoline-3-carboxylic acid 4-chloro-benzylamide;
7-[(4'-trifluoromethyl-biphenyl-2-carbonyl)-amino]-quinoline-3-carboxylic acid 4-methyl-benzylamide;
7-[(4'-trifluoromethyl-biphenyl-2-carbonyl)-amino]-quinoline-3-carboxylic acid cyclopropylmethyl-amide;
7-[(4'-trifluoromethyl-biphenyl-2-carbonyl)-amino]-quinoline-3-carboxylic acid 4-fluoro-benzylamide;
7-[(4'-trifluoromethyl-biphenyl-2-carbonyl)-amino]-quinoline-3-carboxylic acid isopropyl-amide;
7-[(4'-trifluoromethyl-biphenyl-2-carbonyl)-amino]-quinoline-3-carboxylic acid benzhydryl-amide;

7-[(4'-trifluoromethyl-biphenyl-2-carbonyl)-amino]-quinoline-3-carboxylic acid cyclopropylamide;
7-[(4'-trifluoromethyl-biphenyl-2-carbonyl)-amino]-quinoline-3-carboxylic acid [1-(4-fluoro-phenyl)-ethyl]-amide;
7-[(4'-trifluoromethyl-biphenyl-2-carbonyl)-amino]-quinoline-3-carboxylic acid 3-methyl-benzylamide;
7-[(4'-trifluoromethyl-biphenyl-2-carbonyl)-amino]-quinoline-3-carboxylic acid 3-methoxy-benzylamide;
7-[(4'-trifluoromethyl-biphenyl-2-carbonyl)-amino]-quinoline-3-carboxylic acid 3-chloro-benzylamide;
7-[(4'-trifluoromethyl-biphenyl-2-carbonyl)-amino]-quinoline-3-carboxylic acid 2-fluoro-benzylamide;
7-[(4'-trifluoromethyl-biphenyl-2-carbonyl)-amino]-quinoline-3-carboxylic acid 3-fluoro-benzylamide;
7-[(4'-trifluoromethyl-biphenyl-2-carbonyl)-amino]-quinoline-3-carboxylic acid 2-methyl-benzylamide;
7-[(4'-trifluoromethyl-biphenyl-2-carbonyl)-amino]-quinoline-3-carboxylic acid 2-methoxy-benzylamide;
7-[(4'-trifluoromethyl-biphenyl-2-carbonyl)-amino]-quinoline-3-carboxylic acid 2-chloro-benzylamide;
4'-trifluoromethyl-biphenyl-2-carboxylic acid [3-(pyrrolidine-1-carbonyl)-quinolin-7-yl]-amide;
4'-trifluoromethyl-biphenyl-2-carboxylic acid [3-(morpholine-4-carbonyl)-quinolin-7-yl]-amide;
7-[(4'-trifluoromethyl-biphenyl-2-carbonyl)-amino]-quinoline-3-carboxylic acid diethylamide; and
4'-trifluoromethyl-biphenyl-2-carboxylic acid [3-(piperidine-1-carbonyl)-quinolin-7-yl]-amide, stereoisomers, pharmaceutically acceptable salts and prodrugs thereof, and pharmaceutically acceptable salts of the prodrugs.

Also provided are kits for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, and Syndrome X, the kits comprising:
a) a first pharmaceutical composition comprising a compound of Formula I, stereoisomers, pharmaceutically acceptable salts and prodrugs thereof, and pharmaceutically acceptable salts of the prodrugs.
b) a second pharmaceutical composition comprising a second compound useful for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X; and
c) a container for containing the first and second compositions.

Also provided are methods for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X, the methods comprising the step of administering to a patient having or at risk of having atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X a therapeutically effective amount of a compound of Formula I, stereoisomers, pharmaceutically acceptable salts and prodrugs thereof, and pharmaceutically acceptable salts of the prodrugs in combination with at least one additional compound useful for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X.

In a preferred embodiment of the method, the additional compound is a HMG-CoA reductase inhibitor.

In another preferred embodiment of the method, the additional compound is a MTP inhibitor.

In another preferred embodiment of the method, the additional compound is a HMG-CoA synthase inhibitor.

In another preferred embodiment of the method, the additional compound is an ACAT inhibitor.

In another preferred embodiment of the method, the additional compound is a CETP inhibitor.

In another preferred embodiment of the method, the additional compound is a lipase inhibitor.

In another preferred embodiment of the method, the additional compound is a glucosidase inhibitor.

Also provided are pharmaceutical compositions comprising a compound of Formula I, stereoisomers, pharmaceutically acceptable salts and prodrugs thereof, and pharmaceutically acceptable salts of the prodrug, and at least one additional compound useful for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X.

In a preferred composition, the additional compound is a HMG-CoA reductase inhibitor.

In another preferred composition, the additional compound is a MTP inhibitor.

In a preferred composition the additional compound is a HMG-CoA synthase inhibitor.

In another preferred composition, the additional compound is an ACAT inhibitor.

In another preferred composition, the additional compound is a CETP inhibitor.

In another preferred composition, the additional compound is a lipase inhibitor.

In another preferred composition, the additional compound is a glucosidase inhibitor.

The present invention also provides compounds of Formula II

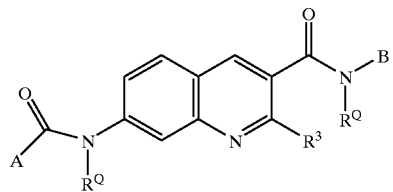

II stereoisomers, pharmaceutically acceptable salts and prodrugs thereof, and pharmaceutically acceptable salts of the prodrugs,
wherein
each $R^3$ is independently hydrogen or $C_1$–$C_6$alkyl;
each $R^Q$ is independently hydrogen or $C_1$–$C_6$alkyl;

A is

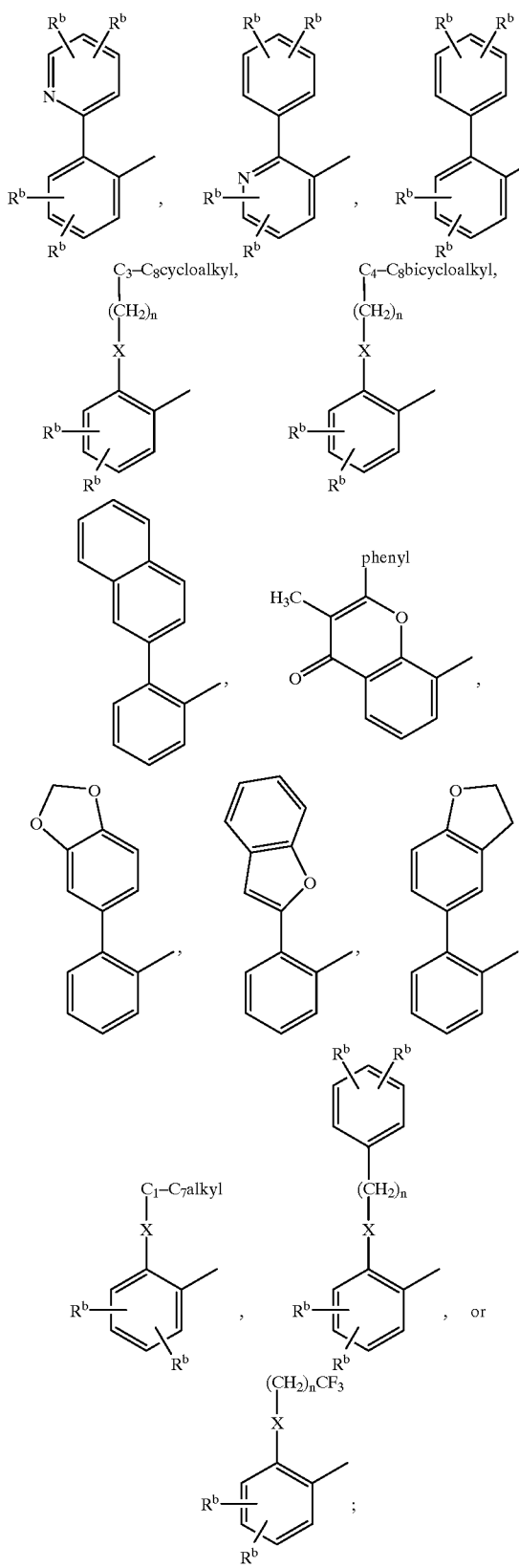

X is O or S;
n is 0 to 6;

each $R^b$ is independently hydrogen, $-CF_3$, $-OC_1-C_6alkyl$, halo, $-SH$, $-SC_1-C_6alkyl$, phenyl, or $-C_1-C_6alkyl$;

B is hydrogen,

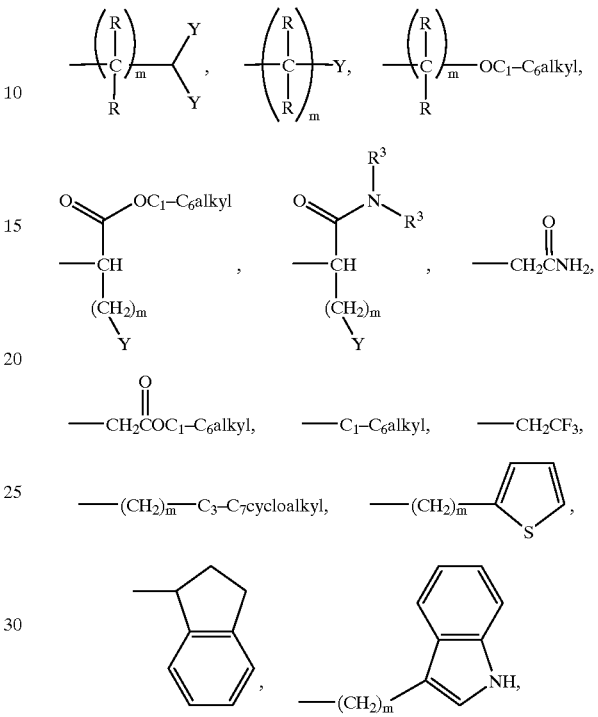

or B and $R^Q$ together with the nitrogen atom to which they are bonded form a heterocycloalkyl ring comprising from 1 to 3 heteroatoms;

each R is independently hydrogen or $C_1-C_6alkyl$;

each Y is independently phenyl, substituted phenyl, pyridyl or substituted pyridyl, wherein any substituents are independently selected from $-CF_3$, halo, $-OC_1-C_6alkyl$, or $-C_1-C_6alkyl$; and m is 0 to 5.

In a preferred embodiment of the compounds of Formula II, A is

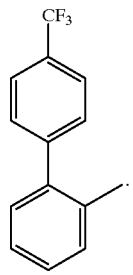

In another preferred embodiment of the compounds of Formula II, each $R^Q$ is hydrogen.

In another preferred embodiment of the compounds of Formula II, $R^3$ is hydrogen.

In another preferred embodiment of the compounds of Formula II, B is

and each Y is independently phenyl or pyridyl.

Also provided by the present invention are the compounds:
7-[(4'-trifluoromethyl-biphenyl-2-carbonyl)-amino]-quinoline-3-carboxylic acid [bis-(4-fluoro-phenyl)-methyl]-amide;
7-[(4'-trifluoromethyl-biphenyl-2-carbonyl)-amino]-quinoline-3-carboxylic acid benzyl-ethyl-amide;
7-[(4'-trifluoromethyl-biphenyl-2-carbonyl)-amino]-quinoline-3-carboxylic acid (3-phenyl-propyl)-amide;
7-[(4'-trifluoromethyl-biphenyl-2-carbonyl)-amino]-quinoline-3-carboxylic acid ethyl-pyridin-2-ylmethyl-amide;
7-[(4'-trifluoromethyl-biphenyl-2-carbonyl)-amino]-quinoline-3-carboxylic acid phenethyl-amide;
7-[(4'-trifluoromethyl-biphenyl-2-carbonyl)-amino]-quinoline-3-carboxylic acid phenylamide;
7-[(4'-trifluoromethyl-biphenyl-2-carbonyl)-amino]-quinoline-3-carboxylic acid (2-methoxy-ethyl)-amide;
7-[(4'-trifluoromethyl-biphenyl-2-carbonyl)-amino]-quinoline-3-carboxylic acid (1-methyl-3-phenyl-propyl)-amide;
7-[(4'-trifluoromethyl-biphenyl-2-carbonyl)-amino]-quinoline-3-carboxylic acid indan-1-ylamide;
7-[(4'-trifluoromethyl-biphenyl-2-carbonyl)-amino]-quinoline-3-carboxylic acid (3,3-diphenyl-propyl)-amide;
7-[(4'-trifluoromethyl-biphenyl-2-carbonyl)-amino]-quinoline-3-carboxylic acid [2-(1H-indol-3-yl)-ethyl]-amide;
7-[(4'-trifluoromethyl-biphenyl-2-carbonyl)-amino]-quinoline-3-carboxylic acid (4-phenyl-butyl)-amide;
[R]-7-[(4'-trifluoromethyl-biphenyl-2-carbonyl)-amino]-quinoline-3-carboxylic acid [(4-fluoro-phenyl)-pyridin-2-yl-methyl]-amide;
[S]-7-[(4'-trifluoromethyl-biphenyl-2-carbonyl)-amino]-quinoline-3-carboxylic acid [(4-fluoro-phenyl)-pyridin-2-yl-methyl]-amide;
2-methyl-7-[(4'-trifluoromethyl-biphenyl-2-carbonyl)-amino]-quinoline-3-carboxylic acid (2-methoxy-ethyl)-amide;
[S]-2-methyl-7-[(4'-trifluoromethyl-biphenyl-2-carbonyl)-amino]-quinoline-3-carboxylic acid (phenyl-pyridin-2-yl-methyl)-amide;
[R]-7-[2-(5-trifluoromethyl-pyridin-2-yl)-benzoylamino]-quinoline-3-carboxylic acid (1-pyridin-2-yl-propyl)-amide;
[R]-7-[2-(5-trifluoromethyl-pyridin-2-yl)-benzoylamino]-quinoline-3-carboxylic acid (1-pyridin-2-yl-ethyl)-amide;
[S]-7-[2-(5-trifluoromethyl-pyridin-2-yl)-benzoylamino]-quinoline-3-carboxylic acid (phenyl-pyridin-2-yl-methyl)-amide;
[R]-7-[2-(6-methyl-pyridin-3-yl)-benzoylamino]-quinoline-3-carboxylic acid (1-pyridin-2-yl-ethyl)-amide;
[R]-7-[2-(5-methyl-pyridin-2-yl)-benzoylamino]-quinoline-3-carboxylic acid (1-pyridin-2-yl-ethyl)-amide;
[S]-7-{[2-(4-trifluoromethyl-phenyl)-pyridine-3-carbonyl]-amino}-quinoline-3-carboxylic acid (phenyl-pyridin-2-yl-methyl)-amide;
[R]-7-{[2-(4-trifluoromethyl-phenyl)-pyridine-3-carbonyl]-amino}-quinoline-3-carboxylic acid (1-pyridin-2-yl-ethyl)-amide;
[R]-7-{[2-(4-trifluoromethyl-phenyl)-pyridine-3-carbonyl]-amino}-quinoline-3-carboxylic acid (1-pyridin-2-yl-propyl)-amide;
[R]-7-[(2-p-tolyl-pyridine-3-carbonyl)-amino]-quinoline-3-carboxylic acid (1-pyridin-2-yl-ethyl)-amide;
[R]-7-{[2-(4-isopropyl-phenyl)-pyridine-3-carbonyl]-amino}-quinoline-3-carboxylic acid (1-pyridin-2-yl-ethyl)-amide;
[R]-7-{[2-(4-tert-butyl-phenyl)-pyridine-3-carbonyl]-amino}-quinoline-3-carboxylic acid (1-pyridin-2-yl-ethyl)-amide;
[R]-7-{[2-(4-methoxy-phenyl)-pyridine-3-carbonyl]-amino}-quinoline-3-carboxylic acid (1-pyridin-2-yl-ethyl)-amide;
[R]-7-{[2-(4-ethyl-phenyl)-pyridine-3-carbonyl]-amino}-quinoline-3-carboxylic acid (1-pyridin-2-yl-ethyl)-amide;
7-[(4'-tert-butyl-biphenyl-2-carbonyl)-amino]-quinoline-3-carboxylic acid (phenyl-pyridin-2-yl-methyl)-amide;
7-[(biphenyl-2-carbonyl)-amino]-quinoline-3-carboxylic acid (phenyl-pyridin-2-yl-methyl)-amide;
7-[(biphenyl-2-carbonyl)-amino]-quinoline-3-carboxylic acid (1-pyridin-2-yl-propyl)-amide;
7-[(biphenyl-2-carbonyl)-amino]-quinoline-3-carboxylic acid (di-pyridin-2-yl-methyl)-amide;
7-[(4'-methyl-biphenyl-2-carbonyl)-amino]-quinoline-3-carboxylic acid (phenyl-pyridin-2-yl-methyl)-amide;
7-[(4'-methyl-biphenyl-2-carbonyl)-amino]-quinoline-3-carboxylic acid acid (di-pyridin-2-yl-methyl)-amide;
7-[(4'-methyl-biphenyl-2-carbonyl)-amino]-quinoline-3-carboxylic acid acid (1-pyridin-2-yl-propyl)-amide;
7-(2-benzofuran-2-yl-benzoylamino)-quinoline-3-carboxylic acid (phenyl-pyridin-2-yl-methyl)-amide;
7-[(4'-isopropyl-biphenyl-2-carbonyl)-amino]-quinoline-3-carboxylic acid (di-pyridin-2-yl-methyl)-amide;
7-[(4'-isopropyl-biphenyl-2-carbonyl)-amino]-quinoline-3-carboxylic acid acid (phenyl-pyridin-2-yl-methyl)-amide;
7-[(4'-isopropyl-biphenyl-2-carbonyl)-amino]-quinoline-3-carboxylic acid (1-pyridin-2-yl-propyl)-amide;
7-[(3'-methyl-biphenyl-2-carbonyl)-amino]-quinoline-3-carboxylic acid (phenyl-pyridin-2-yl-methyl)-amide;
7-[(4'-ethyl-biphenyl-2-carbonyl)-amino]-quinoline-3-carboxylic acid (phenyl-pyridin-2-yl-methyl)-amide;
7-[(4'-ethyl-biphenyl-2-carbonyl)-amino]-quinoline-3-carboxylic acid (1-pyridin-2-yl-propyl)-amide;
7-[(4'-tert-butyl-biphenyl-2-carbonyl)-amino]-quinoline-3-carboxylic acid (1-pyridin-2-yl-propyl)-amide;
7-[(4'-ethylsulfanyl-biphenyl-2-carbonyl)-amino]-quinoline-3-carboxylic acid (phenyl-pyridin-2-yl-methyl)-amide;
7-[(4'-ethylsulfanyl-biphenyl-2-carbonyl)-amino]-quinoline-3-carboxylic acid (1-pyridin-2-yl-propyl)-amide;
7-(2-naphthalen-2-yl-benzoylamino)-quinoline-3-carboxylic acid (phenyl-pyridin-2-yl-methyl)-amide;
7-(2-benzo[1,3]dioxol-5-yl-benzoylamino)-quinoline-3-carboxylic acid (phenyl-pyridin-2-yl-methyl)-amide;
7-[(3',4'-dimethyl-biphenyl-2-carbonyl)-amino]-quinoline-3-carboxylic acid (phenyl-pyridin-2-yl-methyl)-amide;
7-[(2'-methyl-biphenyl-2-carbonyl)-amino]-quinoline-3-carboxylic acid (phenyl-pyridin-2-yl-methyl)-amide;
7-[(3'-fluoro-4'-methyl-biphenyl-2-carbonyl)-amino]-quinoline-3-carboxylic acid (phenyl-pyridin-2-yl-methyl)-amide;
7-[(4'-ethoxy-biphenyl-2-carbonyl)-amino]-quinoline-3-carboxylic acid (phenyl-pyridin-2-yl-methyl)-amide;
7-[(4'-ethoxy-biphenyl-2-carbonyl)-amino]-quinoline-3-carboxylic acid (1-pyridin-2-yl-propyl)-amide;

7-[(4'-ethoxy-biphenyl-2-carbonyl)-amino]-quinoline-3-carboxylic acid (di-pyridin-2-yl-methyl)-amide;
7-[2-(2,3-dihydro-benzofuran-5-yl)-benzoylamino]-quinoline-3-carboxylic acid (phenyl-pyridin-2-yl-methyl)-amide;
7-[(4'-propoxy-biphenyl-2-carbonyl)-amino]-quinoline-3-carboxylic acid (phenyl-pyridin-2-yl-methyl)-amide;
7-[(4'-propoxy-biphenyl-2-carbonyl)-amino]-quinoline-3-carboxylic acid (1-pyridin-2-yl-propyl)-amide;
7-[(4'-butoxy-biphenyl-2-carbonyl)-amino]-quinoline-3-carboxylic acid (phenyl-pyridin-2-yl-methyl)-amide;
7-[(4'-butoxy-biphenyl-2-carbonyl)-amino]-quinoline-3-carboxylic acid (1-pyridin-2-yl-propyl)-amide;
7-[(3-methyl-4-oxo-2-phenyl-4H-chromene-8-carbonyl)-amino]-quinoline-3-carboxylic acid (1-pyridin-2-yl-propyl)-amide;
7-[(3-methyl-4-oxo-2-phenyl-4H-chromene-8-carbonyl)-amino]-quinoline-3-carboxylic acid (phenyl-pyridin-2-yl-methyl)-amide;
7-[(3-methyl-4-oxo-2-phenyl-4H-chromene-8-carbonyl)-amino]-quinoline-3-carboxylic acid (di-pyridin-2-yl-methyl)-amide;
7-(2-cyclohexylmethoxy-benzoylamino)-quinoline-3-carboxylic acid (di-pyridin-2-yl-methyl)-amide;
7-(2-cyclohexylmethoxy-benzoylamino)-quinoline-3-carboxylic acid (phenyl-pyridin-2-yl-methyl)-amide;
7-(2-cyclohexylmethoxy-benzoylamino)-quinoline-3-carboxylic acid (1-pyridin-2-yl-propyl)-amide;
7-(2-cyclohexylmethoxy-3-methoxy-benzoylamino)-quinoline-3-carboxylic acid (phenyl-pyridin-2-yl-methyl)-amide;
7-(2-cyclohexylmethoxy-3-methoxy-benzoylamino)-quinoline-3-carboxylic acid (di-pyridin-2-yl-methyl)-amide;
7-(2-cyclohexylmethoxy-3-methoxy-benzoylamino)-quinoline-3-carboxylic acid (1-pyridin-2-yl-propyl)-amide;
7-[2-(bicyclo[2.2.1]hept-2-ylmethoxy)-benzoylamino]-quinoline-3-carboxylic acid (di-pyridin-2-yl-methyl)-amide;
7-[2-(bicyclo[2.2.1]hept-2-ylmethoxy)-benzoylamino]-quinoline-3-carboxylic acid (phenyl-pyridin-2-yl-methyl)-amide;
7-[2-(bicyclo[2.2.1]hept-2-ylmethoxy)-benzoylamino]-quinoline-3-carboxylic acid (1-pyridin-2-yl-propyl)-amide;
7-[2-(bicyclo[2.2.1]hept-2-ylmethoxy)-3-methoxy-benzoylamino]-quinoline-3-carboxylic acid (di-pyridin-2-yl-methyl)-amide;
7-[2-(bicyclo[2.2.1]hept-2-ylmethoxy)-3-methoxy-benzoylamino]-quinoline-3-carboxylic acid (phenyl-pyridin-2-yl-methyl)-amide;
-[2-(bicyclo[2.2.1]hept-2-ylmethoxy)-3-methoxy-benzoylamino]-quinoline-3-carboxylic acid (1-pyridin-2-yl-propyl)-amide;
-(2-pentyloxy-benzoylamino)-quinoline-3-carboxylic acid (di-pyridin-2-yl-methyl)-amide;
7-(2-pentyloxy-benzoylamino)-quinoline-3-carboxylic (phenyl-pyridin-2-yl-methyl)-amide;
7-(2-pentyloxy-benzoylamino)-quinoline-3-carboxylic acid (1-pyridin-2-yl-propyl)-amide;
7-(3-methoxy-2-pentyloxy-benzoylamino)-quinoline-3-carboxylic acid (di-pyridin-2-yl-methyl)-amide;
7-(3-methoxy-2-pentyloxy-benzoylamino)-quinoline-3-carboxylic acid (phenyl-pyridin-2-yl-methyl)-amide;
7-(3-methoxy-2-pentyloxy-benzoylamino)-quinoline-3-carboxylic acid (1-pyridin-2-yl-propyl)-amide;
7-(2-benzyloxy-3-methoxy-benzoylamino)-quinoline-3-carboxylic acid (di-pyridin-2-yl-methyl)-amide;
7-(2-cyclopentylethoxy-3-methoxy-benzoylamino)-quinoline-3-carboxylic acid (di-pyridin-2-yl-methyl)-amide;
7-[3-methoxy-2-(4,4,4-trifluoro-butoxy)-benzoylamino]-quinoline-3-carboxylic acid (di-pyridin-2-yl-methyl)-amide;
-7-[3-methoxy-2-(3-methyl-butoxy)-benzoylamino]-quinoline-3-carboxylic acid (di-pyridin-2-yl-methyl)-amide;
7-(2-cyclobutylmethoxy-3-methoxy-benzoylamino)-quinoline-3-carboxylic acid (di-pyridin-2-yl-methyl)-amide;
7-(2-cyclopentylmethoxy-3-methoxy-benzoylamino)-quinoline-3-carboxylic acid (di-pyridin-2-yl-methyl)-amide;
2-hexyloxy-3-methoxy-benzoylamino)-quinoline-3-carboxylic acid (di-pyridin-2-yl-methyl)-amide;
7-(2-cyclohexylethoxy-3-methyl-benzoylamino)-quinoline-3-carboxylic acid (di-pyridin-2-yl-methyl)-amide;
7-(2-cyclohexylmethoxy-3-methyl-benzoylamino)-quinoline-3-carboxylic acid (di-pyridin-2-yl-methyl)-amide;
2-methyl-7-[2-(5-trifluoromethyl-pyridin-2-yl)-benzoylamino]-quinoline-3-carboxylic acid (1-pyridin-2-yl-ethyl)-amide;
2-methyl-7-{[2-(4-trifluoromethyl-phenyl)-pyridine-3-carbonyl]-amino}-quinoline-3-carboxylic acid (1-pyridin-2-yl-ethyl)-amide;
2-ethyl-7-[2-(5-trifluoromethyl-pyridin-2-yl)-benzoylamino]-quinoline-3-carboxylic acid (1-pyridin-2-yl-ethyl)-amide;
2-ethyl-7-{[2-(4-trifluoromethyl-phenyl)-pyridine-3-carbonyl]-amino}-quinoline-3-carboxylic acid (1-pyridin-2-yl-ethyl)-amide;
7-{[6-methyl-2-(4-trifluoromethyl-phenyl)-pyridine-3-carbonyl]-amino}-quinoline-3-carboxylic acid (1-pyridin-2-yl-ethyl)-amide;
7-[(6-methyl-4'-trifluoromethyl-biphenyl-2-carbonyl)-amino]-quinoline-3-carboxylic acid (1-pyridin-2-yl-ethyl)-amide;
7-[3-methyl-2-(5-trifluoromethyl-pyridin-2-yl)-benzoylamino]-quinoline-3-carboxylic acid (1-pyridin-2-yl-ethyl)-amide;
7-[3,5-dimethyl-2-(5-trifluoromethyl-pyridin-2-yl)-benzoylamino]-quinoline-3-carboxylic acid (1-pyridin-2-yl-ethyl)-amide; or
7-(3-chloro-2-cyclohexylmethoxy-benzoylamino)-quinoline-3-carboxylic acid (di-pyridin-2-yl-methyl)-amide, stereoisomers, pharmaceutically acceptable salts and prodrugs thereof, and pharmaceutically acceptable salts of the prodrugs.

Also provided are methods of treating or preventing atherosclerosis, the methods comprising the step of administering to a patient having or at risk of having atherosclerosis a therapeutically effective amount of a compound of Formula II, or a stereoisomer, pharmaceutically acceptable salt or prodrug thereof, or a pharmaceutically acceptable salt of the prodrug.

Also provided are methods of treating or preventing obesity, the methods comprising the step of administering to an obese patient or a patient at risk of becoming obese a therapeutically effective amount of a compound of Formula II, or a stereoisomer, pharmaceutically acceptable salt or prodrug thereof, or a pharmaceutically acceptable salt of the prodrug.

Also provided are methods of treating or preventing hypercholesterolemia, the methods comprising the step of administering to a patient having or at risk of having hypercholesterolemia a therapeutically effective amount of a compound of Formula II, or a stereoisomer, pharmaceutically acceptable salt or prodrug thereof, or a pharmaceutically acceptable salt of the prodrug.

Also provided are methods of treating or preventing hyperlipidemia, the methods comprising the step of administering to a patient having or at risk of having hyperlipidemia a therapeutically effective amount of a compound of Formula II, or a stereoisomer, pharmaceutically acceptable salt or prodrug thereof, or a pharmaceutically acceptable salt of the prodrug.

Also provided are methods of treating or preventing hypertriglyceridemia, the methods comprising the step of administering to a patient having or at risk of having hypertriglyceridemia a therapeutically effective amount of a compound of Formula II, or a stereoisomer, pharmaceutically acceptable salt or prodrug thereof, or a pharmaceutically acceptable salt of the prodrug.

Also provided are methods of treating or preventing hypoalphalipoproteinemia, the methods comprising the step of administering to a patient having or at risk of having hypoalphalipoproteinemia a therapeutically effective amount of a compound of Formula II, or a stereoisomer, pharmaceutically acceptable salt or prodrug thereof, or a pharmaceutically acceptable salt of the prodrug.

Also provided are methods of treating or preventing pancreatitis, the methods comprising the step of administering to a patient having or at risk of having pancreatitis a therapeutically effective amount of a compound of Formula II, or a stereoisomer, pharmaceutically acceptable salt or prodrug thereof, or a pharmaceutically acceptable salt of the prodrug.

Also provided are methods of treating or preventing diabetes, the methods comprising the step of administering to a patient having or at risk of having diabetes a therapeutically effective amount of a compound of Formula II, or a stereoisomer, pharmaceutically acceptable salt or prodrug thereof, or a pharmaceutically acceptable salt of the prodrug.

In a preferred embodiment of the method of treating diabetes, the diabetes is non-insulin dependent diabetes mellitus (Type II).

Also provided are methods of treating or preventing myocardial infarction, the methods comprising the step of administering to a patient having or at risk of having myocardial infarction a therapeutically effective amount of a compound of Formula II, or a stereoisomer, pharmaceutically acceptable salt or prodrug thereof, or a pharmaceutically acceptable salt of the prodrug.

Also provided are methods of treating or preventing a stoke, the methods comprising the step of administering to a patient having or at risk of having a stroke a therapeutically effective amount of a compound of Formula II, or a stereoisomer, pharmaceutically acceptable salt or prodrug thereof, or a pharmaceutically acceptable salt of the prodrug.

Also provided are methods of treating or preventing restenosis, the methods comprising the step of administering to a patient having or at risk of having restenosis a therapeutically effective amount of a compound of Formula II, or a stereoisomer, pharmaceutically acceptable salt or prodrug thereof, or a pharmaceutically acceptable salt of the prodrug.

Also provided are methods of treating or preventing Syndrome X, the methods comprising the step of administering to a patient having or at risk of having Syndrome X a therapeutically effective amount of a compound of Formula II, or a stereoisomer, pharmaceutically acceptable salt or prodrug thereof, or a pharmaceutically acceptable salt of the prodrug.

Also provided are methods of inhibiting apolipoprotein B secretion, the methods comprising administering to a patient in need of apolipoprotein B secretion inhibition an apolipoprotein B secretion inhibiting amount of a compound of Formula II, or a stereoisomer, pharmaceutically acceptable salt or prodrug thereof, or a pharmaceutically acceptable salt of the prodrug.

Also provided are methods of inhibiting microsomal triglyceride transfer protein, the methods comprising administering to a patient in need of microsomal triglyceride transfer protein inhibition a microsomal triglyceride transfer protein inhibiting amount of a compound of Formula II, or a stereoisomer, pharmaceutically acceptable salt or prodrug thereof, or a pharmaceutically acceptable salt of the prodrug.

Also provided are pharmaceutical compositions comprising a compound of Formula II, or a stereoisomer, pharmaceutically acceptable salt or prodrug thereof, or a pharmaceutically acceptable salt of the prodrug.

Also provided are kits for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X, the kits comprising:

a) a first pharmaceutical composition comprising a compound of Formula II, or a stereoisomer, pharmaceutically acceptable salt or prodrug thereof, or a pharmaceutically acceptable salt of the prodrug.

b) a second pharmaceutical composition comprising a second compound useful for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X; and c) a container for containing the first and second compositions.

Also provided are methods for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X, the methods comprising the step of administering to a patient having or at risk of having atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X a therapeutically effective amount of a compound of Formula II, a stereoisomer, pharmaceutically acceptable salt or prodrug thereof, or a pharmaceutically acceptable salt of the prodrug in combination with at least one additional compound useful for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X.

Also provided are pharmaceutical compositions comprising a compound of Formula II, or a stereoisomer, pharmaceutically acceptable salt or prodrug thereof, or a pharmaceutically acceptable salt of the prodrug, and at least one additional compound useful for the treatment or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, or Syndrome X.

Also provided are the compounds:

7-[(4'-trifluoromethyl-biphenyl-2-carbonyl)-amino]-quinoline-3-carboxylic acid (pentylcarbamoyl-phenyl-methyl)-amide;

7-[(4'-trifluoromethyl-biphenyl-2-carbonyl)-amino]-quinoline-3-carboxylic acid (diethylcarbamoyl-phenyl-methyl)-amide;

7-[(4'-trifluoromethyl-biphenyl-2-carbonyl)-amino]-quinoline-3-carboxylic acid -S-(pentylcarbamoyl-phenyl-methyl)-amide;

7-[(4'-trifluoromethyl-biphenyl-2-carbonyl)-amino]-quinoline-3-carboxylic acid -S-(diethylcarbamoyl-phenyl-methyl)-amide;

7-[(4'-trifluoromethyl-biphenyl-2-carbonyl)-amino]-quinoline-3-carboxylic acid -R-(pentylcarbamoyl-phenyl-methyl)-amide;

7-[(4'-trifluoromethyl-biphenyl-2-carbonyl)-amino]-quinoline-3-carboxylic acid -R-(diethylcarbamoyl-phenyl-methyl)-amide, pharmaceutically acceptable salts and prodrugs thereof, and pharmaceutically acceptable salts of the prodrugs.

DETAILED DESCRIPTION OF THE INVENTION

The present invention relates to compounds of Formula I and II, pharmaceutically acceptable salts of compounds of Formula I and II, prodrugs of compounds of Formula I and II, and pharmaceutically acceptable salts of the prodrugs of compounds of Formula I and II. The present invention also relates to methods of treatment and/or prevention of atherosclerosis, obesity, diabetes, hyperlipidemia, hyperlipoproteinemia, hypercholesterolemia, hypertriglyceridemia, hypoalphalipoproteinemia, pancreatitis, myocardial infarction, stroke, restenosis, and Syndrome X. In addition, the present invention relates to methods of inhibiting MTP and/or inhibiting the secretion of apolipoprotien B. Certain terms that are used in this application are defined below.

The term "alkyl" means a straight or branched chain hydrocarbon. Representative examples of alkyl groups include methyl, ethyl, propyl, isopropyl, butyl, isobutyl, tert-butyl, sec-butyl, pentyl, and hexyl.

The term "alkoxy" means an alkyl group bonded to an oxygen atom. Representative examples of alkoxy groups include methoxy, ethoxy, tert-butoxy, propoxy, and isobutoxy. Preferred alkoxy groups are $C_1$–$C_8$alkoxy.

The term "halogen" means fluorine, chlorine, bromine or iodine.

The term "alkenyl" means a branched or straight chain hydrocarbon having one or more carbon-carbon double bonds.

The term "alkynyl" means a branched or straight chain hydrocarbon having one or more carbon-carbon triple bonds.

The term "cycloalkyl" means a cyclic hydrocarbon. Examples of cycloalkyl groups include cyclopropyl, cyclobutyl, cyclopentyl, cyclohexyl and cycloheptyl. Preferred cycloalkyl groups are $C_3$–$C_8$cyloalkyl. It is also possible for the cycloalkyl group to have one or more double bonds, but is not aromatic. Examples of cycloalkyl groups having a double bond include cyclopentenyl, cyclohexenyl, cyclohexadienyl, cyclobutadienyl, and the like.

The term "perfluoroalkyl" means an alkyl group in which all of the hydrogen atoms have been replaced with fluorine atoms.

The term "acyl" means a group derived from an organic acid (—COOH) by removal of the hydroxy group (—OH).

The term "aryl" means a cyclic, aromatic hydrocarbon. Examples of aryl groups include phenyl and naphthyl.

The term "heteroatom" includes oxygen, nitrogen, sulfur, and phosphorous.

The term "heteroaryl" means an aromatic ring containing one or more heteroatoms. If the heteroaryl group contains more than one heteroatoms, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms.

The term "heterocycloalkyl" mean a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidyl, and pyrrolidinyl. Preferred heterocycloalkyl groups are five and six membered rings and contain from one to three heteroatoms. It is also possible for the heterocycloalkyl group to have one or more double bonds, but is not aromatic. Example of heterocycloalkyl groups containing double bonds include dihydrofuran, and the like.

It is also noted that the cyclic ring groups, i.e., aryl, heteroaryl, cycloalkyl, heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazaolyl, 1,2,4-oxadiazolyl, 1,2,5-oxadiazolyl, 1,3,4-oxadiazolyl, 1,2,3-triazolyl, 1,2,4-triazaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl ,and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, and 1 ,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule has been replaced with a different atom or with a molecule. The atom or molecule replacing the hydrogen atom is called a substituent. Examples of suitable substituents include, halogen, $-OC_1-C_8$alkyl, $-C_1-C_8$alkyl, $-CF_3$, $-NH_2$, $-NHC_1-C_8$alkyl, $-N(C_1-C_8$alkyl$)_2$, $-NO_2$, $-CN$, $-CO_2H$, $-CO_2C_1-C_8$alkyl, and the like.

The symbol "—" represents a covalent bond.

The term "therapeutically effective amount" means an amount of a compound that ameliorates, attenuates, or eliminates one or more symptoms of a particular disease or condition or prevents or delays the onset of one of more symptoms of a particular disease or condition.

The term "patient" means animals, such as dogs, cats, cows, horses, sheep, geese, and humans. Particularly preferred patients are mammals, including both males and females.

The term "pharmaceutically acceptable" means that the substance or composition must be compatible with the other ingredients of a formulation, and not deleterious to the patient.

The phrases "a compound of the present invention, a compound of Formula I (or II), or a compound in accordance with Formula I (or II)" and the like include the pharmaceutically acceptable salts of the compounds, prodrugs of the compounds, and pharmaceutically acceptable salts of the prodrugs.

The terms "reaction-inert solvent" or "inert solvent" refer to a solvent or mixture of solvents that does not interact with starting materials, reagents, intermediates or products in a manner that adversely affects the desired product.

The terms "treating", "treat" or "treatment" include preventative (e.g., prophylactic) and palliative treatment.

The term "MTP inhibitor" refers to any substance or agent or any combination of substances and/or agents that reduces, retards, or eliminates the biological action of MTP.

The term "apo B secretion inhibitor" refers to any substance or agent or any combination of substances and/or agents that reduces, retards, or eliminates the secretion of apo B resulting in lowered plasma levels of at least one compound containing apo B.

A patient in need of MTP inhibition and/or apo B secretion inhibition is a patient having a disease or condition in which MTP and/or apo B plays a role in the disease or condition. Examples of patients in need of MTP inhibition and/or apo B inhibition include patients having or at risk of having diabetes (including Type I and Type II, impaired glucose tolerance, insulin resistance, and diabetic complications, such as nephropathy, retinopathy, neuropathy and cataracts), atherosclerosis, obesity, hyperlipidemia, hyperlipoproteinemia, hypercholesterolemia, hypertriglyceridemia, hypoalphalipoproteinemia, pancreatitis, myocardial infarction, stroke, restenosis, or Syndrome X.

The characteristics of patients at risk of having atherosclerosis are well known to those in the art and include patients who have a family history of cardiovascular disease, including hypertension and atherosclerosis, obese patients, patients who exercise infrequently, patients with hypercholesterolemia, hyperlipidemia and/or hypertriglyceridemia, patients having high levels of LDL or Lp(a), patients having low levels of HDL (hypoalphalipoproteinemia), and the like.

Patients at risk of developing diabetes include patients who have a family history of diabetes, obese patients, patients who exercise infrequently, patients who have polycystic ovary syndrome, impaired glucose tolerance or exhibit insulin resistance, and patients who have or have had gestational diabetes. The preferred type of diabetes to be treated by the compounds of the present invention is non-insulin dependent diabetes mellitus, also known as Type II diabetes or NIDDM. It is also noted that the complications associated with diabetes can be treated or prevented through the methods disclosed herein.

Patients who are at risk of developing restenosis include patients who have undergone angioplasty procedures, or who have had bypass surgery. In general restenosis can occur whenever a blood vessel has been damaged or stressed. Balloon angioplasty is the most common type of angioplasty.

Patients who are at risk of having myocardial infarction are patients who are obese, have cardiovascular diseases, such as atherosclerosis, high cholesterol, or hypertension, and the like. In addition, patients having diabetes are at risk of developing cardiovascular diseases to a higher extent than persons not having diabetes. Such development of cardiovascular diseases can result in myocardial infarction.

Patients who are at risk of having a stoke include patients having atherosclerosis, hypercholesterolemia, hyperlipidemia, hypertriglyceridemia, hypoalphalipoproteinemia, diabetes, patients undergoing angioplasty procedures, bypass surgery or any other form of surgery, obese patients, and the like. Treating or preventing atherosclerosis, helps to lower the probability of having a stroke.

The compounds of the present invention are administered to a patient in a therapeutically effective amount. The compounds can be administered alone or as part of a pharmaceutically acceptable composition. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially. In addition, it should be recognized that the compositions may be different forms. For example, one or more compounds may be delivered via a tablet, while another is administered via injection or orally as a syrup. All combinations, delivery methods and administration sequences are contemplated.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, a prodrug thereof, or a salt of such compound or prodrug; and a second pharmaceutically active compound. The kit comprises a container for containing the separate compositions, such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . ." etc. Other variations of memory aids will be readily apparent. A "daily dose" can be a single tablet or capsule or several pills or capsules to be taken on a given day. Also, a daily dose of compounds of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, and injectable organic esters such as ethyl oleate. A preferred carrier is Miglyol®. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, gycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, Miglyol®, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or compounds are admixed under sterile conditions with a physiologically acceptable carrier, and any preservatives, buffers, or propellants that may be required. Opthalmic formulations, eye ointments, powders, and solutions are also contemplated as being within the scope of this invention.

In a preferred method of administering a compound of the present invention, the administration occurs prior to or during a somnolent period. The phrase "somnolent period" refers to a time frame when the patient is sleeping. The apo B secretion inhibitor and/or MTP inhibitor of the present invention is preferably administered prior to the normal sleeping period but can be administered during the somnolent period. An exemplary time for administering a compound of the present invention is at bedtime. It is noted that the somnolent period can be anytime during which the patient sleeps and includes day and night.

The compounds of the present invention can be administered to a patient at dosage levels in the range of about 0.1 to about 3,000 mg per day. A preferred dosage for a human is about 1 mg to about 1,000 mg per day. A more preferred dose is from about 1 mg to about 100 mg per day. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill in the art.

The following paragraphs describe exemplary formulations, dosages etc. useful for non-human animals. The administration of a compound of the present invention can be effected orally or non-orally, for example by injection. An amount of a compound of the present invention is administered such that an effective dose is received, generally a daily dose which, when administered orally to an animal is usually between 0.01 and 1000 mg/kg of body weight, preferably between 0.1 and 50 mg/kg of body weight. Conveniently, the compound can be carried in the drinking water so that a therapeutic dosage of the compound is ingested with the daily water supply. The compound can be directly metered into drinking water, preferably in the form of a liquid, water-soluble concentrate (such as an aqueous solution of a water soluble salt). Conveniently, the compound can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. It is important that the compound be thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of active compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound material across the top of the dressed feed.

The preferred medicated swine, cattle, sheep and goat feed generally contain from 1 to 400 grams of a compound of the present invention per ton of feed, the optimum amount for these animals usually being about 50 to 300 grams per ton of feed.

The preferred poultry and domestic pet feeds usually contain about 1 to 400 grams and preferably 10 to 400 grams of a compound of the present invention per ton of feed.

For parenteral administration in animals, the compounds of the present invention may be prepared in the form of a paste or a pellet and administered as an implant, usually under the skin of the head or ear of the animal.

In general, parenteral administration involves injection of a sufficient amount of a compound of the present invention to provide the animal with 0.01 to 100 mg/kg/day of body weight of the active ingredient. The preferred dosage for poultry, swine, cattle, sheep, goats and domestic pets is in the range of from 0.1 to 50 mg/kg/day.

Paste formulations can be prepared by dispersing a compound of the present invention in pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level. Moreover, it has been found that implants may also be made periodically during the animal treatment period in order to maintain the proper active agent level in the animal's body.

The terms pharmaceutically acceptable salts, esters, amides, or prodrugs means the carboxylate salts, amino acid addition salts, esters, amides, and prodrugs of the compounds of the present invention that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of the compounds of the present invention.

The term "salts" refers to inorganic and organic salts of compounds of the present invention. These salts can be prepared in situ during the final isolation and purification of a compound, or by separately reacting a purified compound in its free base form with a suitable organic or inorganic acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci*, 66:1–19 (1977).

Examples of pharmaceutically acceptable, non-toxic esters of the compounds of the present invention, if applicable, include $C_1$–$C_8$ alkyl esters. Acceptable esters also include $C_5$–$C_7$cycloalkyl esters, as well as arylalkyl esters such as benzyl. $C_1$–$C_4$ alkyl esters are preferred. Esters of compounds of the present invention may be prepared according to methods that are well known in the art.

Examples of pharmaceutically acceptable non-toxic amides of the compounds of the present invention include amides derived from ammonia, primary $C_1$–$C_8$ alkyl amines, and secondary $C_1$–$C_8$ dialkyl amines. In the case of secondary amines, the amine may also be in the form of a 5 or 6 membered heterocycloalkyl group containing at least one nitrogen atom. Amides derived from ammonia, $C_1$–$C_3$ primary alkyl amines, and $C_1$–$C_2$ dialkyl secondary amines are preferred. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A good discussion of the use of prodrugs is provided by T. Higuchi and W. Stella, "Pro-drugs as Novel Delivery Systems," Vol. 14 of the *A. C. S. Symposium Series*, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention comprises an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$) alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$) alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, $-P(O)(O(C_1-C_6)alkyl)_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as R-carbonyl, RO-carbonyl, NRR'-carbonyl where R and R' are each independently (($C_1$–$C_{10}$)alkyl, ($C_3$–$C_7$)cyCloalkyl, benzyl, or R-carbonyl is a natural α-aminoacyl or natural α-aminoacyl-natural α-aminoacyl, —C(OH)C(O)OY wherein (Y is H, ($C_1$–$C_6$)alkyl or benzyl), —C(OY$_0$)Y$_1$ wherein Y$_0$ is ($C_1$–$C_4$) alkyl and Y$_1$ is (($C_1$–$C_6$)alkyl, carboxy($C_1$–$C_6$)alkyl, amino($C_1$–$C_4$)alkyl or mono-N- or di—N,N—($C_1$–$C_6$)alkylaminoalkyl, —C(Y$_2$) Y$_3$ wherein Y$_2$ is H or methyl and Y$_3$ is mono-N- or di—N,N—($C_1$–$C_6$)alkylamino, morpholino, piperidin-1-yl or pyrrolidin-1-yl.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if a compound contains a double bond, both the cis and trans forms, as well as mixtures, are contemplated.

Mixtures of isomers, including stereoisomers can be separated into their individual isomers on the basis of their physical chemical differences by methods well know to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of this invention may be atropisomers (e.g., substituted biaryls) and are considered as part of this invention.

The compounds of the present invention may exist in unsolvated as well as solvated forms with pharmaceutically acceptable solvents such as water, ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the imidazole moiety are included in this invention. Also, for example, all keto-enol or imine-enamine forms of the compounds are included in this invention.

Those skilled in the art will recognize that the compound names contained herein may be based on a particular tautomer of a compound. While the name for only a particular tautomer may be used, it is intended that all tautomers are encompassed by the name of the particular tautomer and all tautomers are considered part of the present invention.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{33}P$, $^{32}P$, $^{35}S$, $^{18}F$, $^{125}I$, $^{131}I$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., 14C, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

In one aspect, the present invention concerns the treatment of diabetes, including impaired glucose tolerance, insulin resistance, insulin dependent diabetes mellitus (Type I) and non-insulin dependent diabetes mellitus (NIDDM or Type II). Also included in the treatment of diabetes are the diabetic complications, such as neuropathy, nephropathy, retinopathy or cataracts.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the present invention along with other agents that can be used to treat diabetes.

Representative agents that can be used to treat diabetes include insulin and insulin analogs (e.g. LysPro insulin); GLP-1 (7–37) (insulinotropin) and GLP-1 (7–36)-NH$_2$; sulfonylureas and analogs: chlorpropamide, glibenclamide, tolbutamide, tolazamide, acetohexamide, Glypizide®), glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, BRL49653; fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, Ro 16–8714, ICI D7114, CL 316,243; phosphodiesterase inhibitors: L-386,398; lipid-lowering agents: benfluorex; antiobesity agents: fenfluramine and orlistat; vanadate and vanadium complexes (e.g. Nagliyan®) and peroxovanadium complexes; amylin antagonists; glucagon antagonists; gluconeogenesis inhibitors; somatostatin analogs; antilipolytic agents: nicotinic acid, acipimox, WAG 994; and glycogen phosphorylase inhibitors, such as those disclosed in WO 96/39385 and WO 96/39384. Also contemplated in combination with compounds of the present invention are pramlintide acetate (Symlin™) and nateglinide. Any combination of agents can be administered as described above.

In addition, the compounds of the present invention can be administered in combination with other pharmaceutical agents such as cholesterol biosynthesis inhibitors and cholesterol absorption inhibitors, especially HMG-CoA reductase inhibitors and HMG-CoA synthase inhibitors, HMG-CoA reductase and synthase gene expression inhibitors, CETP inhibitors, biles acid sequesterants, fibrates, ACAT inhibitors, squalene synthetase inhibitors, anti-oxidants and niacin. The compounds of the present invention may also be administered in combination with naturally occurring compounds that act to lower plasma cholesterol levels. These naturally occurring compounds are commonly called nutraceuticals and include, for example, garlic extract, Benecol®, and niacin.

Specific cholesterol absorption inhibitors and cholesterol biosynthesis inhibitors are described in detail below. Additional cholesterol absorption inhibitors are known to those skilled in the art and are described, for example, in PCT WO 94/00480.

Any HMG-CoA reductase inhibitor may be employed as an additional compound in the combination therapy aspect of the present invention. The term HMG-CoA reductase inhibitor refers to a compound that inhibits the biosynthesis of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455–509 (1981); and the references cited therein). A variety of these compounds are described and referenced below. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors that can be used in combination with compounds of the present invention include Baycol®, Lescol®, Lipitor®, Mevacor®, Pravachol® and Zocor®.

Any HMG-CoA synthase inhibitor may be used as the second compound in the combination therapy aspect of this invention. The term HMG-CoA synthase inhibitor refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology*, 35:155–160 (1975); and *Methods of Enzymology*, 110: 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl4-oxo-2-oxetayl)-3,5,7-trimethyl-2,4-undecadienoic acid derivatives. Other HMG-CoA synthase inhibitors will be known to those skilled in the art.

Any compound that decreases HMG-CoA reductase gene expression may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology*, 110: 9–19 1985). Several such compounds are described and referenced below however other inhibitors of HMG-CoA reductase gene expression will be known to those skilled in the art. U.S. Pat. No. 5,041,432 discloses certain 15-substituted lanosterol derivatives. Other oxygenated sterols that suppress the biosynthesis of HMG-CoA reductase are discussed by E. I. Mercer (*Prog. Lip. Res.*, 32:357–416 1993).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below however other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.;* 6:1951–1954 (1996), respectively. Other CETP inhibitors that can be used in combination with compounds of the present invention are disclosed in WO 99/20302, EP 796846, EP818197, EP 818448, WO 99/14204, WO 99/41237, WO 95/04755, WO 96/15141, WO 96/05227, DE 19704244, DE19741051, DE 19741399, DE 19704243, DE 19709125, DE 19627430, DE 19832159, DE 19741400, JP 11049743, and JP 09059155. Preferred CETP inhibitors that can be used in combination with the compounds of the present invention include

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester,

[2S,4S] 4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S] 2-cyclopropyl-4-[(3,5-dichloro-benzyl)-methoxycarbonyl-amino]-6-trifluoromethyl-3,4-dihydro-2H-quinoline-1-carboxylic acid isopropyl ester; [2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester, and pharmaceutically acceptable salts and prodrugs thereof and salts of the prodrugs.

Any ACAT inhibitor can serve as the second compound in the combination therapy aspect of this invention. The term ACAT inhibitor refers to compounds that inhibit the intracellular esterification of dietary cholesterol by the enzyme acyl CoA: cholesterol acyltransfer. Such inhibition may be determined readily by one of skill in the art according to standard assays, such as the method of Heider et al. described in *Journal of Lipid Research.*, 24:1127 (1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity.

Any compound having activity as a squalene synthetase inhibitor can serve as an additional compound in the combination therapy aspect of the instant invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Methods of Enzymology*, 15:393–454 (1969); and *Methods of Enzymology*, 110: 359–373 (1985); and references cited therein). A summary of squalene synthetase inhibitors has been complied in *Curr. Op.Ther. Patents*, 861–4, (1993). European patent application publication Number 0 567 026 A1 discloses certain 4,1-benzoxazepine derivatives as squalene synthetase inhibitors and their use in the treatment of hypercholesterolemia and as fungicides. European patent application publication Number 0 645 378 A1 discloses certain seven- or eight-membered heterocycles as squalene synthetase inhibitors and their use in the treatment and prevention hypercholesterolemia and fungal infections. European patent application publication Number 0 645 377 A1 discloses certain benzoxazepine derivatives as squalene synthetase inhibitors useful for the treatment of hypercholesterolemia or coronary sclerosis. European patent application publication Number 0 611 749 A1 discloses certain substituted amic acid derivatives useful for the treatment of arteriosclerosis. European patent application publication Number 0 705 607 A2 discloses certain condensed seven- or eight-membered heterocyclic compounds useful as antihypertriglyceridemic agents. PCT publication WO 96/09827 discloses certain combinations of cholesterol absorption inhibitors and cholesterol biosynthesis inhibitors including benzoxazepine derivatives and benzothiazepine derivatives. European patent application publication Number 0 701 725 A1 discloses a process for preparing certain optically-active compounds, including benzoxazepine derivatives, having plasma cholesterol and triglyceride lowering activities. Other compounds that are marketed for hyperlipidemia, including hypercholesterolemia and which are intended to help prevent or treat atherosclerosis include bile acid sequestrants, such as Colestid®, LoCholest® and Questran®; and fibric acid derivatives, such as Atromid®, Lopid® and Tricor®. These compounds can also be used in combination with a compound of the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a compound of the present invention, any lipase inhibitor or glucosidase inhibitor may be employed. Preferred lipase inhibitors comprise gastric or pancreatic lipase inhibitors such as orlistat. Preferred glucosidase inhibitors comprise amylase inhibitors.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987).

A variety of lipase inhibitors are known to one of ordinary skill in the art. However, in the practice of the methods, pharmaceutical compositions and kits of the instant invention, generally preferred lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267.

The pancreatic lipase inhibitors lipstatin, 2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), 2S, 3S, 5S)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-1 21 898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4'-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of Actinomycetes strain MG147-CF2, are disclosed in Kitahara, et al., *J. Antibiotics*, 40 (11), 1647–1650 (1987).

The lipase inhibitor esteracin, and certain processes for the preparation thereof by the microbial cultivation of Streptomyces strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of Actinomycetes strain MG7-G1, are disclosed in Umezawa, et al., *J. Antibiotics*, 33,1594–1596 (1980). The use of ebelactones A and B in the suppression of monoglyceride formation is disclosed in Japanese Kokai 08-143457, published Jun. 4, 1996.

The lipase inhibitor RHC 80267, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen*, 562, 205–229 (1949). The ability of RHC 80267 to inhibit the activity of myocardial lipoprotein lipase is disclosed in Carroll et al., *Lipids*, 27, pp. 305–307 (1992) and Chuang et al., *J. Mol. Cell Cardiol.*, 22, 1009–1016 (1990).

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

In combination with a compound of the present invention, any glucosidase inhibitor may be employed, however, a generally preferred glucosidase inhibitor comprises an amylase inhibitor. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors are known to one of ordinary skill in the art. However, in the practice of the methods and pharmaceutical compositions of the instant invention, generally preferred glucosidase inhibitors are those inhibitors that are selected from the group consisting of acarbose, adiposine, voglibose, miglitol, emiglitate, MDL-25637, camiglibose, tendamistate, Al-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1-yl]amino]-α-glucopyranosyl-(1→4)-O-α-D-glucopyranosyl-(1→4)-D-glucose, the various amino sugar derivatives related thereto and a process for the preparation thereof by the microbial cultivation of Actinoplanes strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254,256. Additionally, a process for the preparation and purification of adiposine is disclosed in Namiki et al., *J. Antiobiotics*, 35,1234–1236 (1982).

The glucosidase inhibitor voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydroxymethyl)

piperidino]-α-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor tendamistat, the various cyclic peptides related thereto and processes for the preparation thereof by the microbial cultivation of *Streptomyces tendae* strains 4158 or HAG 1226, are disclosed in U.S. Pat. No. 4,451,455.

The amylase inhibitor Al-3688, the various cyclic polypeptides related thereto, and a process for the preparation thereof by the microbial cultivation of *Streptomyces aureofaciens* strain FH 1656, are disclosed in U.S. Pat. No. 4,623,714.

The amylase inhibitor trestatin, consisting of a mixture of trestatin A, trestatin B and trestatin C, the various trehalose-containing aminosugars related thereto and a process for the preparation thereof by the microbial cultivation of *Streptomyces dimorphogenes* strains NR-320-OM7HB and NR-320-OM7HBS, are disclosed in U.S. Pat. No. 4,273,765.

The glucosidase inhibitor pradimicin-Q and a process for the preparation thereof by the microbial cultivation of *Actinomadura verrucospora* strains R103-3 or A10102, are disclosed in U.S. Pat. Nos. 5,091,418 and 5,217,877 respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091,524.

Preferred lipase inhibitors comprise compounds selected from the group consisting of lipstatin, tetrahydrolipstatin, FL-386, WAY-121898, Bay-n-3176, valilactone, esteracin, ebelactone A, ebelactone B, RHC 80267, stereoisomers thereof, and pharmaceutically acceptable salts of said compounds and stereoisomers. The compound tetrahydrolipstatin is especially preferred.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, Al-3688 and trestatin.

In addition, combinations of the present invention include the use of more than one compound of the present invention, and use of compounds of the present invention with other MTP inhibitors and/or apo B secretion inhibitors.

A variety of apo B secretion/MTP inhibitors are known to one of ordinary skill in the art. Although any apo B secretion/MTP inhibitor may be used in the practice of the methods and pharmaceutical compositions of the instant invention, generally preferred apo B secretion/MTP inhibitors include those compounds that are disclosed in, for example, European Patent Application Publication Numbers EP 643057, EP 719763, EP 753517, EP 764647, EP 765878, EP 779276, EP 779279, EP 799828, EP 799829, EP 802186, EP 802188, EP 802192, and EP 802197; PCT Application Publication Numbers WO 96/13499, WO 96/33193, WO 96/40640, WO 97/26240, WO 97/43255, WO 97/43257, WO 98/16526 and WO 98/23593; and U.S. Pat. Nos. 5,595,872; 5,646,162; 5,684,014; 5,712,279; 5,739,135 and 5,789,197.

Especially preferred apo-B secretion/MTP inhibitors are those biphenyl-2-carboxylic acid-tetrahydroisoquinolin-6-yl amide derivatives disclosed in PCT Application Publication Numbers WO 96/40640 and WO 98/23593. Especially preferred apo B secretion/MTP inhibitors disclosed in PCT Application Publication Numbers WO 96/40640 and WO 98/23593, and useful in the methods and pharmaceutical compositions of the present invention, are 4'-trifluoromethyl-biphenyl-2-carboxylic acid-[2-(1H-[1,2,4]triazol-3-ylmethyl)-1,2,3,4-tetrahydroisoquin-6-yl]-amide and 4'-trifluoromethyl-biphenyl-2-carboxylic acid-[2-(acetylaminoethyl)-1,2,3,4-tetrahydroisoquinolin-6-yl]-amide.

Another especially preferred class of apo B secretion/MTP inhibitors is disclosed in U.S. Pat. Nos. 5,595,872; 5,721,279; 5,739,135 and 5,789,197.

Especially preferred apo B secretion/MTP inhibitors disclosed in U.S. Pat. Nos. 5,595,872; 5,721,279; 5,739,135 and 5,789,197 and useful in the methods and pharmaceutical compositions of the present invention, are 9-(4-{4-[4'trifluoromethyl-biphenyl-2-carbonyl)-amino]-piperidin-1-yl}-butyl-9H-fluorene-9-carboxylic acid-(2,2,2-trifluoroethyl)-amide and 9-{4-[4-(2-benzothiazol-2-yl-benzoylamino)-piperidin-1-yl]-butyl}-9H-fluorene-9-carboxylic acid-(2,2,2-trifluoroethyl)-amide.

Another class of especially preferred apo B secretion/MTP inhibitors is disclosed in PCT Application Publication Number WO 98/16526.

Especially preferred apo B secretion/MTP inhibitors disclosed in PCT Application Publication Number WO 98/16526, and useful in the methods and pharmaceutical compositions of the present invention, are [11a-R]-8-[(4-cyanophenyl)methoxy]-2-cyclopentyl-7-(prop-2-enyl)-2,3,11,11 a-tetrahydro-6H-pyrazino[1,2b]isoquinoline-1,4-dione and [11 a-R]-cyclopentyl-7-(prop-2-enyl)-8-[(pyridin-2-yl)methoxy]-2,3,11,11a-tetrahydro-6H-pyrazino[1,2b]isoquinoline-1,4-dione.

Another especially preferred class of apo B secretion/MTP inhibitors is disclosed in U.S. Pat. No. 5,684,014.

An especially preferred apo B secretion/MTP inhibitor disclosed in U.S. Pat. No. 5,684,014, and useful in the methods and pharmaceutical compositions of the present invention, is 2-cyclopentyl-2-[4-(2,4-dimethyl-pyrido[2,3-b]indol-9-ylmethyl)-phenyl]-N-(2-hydroxy-1-phenyl-ethyl)-acetamide.

Yet another class of especially preferred apo B secretion/MTP inhibitors is disclosed in U.S. Pat. No. 5,646,162.

An especially preferred apo B secretion/MTP inhibitor disclosed in U.S. Pat. No. 5,646,162 and useful in the methods and pharmaceutical compositions of the present invention, is 2-cyclopentyl-N-(2-hydroxy-1-phenylethyl)-2-[4-(quinolin-2-ylmethoxy)-phenyl]-acetamide.

All documents cited in this patent application are hereby incorporated by reference.

In another aspect of the present invention, the compounds of Formula I can be used in combination with another anti-obesity agent. The additional anti-obesity agents is preferably selected from the group consisting of a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a neuropeptide-Y antagonist such as NPY-1 or NPY-5, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

Especially preferred anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl}acetic acid, {4-[2-(2-[6-aminopyridin-3-yl]-2(R)-hydroxyethylamino)ethoxy]phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R)-hydroxyethylamino)ethoxy]phenoxy}acetic acid.

The examples presented below are intended to illustrate particular embodiments of the invention, and are not intended to limit the scope of the specification, including the claims, in any manner.

EXAMPLES

Chemical Examples

Exemplary processes for the manufacture of the compounds of the invention are provided below and are illustrated by reaction schemes. These processes may be carried out in sequential or convergent synthetic routes. Purification procedures include crystallization and normal phase or reverse phase chromatography.

As a general note, the preparation of the compounds described herein may require protection of remote functionality (e.g., primary amine, secondary amine, carboxyl). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene and P. G. M. Wuts, *Protective Groups in Organic Synthesis*, John Wiley & Sons, New York, 1991.

The following abbreviations are used herein.

| | |
|---|---|
| ms | mass spectra |
| APCI | atmospheric pressure chemical ionization |
| NMR | nuclear magnetic resonance |
| h | hour(s) |
| d | day(s) |
| min | minute(s) |
| EDTA | ethylene diaminetetraacetic acid |
| Triton-X ® | polyoxyethyene ether |
| SDS | sodium dodecyl sulfate |
| SDS-PAGE | sodium dodecyl sulfate polyacrylamide gel electrophoresis |
| g | gram(s) |
| mmol | millimoles |
| mp | melting point |

General Synthetic Procedure

The compounds of the present invention can be prepared as illustrated in Scheme 1 below. The quinoline II can be prepared by the method of C. C. Price, et al. in the *Journal of the American Chemical Society*, 69, 374–376 (1947). Conversion of the quinoline II to the chloroquinoline III can be achieved by treatment with oxalyl chloride, POCl$_3$ or PCl$_5$. After recrystallization, chloroquinoline III can be reduced to the aminoquinoline IV by reaction with ammonium formate and palladium on carbon. Reaction of amine IV with 4'-trifluoromethyl-biphenyl-2-carbonyl chloride affords the amide V, which can be hydrolyzed to the carboxylic acid VI by treatment with lithium hydroxide. Amides of the general formula Ia can be obtained by condensation of carboxylic acid VI with the appropriate amine VII under the usual amide coupling conditions known to those skilled in the art, such as reaction with N,N'-dialkylcarbodiimide (preferably 1-(3-dimethylaminopropyl)-3-ethylcarbodiimide hydrochloride [EDCI]), 1-hydroxybenzotriazole (HOBT), and an amine base (preferably triethylamine [TEA]) in a polar solvent (preferably dichloromethane) for a time between 1 and 100 hours (preferably overnight), at a temperature between 0 and 100° C. (preferably ambient temperature). Amines of formula VII can be obtained from commercial sources or prepared by a variety of methods known to those skilled in the art, including for instance, those shown in synthetic organic textbooks. Methods for obtaining the amines of formula VII in enantiomerically enriched form, not available from commercial sources, are known to those skilled in the art and include resolution by selective crystallization of a diastereomeric salt of an enantiomerically pure chiral acid (e.g., A. Ault in *Organic Syntheses, Collective Volumes*, V: 932–936 (1973)) or an enantioselective synthesis such as those described by G. Alvara et al., in *Journal of the Chemical Society, Perkins Transcripts* 1: 777–783 (1998). Additionally, the amines VII or the amides I, if chiral, can be obtained in enantiomerically pure form by resolving the enatiomers of the racemate by preparative chiral high pressure liquid chromatography.

It is also noted that the amide nitrogen in compounds of the present invention can be alkylated using procedures well known in the art. For example, the amide nitrogen can be alkylated using an alkyl halide such as methyl iodide and a base such as sodium hydride or potassium carbonate in a polar, aprotic solvent such as dimethylformamide.

Scheme

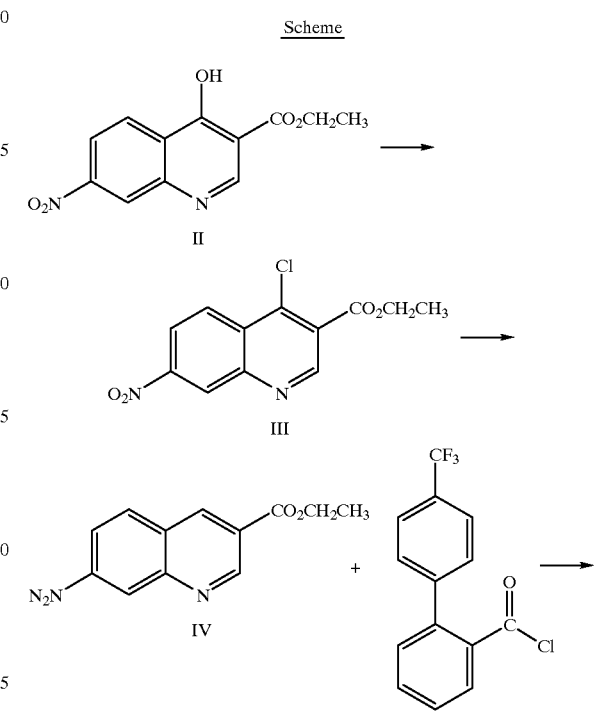

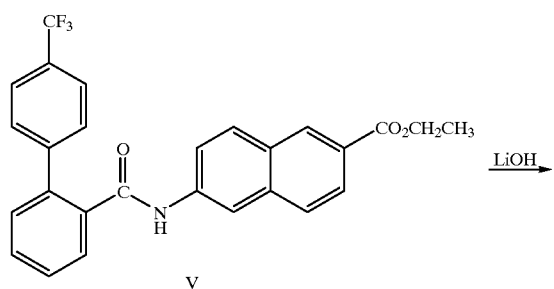

V

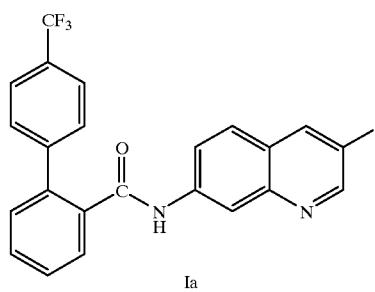

VI

HNR¹R²
VII
EDCI, HOBT, TEA

Ia

Compounds of Formula II wherein R³ is hydrogen can be made generally as follows.

II a. reacting

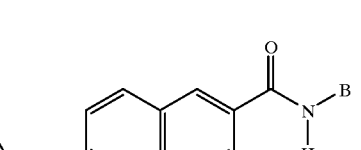 with 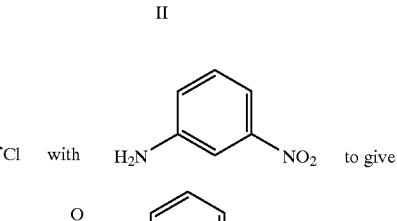 to give a. reducing

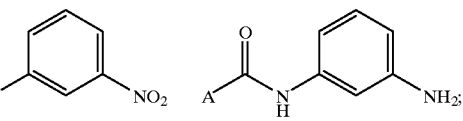

c. reacting

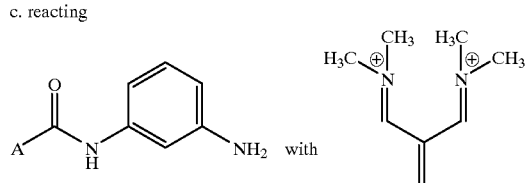

d. oxidizing

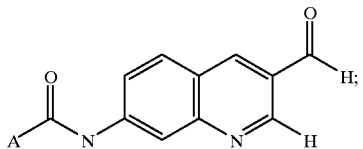; to

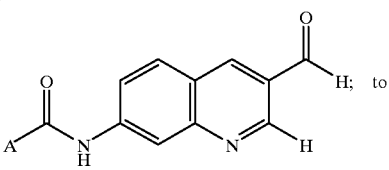; and e. coupling

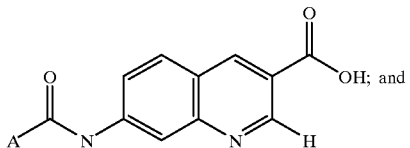

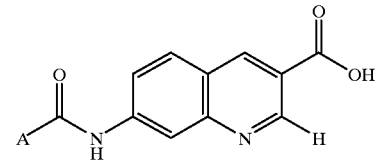

with H₂N—B to form a compound of Formula Iz.

In step a of the above method, the nitro amide compound can be made by coupling 3-nitroaniline (Aldrich, Milwaukee, Wis.) with an acid chloride. An acid chloride, which is an activated carboxylic acid, can be made from the corresponding carboxylic acid following procedures that are well known in the art. A preferred acid chloride is 4'-trifluoromethyl-biphenyl-2-carbonyl chloride. Examples of reagents that can be used to make an acid chloride (or acid halide) from an acid include oxalyl chloride, thionyl chloride, $PCl_3$, $PBr_3$, $Ph_3P$ in $CCl_4$, and cyanuric fluoride. The coupling of an amine with a carboxylic acid (typically, an activated carboxylic acid such as an acid chloride) is well known in the art. A preferred coupling method of step a of the present invention uses a base such as triethylamine in a polar, aprotic solvent such as tetrahydrofuran. Many procedures that couple a carboxylic acid or derivative with an amine to form an amide have been reported. Many involve the activation of a carboxylic acid to an acid chloride or anhydride followed by coupling with an amine. Many coupling reagents directly activate an acid for reaction with an amine including carbodiimides such as dicyclohexylcarbodiimide (DCC), propanephosphonic anhydride, and various hydroxybenzotriazole derivatives. In many cases it is possible to interconvert from other carboxylic acid derivatives such as an ester, nitrile, or amide to the desired amide. These methods are summarized in Richard C. Larock, *Comprehensive Organic Transformations,* 2nd ed, Wiley, N.Y., 1999, pp. 1941–1949, 1953–1957, 1978–1982, 1988–1990, and 1973–1976.

In step b of the above method, the nitro amide made in step a is reduced to an amino amide. The reduction of a nitro group to an amino group is well known to those skilled in the art. For example, in a preferred embodiment of the present invention, palladium dihydroxide (also known as Pearlman's catalyst) and ammonium formate in a mixture of isopropanol and ethyl acetate can be used. The reduction of an aryl nitro group to an aryl amine has been accomplished in many ways. Common methods include the reduction with a metal catalyst such as palladium on carbon or Rainey nickel and hydrogen gas. Transfer hydrogenation with hydrazine/graphite or cyclohexene/palladium is also effective. Other hydride sources, such as sodium borohydride with various metal salts and lithium aluminum hydride may also be used. Nitro reductions have also been accomplished with zinc or tin and hydrochloric acid. These methods and others are summarized by Richard C. Larock in *Comprehensive Organic Transformations,* 2nd ed, Wiley, N.Y., 1999, pp. 821–828.

In step c of the above method, a quinoline ring system is formed by reacting the amino amide produced in step b with the diamine reagent (2-dimethylaminomethylene-1,3-bis(dimethylimmonio)propane):

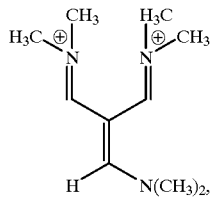

preferably the bis(tetrafluoroborate) salt (2BF$_4^-$). The diamine reagent used in this step can be prepared by reacting bromoacetic acid or bromoacetyl chloride with phosphorus oxychloride and N,N-dimethylformamide, followed by tetrafluoroboric acid. The generation of this reagent is set forth specifically below. The use of this reagent to form the quinoline ring system is advantageous because it does not require a high temperature cyclization step.

In step d above, the newly formed quinoline, which contains an aldehyde group, is oxidized to form a quinoline carboxylic acid. The oxidation of an aldehyde group to a carboxylic acid group is well known to those skilled in the art. A preferred oxidation method of the present invention uses sodium chlorite. Other reagents than can be used to oxidize an aldehyde to a carboxylic acid include potassium permanganate, sodium periodate, ruthenium tetroxide, chromium trioxide, hydrogen peroxide, sodium perchlorate, or the like.

Next, the quinoline carboxylic acid formed in step d above is coupled with an amine having the formula H$_2$N—B. The coupling of an amine with a carboxylic acid to form an amide is well known to those skilled in the art. A preferred coupling method of the present invention uses 1-(3-dimethylaminopropyl)-3-ethylcarbodiimide hydrochloride, 1-hydroxybenzotriazole, triethylamine, and dichloromethane. A preferred amine is phenyl-(2-pyridyl)-methylamine. Many procedures to convert a carboxylic acid or derivative to an amide have been reported as described above.

The compounds of Formula II can also be made as follows:

1.) reacting

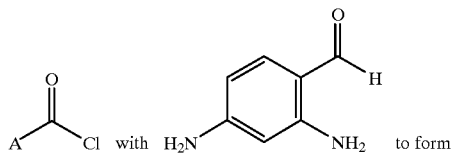

to form

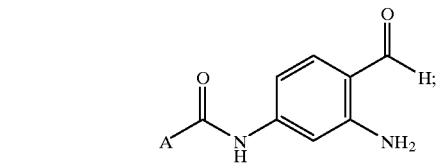

2. reacting

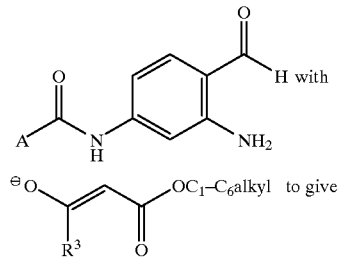

to give

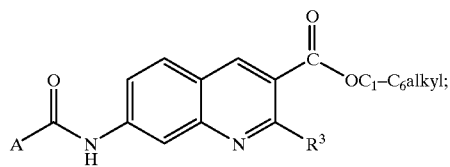

3. hydrolyzing

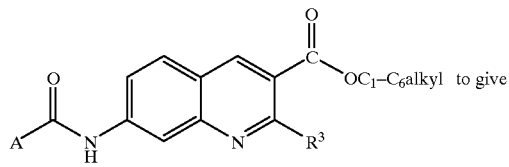

to give

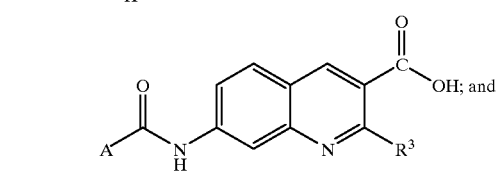

4. reacting

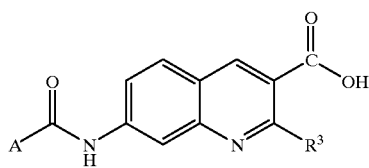

with H$_2$N—B to provide a compound of Formula II.

In step 1 above, an amino aldehyde amide is formed by reacting an acid chloride with 2,4-diaminobenzaldehyde, which is a known compound. [See, for example, Merlic, C.

A. et al., *J. Org. Chem.*, 1995, 60, 3365–3369.]. The acid chloride can be formed from the corresponding carboxylic acid by procedures that are well known in the art. 2,4-Diaminobenzaldehyde can also be obtained by reducing 2,4-dinitrobenzaldehyde (Aldrich, Milwaukee, Wis.). Reductions of a nitro group to an amino group are well known. A preferred reduction uses iron dust, glacial acetic acid and ethyl acetate. The reduction of an aryl nitro group to an aryl amine has been accomplished in many ways. Common methods include the reduction with a metal catalyst such as palladium on carbon or Rainey nickel and hydrogen gas. Transfer hydrogenation with hydrazine/graphite or cyclohexene/palladium is also effective. Other hydride sources such as sodium borohydride with various metal salts and lithium aluminum hydride may be used. Nitro reductions have also been accomplished with zinc or tin and hydrochloric acid. These reactions and others are summarized by Richard C. Larock in *Comprehensive Organic Transformations*, 2nd ed, 1999, pp. 821–828.

The formation of the amino aldehyde amide is accomplished by coupling an acid chloride with an amino group of 2,4-diaminobenzaldehyde. In a preferred embodiment of the method, the coupling is accomplished using poly(4-vinylpyridine). The poly(4-vinylpyridine) (CAS# 9017-40-7) can be obtained as 2% or 25% crosslinked with divinylbenzene from Aldrich, Milwaukee, Wis. The use of poly(4-vinylpyridine) provides for greater selectivity with regard to reaction at the 4-amino group of the 2,4-diaminobenzaldehyde.

In step 2 above the amino aldehyde amide is reacted with

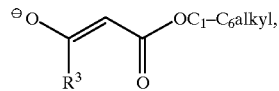

preferably the sodium salt, to provide a quinoline ester. The reaction can be run in glacial acetic acid.

In step 3 above, the quinoline ester is hydrolyzed to form a quinoline carboxylic acid. The hydrolysis of esters is well known to those skilled in the art. Preferred reagents that can be used include a base such as sodium hydroxide in a mixture of methanol and tetrahydrofuran. Other reagents that can be used to hydrolyze an ester to a carboxylic acid include lithium hydroxide, potassium hydroxide or barium hydroxide in methanol, tetrahydrofuran or mixtures thereof. Additional reagents that can be used are set forth in *Organic Reactions*, 1976, 24, 187; and E. Haslam in *Tetrahedron*, 1980, 36, 2409–2433.

In step 4 above, the quinoline carboxylic acid is coupled with an amine $H_2N$—B to provide a compound of Formula II. A preferred amine is phenyl-(2-pyridyl)-methylamine. Many procedures to couple a carboxylic acid or derivative with an amine to form an amide have been reported as described above.

The compounds of Formula II can also be synthesized by the following procedure:

A. reacting

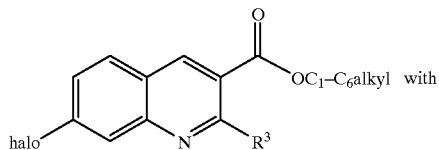

-continued

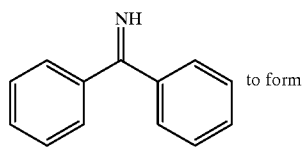

to form

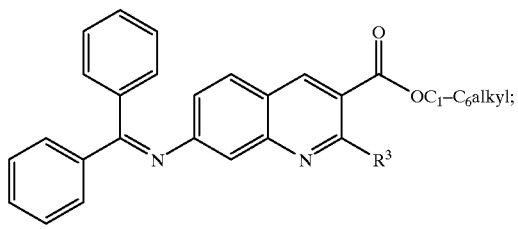

B. hydrolyzing

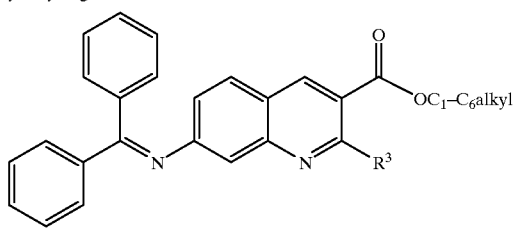

to form

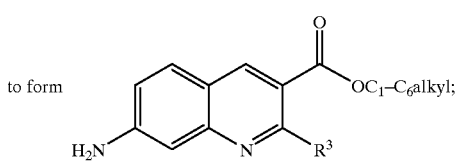

C. reacting

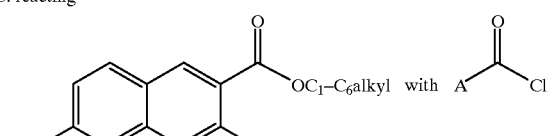

to form

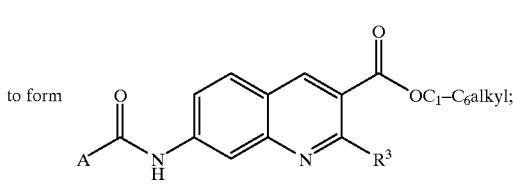

D. hydrolyzing

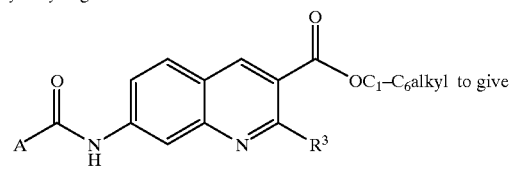

to give

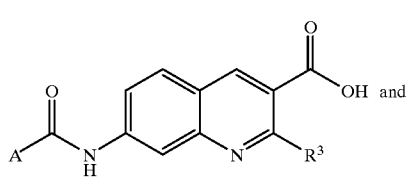

and

E. reacting

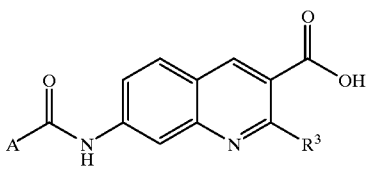

with H$_2$N—B to provide a compound of Formula II.

In step A above, a halo quinoline ester is reacted with benzophenone imine to form a benzhydrylidene amino quinoline ester. Preferred reagents used to accomplish the reaction include benzophenone imine, tri(dibenzylidieneacetone)dipalladium, 2-(dicyclohexylphosphino)biphenyl, and sodium -tert-butoxide in toluene. The halo quinoline ester is known. See, for example, Silva, Y. et al., *Acta Cient. Venez.,* 41, 130–131 (1990). Alternatively, the halo quinoline ester can be made by reducing 4-chloro-2-nitrobenzaldehyde to 4-chloro-2-aminobenzaldehyde. 4-Chloro-2-nitrobenzaldehyde can be obtained from P.H.T. International, Inc., Charlotte, N.C. The reduction of a nitro group to an amino group is well known to those skilled in the art. Examples of additional suitable reagents are set forth above. A preferred reduction uses iron powder, hydrochloric acid and a solvent of aqueous ethanol. Next, the 4-chloro-2-aminobenzaldehyde is reacted with 3-hydroxy-acrylic acid ethyl ester, sodium salt, to form the halo quinoline ester.

In step B above, the benzhydrylidene amino quinoline ester is hydrolyzed to form an amino quinoline ester. Preferred hydrolysis reagents are hydrochloric acid and ethanol. Other hydrolysis reagents include mineral acids and water, hydrogen and palladium on carbon, and hydroxylamine.

In step C above, the amino quinoline ester is reacted with an acid chloride to form an amide quinoline ester. Preferred reaction conditions include diisopropylamine in CH$_2$Cl$_2$. The reaction of an acid chloride (i.e., an activated carboxylic acid) with an amine to form an amide is well known to those skilled in the art, and other suitable reagents are set forth above.

In step D above, the amide quinoline ester is hydrolyzed to form an amide quinoline carboxylic acid. Preferred reagents include sodium hydroxide in methanol and tetrahydrofuran. Other reagents that can be used to hydrolyze an ester to a carboxylic acid include lithium hydroxide, potassium hydroxide, barium hydroxide in methanol or tetrahydrofuran or mixtures thereof. Other examples of ester hydrolysis are set forth in *Organic Reactions,* 1967, 24, 187; and *Tetrahedron,* 1980, 36, 2409.

In step E above, the amide quinoline carboxylic acid is reacted with an amine of formula HN—B to form a compound of Formula II.

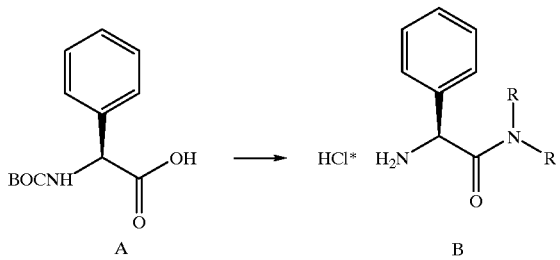

Synthesis of B: A solution of Boc-D-phenylglycine (5 g, 19.9 mmol) and bromo-tris-pyrrolidino-phosphonium hexaflourophosphate (PyBrOP) (9.28 g, 19.9 mmol) and an amine (HNRR) (21.89 mmol) in methylene chloride (70 mL) at 0° C. was added diisopropylethylamine. The mixture is stirred at 0° C. for 30 minutes and then allowed to warm to room temperature. Stirring is continued until the Boc-D-phenylglycine is consumed as determined by TLC. The reaction mixture is transferred to a 500 mL separatory flask and dilute with ether (200 mL). The mixture is washed successively with 1N HCl (100 mL), water (50 mL) and brine (50 mL). The ether fraction is dried over magnesium sulfate and filtered and the filtrate is concentrated to a colorless foam. The oil is dissolved in a mixture of 30% ethyl acetate in hexanes and filtered through a pad of silica gel. The silica gel was washed with additional 30% ethyl acetate in hexanes (250 mL). The filtrate is concentrated to provide the desired product as a colorless solid.

The solid is dissolved in 3 volumes of 4M HCl in dioxanes and the mixture is stirred at room temperature until the starting material in consumed as determined by TLC analysis. The reaction mixture is concentrated under reduced pressure to provide B as the hydrochloride salt.

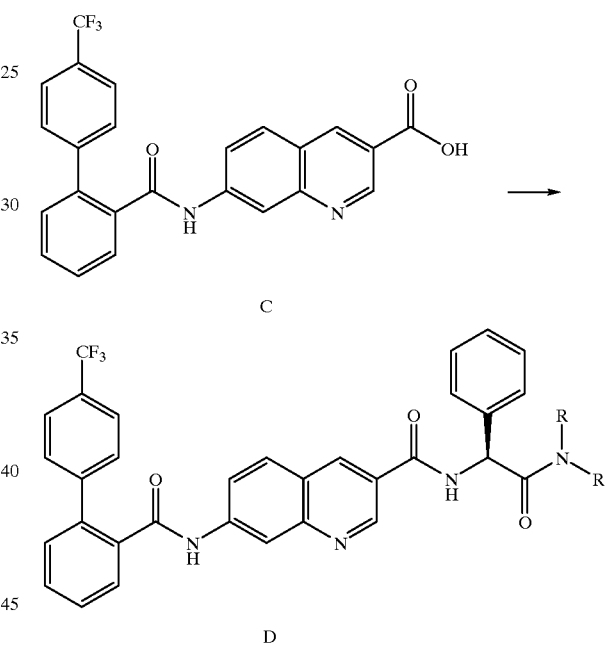

Synthesis of D: B (6.52 mM), C (2.37 g, 5.4 mM), and PyBrOP (2.52 g, 5.4 mM), are dissolved in DMF (60 mL). The mixture is cooled to 0° C. and then treated with diisopropylethylamine (2.82 mL, 16.2 mM). The mixture is stirred at 0° C. for 30 minutes and then allowed to warm to room temperature, stirring is continued until C is consumed. The mixture is poured into water (200 mL) and the precipitated is collect by vacuum filtration. The solid is dissolved in ethyl acetate (100 mL) and the mixture is dried with magnesium sulfate. The mixture is filtered and the filtrate is concentrated under reduced pressure. The residue is purified by flash chromatography or recrystalization to give D.

Preparation 1

4-Chloro-7-nitro-quinoline-3-carboxylic acid ethyl ester

4-Hydroxy-7-nitro-quinoline-3-carboxylic acid ethyl ester (15.6 g, 59.5 mmol) was suspended in chloroform (250 ml) and oxalyl chloride (20.7 ml, 30.2 g, 238 mmol) was added, followed by dimethyl formamide (0.4 ml, 0.38 g, 5.2 mmol). After heating at reflux for 2.5 h, the mixture was added to 300 ml of a 2N aqueous sodium hydroxide solution cooled in an ice/water bath. After stirring vigorously for 30 minutes, the aqueous layer was extracted with chloroform (200 ml). The combined organic phases were washed with water, brine and then dried over anhydrous magnesium sulfate. After vacuum filtration, the solution was concentrated under vacuum to provide 15.6 g of a fluffy brown solid. This solid was transferred to a Soxleht thimble and extracted with dichloromethane for 4 h employing a Soxleht extractor. Concentration of the dichloromethane solution under vacuum yielded 14.68 g of a tan solid. This solid was crystallized by dissolving in 400 ml of hot acetone and cooling to 0° C. overnight. The solid was collected by filtration, rinsing with ice-cold acetone, to yield 9.91 g of the title product as light yellow needles.

MS (APCI) 281 and 283 (M+1)$^+$ $^1$H NMR (CDCl$_3$) 1.45 (t, 3H, J=7.0 Hz), 4.50 (q, 2H, J=7.0 Hz), 8.42 (dd, 1H, J=9.3, 2.2 Hz), 8.55 (d, 1H, J=9.3 Hz), 8.98 (d, 1H, J=2.2 Hz), 9.29 (s, 1H).

Preparation 2

7-Amino-quinoline-3-carboxylic acid ethyl ester

4-Chloro-7-nitro-quinoline-3-carboxylic acid ethyl ester (14.57 g, 51.9 mmol) was suspended in methanol (210 ml) as palladium on carbon (10% palladium on carbon combined with an equal weight of water, 2.91 g) was added, followed by ammonium formate (13.09 g, 208 mmol). After heating at reflux for 3 h, the mixture was filtered through Celite® while still warm, rinsing with additional methanol to elute the color from the Celites®. Concentration of the filtrate under vacuum yielded 13.6 g of a yellow solid. This material was combined with 350 ml of acetone and the resulting slurry stirred for 1 h before filtration and concentration of the filtrate yielded 10.85 g of the title compound as a yellow solid.

MS (APCI) 217 (M+1)$^+$ $^1$H NMR (DMSO-d$_6$) 1.34 (t, 3H, J=7.2 Hz), 4.34 (q, 2H, J=7.2 Hz), 6.34 (bs, 2H), 6.96 (d, 1H, J=2.0 Hz), 7.06 (dd, 1H, J=8.9,2.3 Hz), 7.81 (d, 1H, J=8.9 Hz), 8.59 (d, 1H, J=2.0 Hz), 9.03 (d, 1H, J=2.0 Hz).

Preparation 3

4'-Trifluoromethyl-biphenyl-2-carbonyl chloride

4'-Trifluoromethyl-biphenyl-2-carboxylic acid (25 g, 94 mmol) was combined with thionyl chloride (35 ml, 470 mmol) and the mixture was heated at reflux. After 2 h, the mixture was concentrated under vacuum to afford 26.5 g of the title product as a light yellow oil.

$^1$H NMR (CDCl$_3$) 7.37 (dd, 1H, J=7.6, 1.1 Hz), 7.43 (d, 2H, J=8.1 Hz), 7.55 (td, 1H, J=7.7, 1.3 Hz), 7.66 (td, 1H, J=7.5, 1.3 Hz), 7.68 (d, 2H, J=8.1 Hz), 8.11 (dd, 1H, J=7.9, 1.2 Hz).

Preparation 4

7-[(4'-Trifluoromethyl-biphenyl-2-carbonyl)-amino]-quinoline-3-carboxylic acid ethyl ester 7-Amino-quinoline-3-carboxylic acid ethyl ester (8.6 g, 39.8 mmol) was combined with pyridine (12.9 ml, 159 mmol) and 4-N,N-dimethylamino-pyridine (0.5 g, 4 mmol) in 100 ml of chloroform. The mixture was stirred as 4'-trifluoromethyl-biphenyl-2-carbonyl chloride (22.64 g, 79.5 mmol) was added as a solution in 100 ml of chloroform. After heating at reflux for 2 h, the mixture was concentrated under vacuum, the residue taken up in ethyl acetate (600 ml) and washed sequentially with a 1 N aqueous hydrochloric acid solution (2×200 ml), water, and brine. The organic phase was then dried over anhydrous magnesium sulfate, filtered and concentrated under vacuum to yield 29.4 g of a red oil. This oil was purified by chromatography on silica, eluting sequentially with a 70:30 dichloromethane/hexanes solution, followed by dichloromethane, then a 10:90 ethyl acetate/dichloromethane solution. Concentration under vacuum of the product containing fractions afforded 13.15 g of the title compound as a yellow solid.

MS (APCI) 465 (M+1)$^+$; 463 (M−1)$^-$ $^1$H NMR (DMSO-d$_6$) 1.35 (t, 3H, J=7.0 Hz), 4.37 (q, 2H, J=7.0 Hz), 7.50–7.73 (m, 9H), 8.09 (d, 1H, J=9.0 Hz), 8.43 (s, 1H), 8.85 (s, 1H), 9.22 (d, 1H, J=1.9 Hz), 10.9 (s, 1H).

Preparation 5

7-[(4'-Trifluoromethyl-biphenyl-2-carbonyl)-amino]-quinoline-3-carboxylic acid

7-[(4'-Trifluoromethyl-biphenyl-2-carbonyl)-amino]-quinoline-3-carboxylic acid ethyl ester (10.28 g, 22.1 mmol) and lithium hydroxide monohydrate (1.86 g, 44.3 mmol) were added to 125 ml of a solution consisting of a 3:1:1 volume ratio of tetrahydrofuran, methanol, and water. After stirring for 3.5 h at ambient temperature, the mixture was concentrated under vacuum to yield an aqueous emulsion of a yellow oil. More water (100 ml) was added and with efficient stirring, the aqueous mixture was made acidic (pH 2) with a 1 N aqueous hydrochloric acid solution. Collection of the resulting solid by vacuum filtration, maintaining the flow of air overnight to dry the solid, and drying under vacuum afforded 9.0 g of the title compound as a yellow powder.

MS (APCI) 437 (M+1)$^+$; 435 (M−1)$^-$ $^1$H NMR (DMSO-d$_6$) 7.50–7.72 (m, 9H), 8.05 (d, 1H, J=9.0 Hz), 8.40 (s, 1H), 8.80 (d, 1H, J=2.1 Hz), 10.85 (s, 1H).

Preparation 6

4'-Trifluoromethyl-biphenyl-2-carboxylic acid (3-amino-4-formyl-phenyl)-amide

To a nitrogen purged 12 liter 3-neck flask fitted with a mechanical stirrer and temperature probe was added THF (4.3 L) and 2,4-diaminobenzaldehyde (50 g, 0.37 mol, 1 equiv). After cooling the solution to −70° C. (dry ice/acetone bath), poly(4-vinylpyridine), which can be obtained form Aldrich, Milwaukee, Wis., 25% cross-linked, (210 g) was added. A solution of 4'-trifluoromethyl-biphenyl-2-carbonyl chloride (105 g, 0.37 mol, 1 equiv) in THF (1 L) was added at such a rate as to maintain the temperature below −60° C. The light orange reaction mixture was allowed to warm to room temperature over 4 hours to give a dark red reaction mixture. (HPLC analysis showed an 18:1 mixture of mono- (retention time (rt)=4.8 min) to di- (rt=3.1 min) acylated products along with 5% residual starting material (rt=18.8 min), (Zorbax SIL (150 mm) from Agilent Technologies, Palo Alto, Calif. 2 mL/min 90:10 hexanes/isopropanol, 0.1% diethylamine, 250 nm, 40° C.). The reaction was quenched with 1 N NaOH (450 mL) and allowed to stir overnight at 25° C. The reaction mixture was filtered and the solids were washed with ethyl acetate (5×200 mL) and the combined organic layers were concentrated in vacuo to give a brown oil. The oil was dissolved in $CH_2Cl_2$ (1.5 L) and silica gel (EM Science, Gibbstown, N.J., 230–400 mesh or 0.04–0.06 mm particle size) (410 g) and Darco G-60® (10 g, BNL Fine Chemicals and Reagents) were added. The slurry was stirred for 15 minutes and filtered. The silica was washed with $CH_2Cl_2$ (5×200 mL). The combined organic layers were concentrated in vacuo and the methylene chloride was displaced with 1:1 hexanes/diisopropylether. The precipitated product was collected by suction filtration and dried in air to give 4'-trifluoromethyl-biphenyl-2-carboxylic acid (3-amino-4-formyl-phenyl)-amide (40 g, 30%, 43:1 mono-:bis acylated by HPLC) as a light yellow solid.
MS (APCI) 385 (M+1)$^+$; 383 (M-1)$^-$
$^1$H NMR (DMSO-d$_6$) δ6.65 (dd, 1H, J=1.7, 8.7 Hz), 7.15 (br s, 2H), 7.25 (s, 1H), 7.38 (d, 1H, J=8.7 Hz), 7.46–7.68 (m, 6H), 7.74 (d, 2H, J=8.3 Hz), 9.57 (s, 1H), 10.51 (s, 1H).

Preparation 7

2-Methyl-7-[(4'-trifluoromethyl-biphenyl-2-carbonyl)-amino]-quinoline-3-carboxylic acid ethyl ester 4'-Trifluoromethyl-biphenyl-2-carboxylic acid (3-amino-4-formyl-phenyl)-amide (769 mg, 2.0 mmol) and ethyl acetoacetate (260 mg, 2.0 mmol) were dissolved in 10 ml of acetic acid and heated at 80 C. After 2.5 h, the mixture was cooled to room temperature, diluted with water and brought to pH 10 with 2N NaOH. The mixture was extracted with ethyl acetate (2×50 ml), the combined organic layers washed with brine, dried over magnesium sulfate, and concentrated to give 815 mg of a yellow solid. This material was purified by chromatography on silica gel eluting with 0 to 10% ethyl acetate in dichloromethane to provide 349 mg (36%) of the title compound as a yellow foam.
MS (APCI) 479(M+1)$^+$,477(M-1)$^-$ Preparation 8

2-Methyl-7-[(4'-trifluoromethyl-biphenyl-2-carbonyl)-amino]-quinoline-3-carboxylic acid 2-Methyl-7-[(4'-trifluoromethyl-biphenyl-2-carbonyl)-amino]-quinoline-3-carboxylic acid ethyl ester (345 mg, 0.72 mmol) was dissolved in 3 ml of tetrahydrofuran, 1 ml of methanol and 1 ml of water, and lithium hydroxide monohydrate was added (61 mg, 1.44 mmol). After 3 h at room temperature, the volatiles were evaporated and the resulting mixture diluted with 10 ml of water before being brought to pH 1 with 1N HCl. Filtration of the resulting solid followed by air drying afforded 326 mg of the title compound as a yellow solid.
MS (APCI) 451(M+1)$^+$,449(M-1)$^-$ Preparation 9

2-(5-Trifluoromethyl-pyridin-2-yl)-benzoic acid isopropyl ester 2-(Isopropylcarboxy)-phenylboronic acid (S. Caron and J. M. Hawkins, J. Org. Chem. 1998, 63, 2054–2055) (2.2 g, 10.6 mmol) and 2-chloro-5-trifluoromethylpyridine (500 mg, 2.75 mmol) were dissolved in toluene. Tetrakis (triphenylphosphine)palladium (160 mg, 0.14 mmol) was added and the reaction vessel purged by alternating vacuum and nitrogen gas three times. 8 ml of a 10% sodium carbonate solution was added and the reaction mixture was heated at reflux for 1.5 h. The resulting mixture was extracted with ethyl acetate, the combined organic layers dried (magnesium sulfate), filtered and concentrated under vacuum. Purification of the residue by column chromatography eluting with 10% ethyl acetate in hexanes provided the title compound in approximately 70% yield.
MS (APCI) 310(M+1)$^+$ Preparation 10

2-(5-Trifluoromethyl-pyridin-2-yl)-benzoic acid 2-(5-Trifluoromethyl-pyridin-2-yl)-benzoic acid isopropyl ester was dissolved in 10 ml of a 3:1:1 mixture of tetrahydrofuran-methanol-water, and lithium hydroxide monohydrate (161 mg, 3.84 mmol) was added. After stirring for 3 h at room temperature, the volatiles were removed under vacuum and 5 ml of water were added to the mixture, which was brought to pH 6 with 1N HCl. The resulting slurry was extracted with ethyl acetate, the combined organic layers were dried (magnesium sulfate), filtered and concentrated under vacuum to provide the title compound.
MS (APCI) 268(M+1)$^+$,266(M-1)$^-$ Preparation 11

7-[2-(5-Trifluoromethyl-pyridin-2-yl)-benzoylamino]-quinoline-3-carboxylic acid ethyl ester 2-(5-Trifluoromethyl-pyridin-2-yl)-benzoic acid (325 mg, 1.05 mmol) was dissolved in 15 ml of thionyl chloride, and the mixture heated at 60 C. After 4 h, the volatiles were removed under vacuum, the residue combined with 7-amino-quinoline-3-carboxylic acid ethyl ester (100 mg, 0.46 mmol), dissolved in 1,2-dichloroethane (15 ml), and diisopropylethylamine (300 mg, 2.31 mmol) added. After heating at reflux for 48 h, the reaction mixture was washed with 1N HCl, dried (magnesium sulfate), filtered, and concentrated under vacuum. The resulting residue was purified by silica gel chromatography eluting with 50% ethyl acetate in hexanes to provide 180 mg (85%) of the title compound.
MS (APCI) 466(M+1)$^+$,464(M-1)$^-$ Preparation 11B 7-[2-(5-Trifluoromethyl-pyridin-2-yl)-benzoylamino]-quinoline-3-carboxylic acid 7-[2-(5-Trifluoromethyl-pyridin-2-yl)-benzoylamino]-quinoline-3-carboxylic acid ethyl ester (180 mg, 0.387 mmol) was dissolved in 5 ml of a 3:1:1 mixture of tetrahydrofuran-methanol-water, and lithium hydroxide monohydrate (50 mg, 1.16 mmol) was added. After 18 h at reflux, the volatiles were removed under vacuum and water was added to the mixture, which was acidified with 1N HCl, extracted with ethyl acetate. The combined organic layers were dried (magnesium sulfate), filtered and concentrated under vacuum to provide the title compound.
MS (APCI) 438(M+1)$^+$,436(M-1)$^-$ Preparation 12

2-(4-Trifluoromethyl-phenyl)-nicotinic acid ethyl ester

Ethyl 2-chloro-nicotinate (1.86 g, 10.0 mmol)was dissolved in 10 ml of dimethoxyethane. Tetrakis (triphenylphosphine)palladium (347 mg, 0.3 mmol) was added and the reaction vessel purged by alternating vacuum and nitrogen gas three times. A solution of 4-trifluoromethylphenylboronic acid (2.09 g, 11.0 mmol) in 20 ml of dimethoxyethane was added to the reaction mixture followed by 10 ml of a 2M sodium carbonate solution. The reaction mixture was heated at 90 C. for 1.5 h before being cooled and extracted with 150 ml of ether. The organic layer was washed with 50 ml of 2N NaOH, 2×50 ml water, and brine before being dried (magnesium sulfate), filtered and concentrated under vacuum to afford 3.24 g of a brown oil. This material was purified by silica gel chromatography eluting with 5 to 10% ethyl acetate in hexanes to afford 2.34 g of the title compound as a pale yellow oil.

MS (APCI) 296(M+1)$^+$

Preparation 13

2-(4-Trifluoromethyl-phenyl)-nicotinic acid 2-(4-Trifluoromethyl-phenyl)-nicotinic acid ethyl ester (2.33 g, 7.9 mmol) was dissolved in 40 ml of a 3:1:1 mixture of tetrahydrofuran-methanol-water, and lithium hydroxide monohydrate (828 mg, 19.8 mmol) was added. After stirring overnight at room temperature, the volatiles were removed under vacuum and 75 ml of water was added to the mixture, which was brought to pH 2 with 1N HCl. The resulting slurry was extracted with 2×100 ml of ethyl acetate, the combined organic layers were washed with brine, dried (magnesium sulfate), filtered and concentrated under vacuum to provide 2.15 g of the title compound as a colorless solid.

MS (APCI) 268(M+1)$^+$,269(M−1)$^-$

Preparation 14

7-{[2-(4-Trifluoromethyl-phenyl)-pyridine-3-carbonyl]-amino}-quinoline-3-carboxylic acid ethyl ester 2-(4-Trifluoromethyl-phenyl)-nicotinic acid (534 mg, 2.0 mmol) was suspended in 10 ml of dichloromethane, and oxalyl chloride (0.7 ml, 8.0 mmol) was added followed by a drop of dimethylformamide. After 2 h at room temperature, the volatiles were removed under vacuum, and to the residue was added 10 ml of chloroform, 7-amino-quinoline-3-carboxylic acid ethyl ester (216 mg, 1.0 mmol), pyridine (0.2 ml, 2.5 mmol) and 4-dimethylaminopyridine (12 mg, 0.1 mmol). After heating at reflux overnight, the reaction mixture was diluted with 50 ml of dichloromethane, washed with 35 ml of 2N NaOH, water, dried (magnesium sulfate) filtered, and concentrated under vacuum to afford 570 mg of a brown gum. This material was purified by silica gel chromatography eluting with 50 to 80% ethyl acetate in hexanes to provide 189 mg of the title compound as a light yellow solid.

MS (APCI) 466(M+1)$^+$,464(M−1)$^-$

Preparation 15

7-{[2-(4-Trifluoromethyl-phenyl)-pyridine-3-carbonyl]-amino}-quinoline-3-carboxylic acid 7-{[2-(4-Trifluoromethyl-phenyl)-pyridine-3-carbonyl]-amino}-quinoline-3-carboxylic acid ethyl ester (160 mg, 0.34 mmol) was dissolved in 5 ml of a 3:1:1 mixture of tetrahydrofuran-methanol-water, and lithium hydroxide monohydrate (29 mg, 0.69 mmol) was added. After 2.5 h at room temperature, the volatiles were removed under vacuum and 5 ml of water was added to the mixture, which was brought to pH 4 with 1N HCl. The resulting slurry was filtered to provide 147 mg of the title compound as a yellow solid.

MS (APCI) 438(M+1)$^+$,436(M−1)$^-$

Preparation 16

7-(2-Bromobenzoylamino)quinoline-3-carboxylic acid ethyl ester

A solution of 2-bromobenzoyl chloride (5.38 g, 24.5 mmol) in 100 ml chloroform was added dropwise at room temperature to a solution of ethyl 7-aminoquinoline-3-carboxylate (2.65 g, 12.25 mmol), 4-N,N-dimethylaminopyridine (150 mg, 1.23 mmol) and pyridine (3.96 ml, 49 mmol) in 100 ml chloroform. The resulting solution was heated under reflux for 4 hr, then cooled to room temperature. The chloroform solution was then washed sequentially with dilute aqueous hydrochloric acid solution, water and brine, dried over anhydrous sodium sulfate and concentrated to dryness in vacuo. The residue was chromatographed on silica gel, eluting with 60:40 hexane/ethyl acetate to yield the title product as a solid foam (2.45 g 50% yield).

MS (M+1)$^+$399.3

The title compound of Preparation 17 was prepared according to a procedure analogous to that described in Preparation 16.

Preparation 17

7-(2-Iodobenzoylamino)quinoline-3-carboxylic acid ethyl ester

55% yield.

MS(M+1)$^+$446.2

Preparation 18

7-[(4'-tert-Butyl-biphenyl-2-carbonyl)-amino]-quinoline-3-carboxylic acid ethyl ester To 5 ml dioxane was added in sequence, 7-(2-bromobenzoylamino)quinoline-3-carboxylic acid ethyl ester (100 mg, 0.25 mmol), potassium carbonate (0.25 ml of 2.0M aqueous solution, 0.5 mmol), 1,1'-bis(diphenylphosphino) ferrocene (6.9 mg, 0.0125 mmol), [1,1'-bis(diphenylphosphino)ferrocene]dichloropalladium(II) complex with dichloromethane (1:1) (10.2 mg, 0.0125 mmol) and 4-tert-butylbenzeneboronic acid (111.5 mg, 0.63 mmol). The resulting mixture was degassed and placed under a nitrogen atmosphere. The degassing procedure was repeated 5 times and the reaction mixture was heated under reflux under nitrogen overnight. The reaction mixture was then cooled to room temperature and poured into water. The aqueous mixture was extracted with ethyl acetate and the ethyl acetate solution was washed with brine, dried over anhydrous sodium sulfate and concentrated to dryness in vacuo. The residue was purified by preparative thick layer chromatography, eluting with 60:40 hexamethyl acetate to yield the title compound (99 mg, 87.3% yield).

MS (M+1)$^+$452.5

Preparation 19

7-[(Biphenyl-2-carbonyl)-amino]-quinoline-3-carboxylic acid ethyl ester

The title compound was prepared according to a procedure analogous to that described in Preparation 18, but using 7-(2-iodobenzoylamino)quinoline-3-carboxylic acid ethyl ester instead of 7-(2-bromobenzoylamino)quinoline-3-carboxylic acid ethyl ester.

38% yield.
MS (M+1)⁺396.4

The title compounds of Preparations 20–36 were prepared according to procedures analogous to that described in Preparation 19.

Preparation 20

7-[(4'-methyl-biphenyl-2-carbonyl)-amino]-quinoline-3-carboxylic acid ethyl ester 57% yield.
MS (M+1)⁺410.5

Preparation 21

7-(2-Benzofuran-2-yl-benzoylamino)-quinoline-3-carboxylic acid ethyl ester

39% yield.
MS (M+1)⁺436.2

The title compounds of Preparations 22–36 were prepared according to procedures analogous to that described in Preparation 18.

Preparation 22

7-[(4'-Isopropyl-biphenyl-2-carbonyl)-amino]-quinoline-3-carboxylic acid ethyl ester 65% yield.
MS (M+1)⁺438.5

Preparation 23

7-[(3'-Methyl-biphenyl-2-carbonyl)-amino]-quinoline-3-carboxylic acid ethyl ester 74% yield.
MS (M+1)⁺410.5

Preparation 24

7-[(4'-Ethyl-biphenyl-2-carbonyl)-amino]-quinoline-3-carboxylic acid ethyl ester 91% yield.
MS (M+1)⁺424.5

Preparation 25

7-[(4'-tert-Butyl-biphenyl-2-carbonyl)-amino]-quinoline-3-carboxylic acid ethyl ester 99% yield.
MS (M+1)⁺452.5

Preparation 26

7-[(4'-Ethylsulfanyl-biphenyl-2-carbonyl)-amino]-quinoline-3-carboxylic acid ethyl ester 95% yield.
MS (M+1)⁺456.6

Preparation 27

7-(2-Naphthalen-2-yl-benzoylamino)-quinoline-3-carboxylic acid ethyl ester

72% yield.
MS (M+1)⁺446.1

Preparation 28

7-(2-Benzo[1,3]dioxol-5-yl-benzoylamino)-quinoline-3-carboxylic acid ethyl ester 77% yield.
MS (M+1)⁺440.5

Preparation 29

7-[(3',4'-Dimethyl-biphenyl-2-carbonyl)-amino]-quinoline-3-carboxylic acid ethyl ester 85% yield.
MS (M+1)⁺425.4

Preparation 30

7-[(2'-Methyl-biphenyl-2-carbonyl)-amino]-quinoline-3-carboxylic acid ethyl ester 39% yield.
MS (M+1)⁺411.6

Preparation 31

7-[(3'-Fluoro-4'-methyl-biphenyl-2-carbonyl)-amino]-quinoline-3-carboxylic acid ethyl ester 44% yield.
MS (M+1)⁺429.3

Preparation 32

7-[(4'-Ethoxy-biphenyl-2-carbonyl)-amino]-quinoline-3-carboxylic acid ethyl ester 58% yield.
MS (M+1)⁺441.3

Preparation 33

7-[2-(2,3-Dihydro-benzofuran-5-yl)-benzoylamino]-quinoline-3-carboxylic acid ethyl ester 52% yield.
MS(M+1)⁺439.3

Preparation 34

7-[(4'-Propoxy-biphenyl-2-carbonyl)-amino]-quinoline-3-carboxylic acid ethyl ester 38% yield.
MS(M+1)⁺455.3

Preparation 35

7-[(4'-Butoxy-biphenyl-2-carbonyl)-amino]-quinoline-3-carboxylic acid ethyl ester 29% yield.
MS (M+1)⁺469.4

Preparation 36

7-[(3-Methyl-4-oxo-2-phenyl-4H-chromene-8-carbonyl)-amino]-quinoline-3-carboxylic acid ethyl ester 57% yield.
MS (M+1)⁺478.5

Preparation 37

7-[(4'-tert-Butyl-biphenyl-2-carbonyl)-amino]-quinoline-3-carboxylic acid

Lithium hydroxide (20.0 mg, 0.48 mmol) was added to a mixture of 7-[(4'-tert-butyl-biphenyl-2-carbonyl)-amino]-quinoline-3-carboxylic acid ethyl ester (99 mg, 0.22 mmol) in 6 ml ethanol and 3 ml water. The reaction mixture was heated under reflux for 1.5 hr, then cooled to room temperature. The ethanol was removed in vacuo and aqueous hydrochloric acid solution was added (0.46ml of 0.961M solution, 0.44 mmol) to the resulting aqueous solution. The precipitate that formed was filtered, washed with water and air dried to yield the title compound as a white solid (75.1 mg, 80.8% yield).
MS (M+1)$^+$424.3

The title compounds of Preparations 38–55 were prepared according to procedures analogous to that described in Preparation 37.

Preparation 38

7-[(Biphenyl-2-carbonyl)-amino]-quinoline-3-carboxylic acid

87% yield.
MS (M+1)$^+$368.4

Preparation 39

7-[(4'-Methyl-biphenyl-2-carbonyl)-amino]-quinoline-3-carboxylic acid

69% yield.
MS (M+1)$^+$382.4

Preparation 40

7-(2-Benzofuran-2-yl-benzoylamino)-quinoline-3-carboxylic acid

69% yield.
MS (M+1)$^+$408.4

Preparation 41

7-[(4'-Isopropyl-biphenyl-2-carbonyl)-amino]-quinoline-3-carboxylic acid 88% yield.
MS (M+1)$^+$410.5

Preparation 42

7-[(3'-Methyl-biphenyl-2-carbonyl)-amino]-quinoline-3-carboxylic acid

73% yield.
MS (M+1)$^+$382.4

Preparation 43

7-[(4'-Ethyl-biphenyl-2-carbonyl)-amino]-quinoline-3-carboxylic acid

91% yield.
MS (M+1)$^+$396.5

Preparation 44

7-[(4'-tert-Butyl-biphenyl-2-carbonyl)-amino]-quinoline-3-carboxylic acid 81% yield.
MS (M+1)$^+$424.3

Preparation 45

7-[(4'-Ethylsulfanyl-biphenyl-2-carbonyl)-amino]-quinoline-3-carboxylic acid

95% yield.
MS (M+1)$^+$456.6

Preparation 46

7-(2-Naphthalen-2-yl-benzoylamino)-quinoline-3-carboxylic acid

84% yield.
MS (M+1)$^+$418.5

Preparation 47

7-(2-Benzo[1,3]dioxol-5-yl-benzoylamino)-quinoline-3-carboxylic acid

78% yield.
MS (M+1)$^+$412.7

Preparation 48

7-[(3',4'-Dimethyl-biphenyl-2-carbonyl)-amino]-quinoline-3-carboxylic acid

65% yield.
MS (M+1)$^+$397.2

Preparation 49

7-[(2'-Methyl-biphenyl-2-carbonyl)-amino]-quinoline-3-carboxylic acid

96% yield.
MS (M+1)$^+$383.1

Preparation 50

7-[(3'-Fluoro-4'-methyl-biphenyl-2-carbonyl)-amino]-quinoline-3-carboxylic acid

78% yield.
MS (M+1)$^+$401.2

Preparation 51

7-[(4'-Ethoxy-biphenyl-2-carbonyl)-amino]-quinoline-3-carboxylic acid

76% yield.
MS (M+1)$^+$413.2

Preparation 52

7-[2-(2,3-Dihydro-benzofuran-5-yl)-benzoylamino]-quinoline-3-carboxylic acid

77% yield.
MS(M+1)$^+$411.2

Preparation 53

7-[(4'-Propoxy-biphenyl-2-carbonyl)-amino]-quinoline-3-carboxylic acid

90% yield.
MS (M+1)$^+$427.2

Preparation 54

7-[(4-Butoxy-biphenyl-2-carbonyl)-amino]-quinoline-3-carboxylic acid

93% yield.
MS (M+1)$^+$441.2

Preparation 55

7-[(3-Methyl-4-oxo-2-phenyl-4H-chromene-8-carbonyl)-amino]-quinoline-3-carboxylic acid 89% yield.
MS (M+1)$^+$450.4

Preparation 56

2-Benzyloxy-3-methoxybenzoic acid methyl ester

To a solution of methyl 3-methoxysalicylate (1.0 g, 5.49 mmol) in 5 ml tetrahydrofuran and 5 ml dimethylformamide was added sequentially at room temperature, benzyl alcohol (0.71 ml, 6.86 mmol), triphenylphosphine (2.16 g, 8.23 mmol) and diethyl azodicarboxylate (1.3 ml, 8.23 mmol). The reaction solution was stirred at room temperature overnight, then ethyl acetate was added and the resulting solution was washed sequentially with water and brine. The ethyl acetate solution was dried over anhydrous sodium sulfate and concentrated to dryness in vacuo. The residue was triturated with diethyl ether and filtered to remove triphenylphosphine oxide. The ether solution was concentrated to dryness in vacuo and the residue was purified by column chromatography on silica gel, eluting with 95:5 hexane/ethyl acetate, yielding the title compound as an oil (870 mg 58% yield). MS (M+1)$^+$273.1

The title compounds of Preparations 57–61 were prepared according to procedures analogous to that described in Preparation 56.

Preparation 57

2-Cyclohexylmethoxy-benzoic acid methyl ester

51% yield.
MS (M+1)$^+$248.3

Preparation 58

2-(Bicyclo[2.2.1]hept-2-ylmethoxy)-benzoic acid methyl ester

69% yield.
MS (M+1)$^+$260.3

Preparation 59

2-(Bicyclo[2.2.1]hept-2-ylmethoxy)-3-methoxy-benzoic acid methyl ester

58% yield.
MS (M+1)$^+$290.3

Preparation 60

2-Pentyloxy -benzoic acid methyl ester

37% yield.
MS (M+1)$^+$222.3

Preparation 61

2-Cyclohexylmethoxy-3-methoxy-benzoic acid methyl ester

97% yield.
MS (M+1)$^+$278.3

The title compounds of Preparations 62–66 were prepared according to procedures analogous to that described in Preparation 37.

Preparation 62

2-Cyclohexylmethoxy-benzoic acid

100% yield.
MS (M+1)$^+$234.3

Preparation 63

2-(Bicyclo[2.2.1]hept-2-ylmethoxy)-benzoic acid

91% yield.
MS (M+1)$^+$246.3

Preparation 64

2-(Bicyclo[2.2.1]hept-2-ylmethoxy)-3-methoxy-benzoic acid

88% yield.
MS (M+1)$^+$447.2

Preparation 65

2-Pentyloxy -benzoic acid 99.6% yield.
MS (M+1)$^+$208.3

Preparation 66

2-Cyclohexylmethoxy-3-methoxy-benzoic acid

77% yield.
MS (M+1)$^+$264.3

Preparation 67

7-(2-Cyclohexylmethoxy-benzoylamino)-quinoline-3-carboxylic acid ethyl ester

The title compound was prepared following the procedure of Example 134 but using 2-cyclohexylmethoxybenzoic acid and 7-aminoquinoline-3-carboxylic acid ethyl ester in the place of 2-benzyloxy-3-methoxybenzoic add and 7-amino-quinoline-3-carboxylic acid (di-pyridin-2-yl-methyl)-amide, respectively.

(58% yield).
MS (M+1)$^+$433.2

The title compounds of Preparation 68–71 were prepared according to procedures analogous to that described in Preparation 67.

Preparation 68

7-[2-(Bicyclo[2.2.1]hept-2-ylmethoxy)-benzoylamino]-quinoline-3-carboxylic acid ethyl ester 69% yield.
MS (M+1)$^+$444.2

Preparation 69

7-[2-(Bicyclo[2.2.1]hept-2-ylmethoxy)-3-methoxy-benzoylamino]-quinoline-3-carboxylic acid ethyl ester 88% yield.
MS (M+1)$^+$474.6

Preparation 70

7-(2-Pentyloxy-benzoylamino)-quinoline-3-carboxylic acid ethyl ester

37% yield.
MS (M+1)$^+$406.5

Preparation 71

7-(2-Cyclohexylmethoxy-3-methoxy-benzoylamino)-quinoline-3-carboxylic acid ethyl ester 51% yield.
MS (M+1)$^+$62.5

The title compounds of Preparations 72–77 were prepared according to procedures analogous to that described in Preparation 37.

Preparation 72

7-(2-Cyclohexylmethoxy-benzoylamino)-quinoline-3-carboxylic acid

94% yield.
MS (M+1)$^+$404.4

Preparation 73

7-[2-(Bicyclo[2.2.1]hept-2-ylmethoxy)-benzoylamino]-quinoline-3-carboxylic acid

90% yield.
MS (M+1)$^+$416.5

Preparation 74

7-[2-(Bicyclo[2.2.1]hept-2-ylmethoxy)-3-methoxy-benzoylamino]-quinoline-3-carboxylic acid 96% yield.
MS (M+1)$^+$446.5

Preparation 75

7-(2-Pentyloxy-benzoylamino)-quinoline-3-carboxylic acid 95% yield.

MS (M+1)$^+$378.4

Preparation 76

7-(2-Cyclohexylmethoxy-3-methoxy-benzoylamino)-quinoline-3-carboxylic acid

80% yield.
MS (M+1)$^+$434.5

Preparation 77

7-(3-Methoxy-2-pentyloxy-benzoylamino)-quinoline-3-carboxylic acid

95% yield.
MS (M+1)$^+$409.3

The title compounds of Preparations 78–87 were prepared according to procedures analogous to that described in Preparation 56.

Preparation 78

2-Cyclopentylethoxy-3-methoxy-benzoic acid methyl ester

100% yield.
MS (M+1)$^+$248

Preparation 79

3-Methoxy-2-(4,4,4-trifluoro-butoxy)-benzoic acid methyl ester

90% yield.
MS (M+1)$^+$293.1

Preparation 80

3-Methoxy-2-(3-methyl-butoxy)-benzoic acid methyl ester

69% yield.
MS (M+1)$^+$253.2

Preparation 81

2-Cyclobutylmethoxy-3-methoxy-benzoic acid methyl ester

52% yield.
MS (M+1)$^+$251

Preparation 82

2-Cyclopentylmethoxy-3-methoxy-benzoic acid methyl ester

50% yield.
MS (M+1)$^+$265

Preparation 83

2-Hexyloxy-3-methoxy-benzoic acid methyl ester

73% yield.
MS (M+1)$^+$267

Preparation 84

2-Cyclohexylethoxy-3-methyl-benzoic acid methyl ester

19% yield.
MS (M+1)$^+$277

Preparation 85

2-Cyclohexylmethoxy-3-methyl-benzoic acid methyl ester

50% yield.
MS (M+1)$^+$263.3

Preparation 86

3-Chloro-2-cyclohexylmethoxy-benzoic acid methyl ester

16% yield.
MS (M+1)$^+$283

Example 87

2-Benzyloxy-3-methoxy-benzoic acid methyl ester

58% yield.
MS (M+1)⁺273.1

The title compounds of Preparations 88–97 were prepared according to procedures analogous to that described in Preparation 37.

Preparation 88

2-Cyclopentylethoxy-3-methoxy-benzoic acid

94% yield
MS (M+1)⁺279.2

Preparation 89

3-Methoxy-2-(4,4,4-trifluoro-butoxy)-benzoic acid

97% yield.
MS (M+1)⁺279.1

Preparation 90

3-Methoxy-2-(3-methyl-butoxy)-benzoic acid

100% yield.
MS (M+1)⁺239.1

Preparation 91

2-Cyclobutylmethoxy-3-methoxy-benzoic acid

99% yield.
MS (M+1)⁺236.2

Preparation 92

2-Cyclopentylmethoxy-3-methoxy-benzoic acid

99% yield.
MS (M+1)⁺250.2

Preparation 93

2-Hexyloxy-3-methoxy-benzoic acid

73% yield.
MS (M+1)⁺252.2

Preparation 94

2-Cyclohexylethoxy-3-methyl-benzoic acid

99% yield.
MS (M+1)⁺262.2

Preparation 95

2-Cyclohexylmethoxy-3-methyl-benzoic acid

79% yield.
MS (M+1)⁺248.5

Preparation 96

3-Chloro-2-cyclohexylmethoxy-benzoic acid

89% yield.
MS (M+1)⁺283

Preparation 97

2-Benzyloxy-3-methoxy-benzoic acid

78% yield.
MS (M+1)⁺258.2

Example 1

7-[(4'-Trifluoromethyl-biphenyl-2-carbonyl)-amino]-quinoline-3-carboxylic acid (dipyridin-2-yl-methyl)-amide 7-[(4'-Trifluoromethyl-biphenyl-2-carbonyl)-amino]-quinoline-3-carboxylic acid (250 mg, 0.57 mmol) was combined with di-(2-pyridyl)-methylamine hydrochloride (126 mg, 0.57 mmol), 1-(3-dimethylaminopropyl)-3-ethylcarbodiimide hydrochloride (121 mg, 0.69 mmol), 1-hydroxybenzotriazole (85 mg, 0.63 mmol), and triethylamine (0.32 ml, 2.3 mmol) in 3 ml of dichloromethane. After stirring overnight at ambient temperature, the reaction mixture was diluted with 75 ml of dichloromethane, and the organic phase washed sequentially with water (2×40 ml), and brine, and then dried over anhydrous magnesium sulfate, filtered and concentrated under vacuum to provide a yellow residue. This material was purified by preparative thin-layer-chromatography on silica eluting with 3% methanol in dichloromethane. The product containing band was collected and eluted with 5% methanol in ethyl acetate to afford 112 mg of the title compound as a colorless solid.

MS (APCI) 604 (M+1)⁺; 602 (M−1)⁻

$^1$H NMR (DMSO-d$_6$) 6.48 (d, 1H, J=7.9 Hz), 7.26 (ddd, 2H, J=7.5, 4.8, 1.0 Hz), 7.53–7.72 (m, 11H), 7.76 (td, 2H, J=7.7, 1.7 Hz), 7.98 (d, 1H, J=8.9 Hz), 8.39 1H, J=1.5 Hz),8.49(ddd, 2H, J=4.8, 1.9, 0.9 Hz), 8.84 (d, 1H, J=2.0 Hz),9.22(d, 1H, J=2.0 Hz), 9.53 (d, 1H, J=7.9 Hz), 10.8 (s, 1H).

Example 1A

7-[(4'-Trifluoromethyl-biphenyl-2-carbonyl)-amino]-quinoline-3-carboxylic acid (dipyridin-2-yl-methyl)-amide, ethanesulfonate Trifluoromethyl-biphenyl-2-carbonyl)-amino]-quinoline-3-carboxylic acid (dipyridin-2-yl-methyl)-amide (112 mg, 0.185 mmol) was dissolved in 5 ml of ethyl acetate, and ethanesulfonic acid (20 mg, 1 equivalent) was added as a solution in 1 ml of diethyl ether. After 30 min, the mixture was concentrated under vacuum to afford 120 mg of the title compound as a light yellow solid.

MS (APCI) 604 (M+1)⁺; 602 (M−1)⁻

$^1$H NMR (DMSO-d$_6$) 1.05 (t, 3H, J=7.3 Hz), 2.38 (q, 2H, J=7.3 Hz), 6.67 (d, 1H 7.3 Hz), 7.48–7.79 (m, 13H), 8.02 (td, 2H, J=7.8, 1.7 Hz), 8.13 (d, 1H, J=8.9 H 8.58 (s, 1H), 8.64 (dd, 2H, J=5.0, 1.0 Hz), 9.09 (s, 1H), 9.37 (d, 1H, J=2.3 Hz), 9.84 (d, 1H, J=7.6 Hz), 11.05 (s, 1H).

Example 1B

7-[(4'-Trifluoromethyl-biphenyl-2-carbonyl)-amino]-quinoline-3-carboxylic acid (dipyridin-2-yl methyl)-amide, bis-ethanesulfonate 7-[(4'-Trifluoromethyl-biphenyl-2-carbonyl)-amino]-quinoline-3-carboxylic acid (dipyridin-2-yl-methyl)-amide (140 mg, 0.232 mmol) was dissolved in 10 ml of ethyl acetate, and ethanesulfonic acid (25 mg, 2 equivalents) was added as a solution in 1.5 ml of diethyl ether. After 15 min, 5 ml more of diethyl ether was added. After stirring for another hour, the mixture was vacuum filtered to afford 85 mg of the title compound as a light yellow solid.

MS (APCI) 604 (M+1)$^+$; 602 (M−1)$^-$ $^1$H NMR (DMSO-d$_6$) 1.05 (t, 6H, J=7.4 Hz), 2.40 (q, 4H, J=7.4 Hz), 6.72 (d, 1H, 7.2 Hz), 7.55–7.84 (m, 13H), 8.11 (td, 2H, J=7.9, 1.7 Hz), 8.19 (d, 1H, J=8.9 Hz), 8.65–8.69 (m, 3H), 9.20 (s, 1H), 9.42 (d, 1H, J=2.0 Hz), 9.97 (d, 1H, J=7.2 Hz), 11.15 (s, 1H).

Example 2

7-[(4'-Trifluoromethyl-biphenyl-2-carbonyl)-amino]-quinoline-3-carboxylic acid (phenyl-pyridin-2-yl-methyl)-amide 7-[(4'-Trifluoromethyl-biphenyl-2-carbonyl)-amino]-quinoline-3-carboxylic acid (100 mg, 0.23 mmol) was combined with phenyl-(2-pyridyl)-methylamine (42 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water (2×20 ml), and brine, and then dried over anhydrous magnesium sulfate, filtered and concentrated under vacuum to provide a yellow residue. This material was purified by preparative thin-layer-chromatography on silica eluting with ethyl acetate. The product containing band was collected and eluted with 5% methanol in ethyl acetate to afford 63 mg of the title compound as a colorless solid.

MS (APCI) 603 (M+1)$^+$; 601 (M−1)$^-$ $^1$H NMR (DMSO-d$_6$) 6.48 (d, 1H, J=7.9 Hz), 7.25–7.38 (m, 4H), 7.44 (d, 2H, J=7.2 Hz) 7.55–7.85 (m, 11H), 8.02 (d, 1H, J=9.2 Hz), 8.43 (s, 1H), 8.56 (d, 1H, J=4.6 Hz), 8.85 (d, 1H, J=1.7 Hz), 9.25 (d, 1H, J=2.3 Hz), 9.56 (d, 1H, J=8.2 Hz), 10.85 (s, 1H).

Example 2A

7-[(4'-Trifluoromethyl-biphenyl-2-carbonyl)-amino]-quinoline-3-carboxylic acid (phenyl-pyridin-2-yl-methyl)-amide, ethanesulfonate 7-[(4'-Trifluoromethyl-biphenyl-2-carbonyl)-amino]-quinoline-3-carboxylic acid (phenyl-pyridin-2-yl-methyl)-amide (63 mg, 0.105 mmol) was dissolved in 5 ml of ethyl acetate, and ethanesulfonic acid (12 mg, 1 equivalent) was added as a solution in 1 ml of diethyl ether. After 30 min, the mixture was concentrated under vacuum to afford 70 mg of the title compound as a light yellow solid.

MS (APCI) 603 (M+1)$^+$; 601 (M−1)$^-$ $^1$H NMR (DMSO-d$_6$) 1.01 (t, 3H, J=7.3 Hz), 2.37 (q, 2H, J=7.3 Hz), 6.53 (d, 1H, J=7.3 Hz), 7.28–7.79 (m, 16H), 8.07 (t, 1H, J=7.7 Hz), 8.18 (d, 1H, J=9.0 Hz), 8.65–8.66 (m, 2H), 9.20 (s, 1H), 9.40 (s, 1H), 9.80 (d, 1H), 11.15 (s, 1H).

Example 2B (S)-7-[(4'-Trifluoromethyl-biphenyl-2-carbonyl)-amino]-quinoline-3-carboxylic acid (phenyl-pyridin-2-yl-methyl)-amide (S)-7-[(4'-Trifluoromethyl-2-carbonyl)-amino]-quinoline-3-carboxylic acid (100 mg, 0.23 mmol) was combined with (S)-phenyl-(2-pyridyl)-methylamine (64 mg, 0.35 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water (2×20 ml), and brine, and then dried over anhydrous magnesium sulfate, filtered and concentrated under vacuum to provide a yellow residue. This material was purified by preparative thin-layer-chromatography on silica eluting with ethyl acetate. The product containing band was collected and eluted with 5% methanol in ethyl acetate to afford 86 mg of the title compound as a colorless solid. Optical Rotation: $[\alpha]_D$=+44.1° (c=0.39 mg/ml; CH$_3$OH)

MS (APCI) 603 (M+1)$^+$; 601 (M−1)$^-$ $^1$H NMR (DMSO-d$_6$) 6.48 (d, 1H, J=7.9 Hz), 7.25–7.38 (m, 4H), 7.44 (d, 2H, J=7.2 Hz) 7.55–7.85 (m, 11H), 8.02 (d, 1H, J=9.2 Hz), 8.43 (s, 1H), 8.56 (d, 1H, Hz), 8.85 (d, 1H, J=1.7 Hz), 9.25 (d, 1H, J=2.3 Hz), 9.56 (d, 1H, J=8.2 Hz), 10.85 (s, 1H).

Example 2C (S)-7-[(4'-Trifluoromethyl-biphenyl-2-carbonyl)-amino]-quinoline-3-carboxylic acid (phenyl-pyridin-2-yl-methyl)-amide, ethanesulfonate (S)-7-[(4'-Trifluoromethyl-biphenyl-2-carbonyl)-amino]-quinoline-3-carboxylic acid (phenyl-pyridin-2-yl-methyl)-amide (63 mg, 0.105 mmol) was dissolved in 5 ml of ethyl acetate, and ethanesulfonic acid (12 mg, 1 equivalent) was added as a solution in 1 ml of diethyl ether. After 30 min, the mixture was concentrated under vacuum to afford 70 mg of the title compound as a light yellow solid.

MS (APCI) 603 (M+1)$^+$; 601 (M−1)$^-$ $^1$H NMR (DMSO-d$_6$) 6.48 (d, 1H, J=7.9 Hz), 7.25–7.38 (m, 4H), 7.44 (d, 2H, J=7.2 Hz) 7.55–7.85 (m, 11H), 8.02 (d, 1H, J=9.2 Hz), 8.43 (s, 1H), 8.56 (d, 1H, J=4.6 Hz), 8.85 (d, 1H, J=1.7 Hz), 9.25 (d, 1H, J=2.3 Hz), 9.56 (d, 1H, J=8.2 Hz), 10.85 (s, 1H).

Example 2D (S)-7-[(4'-Trifluoromethyl-biphenyl-2-carbonyl)-amino]-quinoline-3-carboxylic acid (phenyl-pyridin-2-yl-methyl)-amide, bis-ethanesulfonate (S)-7-[(4'-Trifluoromethyl-biphenyl-2-carbonyl)-amino]-quinoline-3-carboxylic acid (phenyl-pyridin-2-yl-methyl)-amide (250 mg, 0.415 mmol) was dissolved in 15 ml of ethyl acetate, and ethanesulfonic acid (114 mg, 2.5 equivalents) was added as a solution in 5 ml of ethyl acetate. After 1 h, the mixture was concentrated under vacuum, suspended in 30 ml of diethyl ether, and the slurry vacuum filtered to afford 351 mg of the title compound as a light yellow solid. This material was dissolved in 3 ml of ethanol and then 60 ml of ethyl acetate was added gradually. After stirring overnight, the resulting solid was collected by vacuum filtration to afford 289 mg of the title compound as a colorless solid (mp=158° C.).

MS (APCI) 603 (M+1)$^+$; 601 (M−1)$^-$ $^1$H NMR (DMSO-d$_6$) 1.06 (t, 6H, J=7.3 Hz), 2.43 (q, 4H, J=7.3 Hz), 6.57 (d, 1H, J=7.3 Hz), 7.32–7.83 (m, 16H), 8.16 (t, 1H, J=7.4 Hz), 8.24 (d, 1H, J=9.2 Hz). 8.72–8.74 (m, 2H), 9.29 (s, 1H), 9.46 (d, 1H, J=2.0 Hz), 9.89 (d, 1H, J=7.2 Hz), 11.2 (s, 1H).

Example 2E (R)-7-[(4'-Trifluoromethyl-biphenyl-2-carbonyl)-amino]-quinoline-3-carboxylic acid (phenyl-pyridin-2-yl-methyl)-amide 7-[(4'-Trifluoromethyl-biphenyl-2-carbonyl)-amino]-quinoline-3-carboxylic acid (100 mg, 0.23 mmol) was combined with (R)-phenyl-(2-pyridyl)-methylamine (64 mg, 0.35 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water (2×20 ml), and brine, and then dried over anhydrous magnesium sulfate, filtered and concentrated under vacuum to provide a yellow residue. This material was purified by preparative thin-layer-chromatography on silica eluting with ethyl acetate. The product containing band was collected and eluted with 5% methanol in ethyl acetate to afford 73 mg of the title compound as a colorless solid. Optical Rotation: $[\alpha]_D = -45.0°$ (c=0.40 mg/ml; $CH_3OH$)

MS (APCI) 603 (M+1)$^+$; 601 (M−1)$^−$ $^1$H NMR (DMSO-$d_6$) 6.48 (d, 1H, J=7.9 Hz), 7.25–7.38 (m, 4H), 7.44 (d, 2H, J=7.2 Hz) 7.55–7.85 (m, 11H), 8.02 (d, 1H, J=9.2 Hz), 8.43 (s, 1H), 8.56 (d, 1H, J=4.6 Hz), 8.85 (d, 1H, J=1.7 Hz), 9.25 (d, 1H, J=2.3 Hz), 9.56 (d, 1H, J=8.2 Hz 10.85 (s, 1H).

Example 2F (R)-7-[(4'-Trifluoromethyl-biphenyl-2-carbonyl)-amino]-quinoline-3-carboxylic acid (phenyl-pyridin-2-yl-methyl)-amide, ethanesulfonate (R)-7-[(4'-Trifluoromethyl-biphenyl-2-carbonyl)-amino]-quinoline-3-carboxylic acid (phenyl-pyridin-2-yl-methyl)-amide (63 mg, 0.105 mmol) was dissolved in 5 ml of ethyl acetate, and ethanesulfonic acid (11 mg, 1 equivalent) was added as a solution in 1 ml of diethyl ether. After 30 min, the mixture was concentrated under vacuum to afford 65 mg of the title compound as a light yellow solid.

MS (APCI) 603 (M+1)$^+$; 601 (M−1)$^−$ $^1$H NMR (DMSO-$d_6$) 6.48 (d, 1H, J 7.9 Hz), 7.25–7.38 (m, 4H), 7.44 (d, 2H, J=7.2 Hz) 7.55–7.85 (m, 11H), 8.02 (d, 1H, J=9.2 Hz), 8.43 (s, 1H), 8.56 (d, 1H, J=4.6 Hz), 8.85 (d, 1H, J=1.7 Hz), 9.25 (d, 1H, J=2.3 Hz), 9.56 (d, 1H, J=8.2 Hz), 10.85 (s, 1H).

Example 3

7-[(4'-Trifluoromethyl-biphenyl-2-carbonyl)-amino]-quinoline-3-carboxylic acid (1-carbamoyl-2-phenyl-ethyl)-amide 7-[(4'-Trifluoromethyl-biphenyl-2-carbonyl)-amino]-quinoline-3-carboxylic acid (100 mg, 0.23 mmol) was combined with phenylalaninamide (38 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with ethyl acetate. The product containing band was collected and eluted with 5% methanol in ethyl acetate to afford 47 mg of the title compound.

MS (APCI) 583 (M+1)$^+$; 581 (M−1)$^−$ $^1$H NMR (DMSO-$d_6$) 2.96 (dd, 1H, J=13.1, 11.0 Hz), 3.14 (dd, 1H, J=13.7, 3.7 Hz), 4.64–4.70 (m, 1H), 7.11–7.14 (m, 2H), 7.22 (t, 2H, J=7.7 Hz), 7.33 (d, 2H, J=7.7 Hz), 7.52–7.73 (m, 10H), 7.95 (d, 1H, J=8.9 Hz), 8.37 (s, 1H), 8.64 (s, 1H), 8.82 (d, 1H, J=8.2 Hz), 9.10 (s, 1H), 10.85 (s, 1H).

Example 4

7-[(4'-Trifluoromethyl-biphenyl-2-carbonyl)-amino]-quinoline-3-carboxylic acid (carbamoyl-phenyl-methyl)-amide 7-[(4'-Trifluoromethyl-biphenyl-2-carbonyl)-amino]-quinoline-3-carboxylic acid (100 mg, 0.23 mmol) was combined with phenylglycinamide (34 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with ethyl acetate. The product containing band was collected and eluted with 5% methanol in ethyl acetate to afford 56 mg of the title compound.

MS (APCI) 569 (M+1)$^+$; 567 (M−1)$^−$ $^1$H NMR (DMSO-$d_6$) 5.62 (d, 1H, J=7.9 Hz), 7.21–7.34 (m, 4H), 7.50–7.71 (m, 12H), 7.95 (d, 1H, J=9.1 Hz), 8.36 (s, 1H), 8.79 (d, 1H, J=1.6 Hz), 9.07 (d, 1H, J=8.1 Hz), 9.17 (d, 1H, J=2.3 Hz), 10.85 (s, 1H).

Example 5

7-[(4'-Trifluoromethyl-biphenyl-2-carbonyl)-amino]-quinoline-3-carboxylic acid propylamide 7-[(4'-Trifluoromethyl-biphenyl-2-carbonyl)-amino]-quinoline-3-carboxylic acid (100 mg, 0.23 mmol) was combined with propylamine (0.019 ml, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with a 4:1 ethyl acetate-hexanes mixture. The product containing band was collected and eluted with 5% methanol in ethyl acetate to afford 47 mg of the title compound.

MS (APCI) 478 (M+1)$^+$; 476 (M−1)$^−$ $^1$H NMR (DMSO-$d_6$) 0.87 (t, 3H, J=7.4 Hz), 1.52 (hextet, 2H, J=7.3 Hz), 3.23 (q, 2H, J=7.0 Hz), 7.50–7.71 (m, 9H), 7.94 (d, 1H, J=8.7 Hz), 8.37 (s, 1H), 8.6 (d, 1H, J=1.9 Hz), 8.69 (t, 1H, J=5.5 Hz), 9.15 (d, 1H, J=2.1 Hz), 10.85 (s, 1H).

Example 6

7-[(4'-Trifluoromethyl-biphenyl-2-carbonyl)-amino]-quinoline-3-carboxylic acid (2,2,2-trifluoro-ethyl)-amide

7-[(4'-Trifluoromethyl-biphenyl-2-carbonyl)-amino]-quinoline-3-carboxylic acid (100 mg, 0.23 mmol) was combined with 2,2,2-trifluoroethylamine hydrochloride (31 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was concentrated, the residue was suspended in water, and the solid was collected by vacuum filtration to afford 72 mg of the title compound.

MS (APCI) 518 (M+1)$^+$; 516 (M−1)$^-$ $^1$H NMR (DMSO-d$_6$) 4.17 (dq, 2H, J=9.8, 6.3 Hz), 7.56–7.76 (m, 9H), 8.03 (d, 1H, J=8.9 Hz), 8.44 (d, 1H, J=1.7 Hz), 9.23 (d, 1H, J=2.0 Hz), 9.40 (t, 1H, J=6.3 Hz), 10.85 (s, 1H).

Example 7

7-[(4'-Trifluoromethyl-biphenyl-2-carbonyl)-amino]-quinoline-3-carboxylic acid (1-methyl-1-phenyl-ethyl)-amide

7-[(4'-Trifluoromethyl-biphenyl-2-carbonyl)-amino]-quinoline-3-carboxylic acid (100 mg, 0.23 mmol) was combined with 2-amino-2-phenylpropane (31 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with a 3:1 ethyl acetate-hexanes mixture. The product containing band was collected and eluted with 5% methanol in ethyl acetate to afford 67 mg of the title compound as a colorless solid.

MS (APCI) 554 (M+1)$^+$; 552 (M−1)$^-$ $^1$H NMR (DMSO-d$_6$) 1.66 (s, 1H), 7.13 (m, 1H), 7.25 (m, 2H), 7.37 (d, 2H, J=7.7 Hz), 7.50–7.70 (m, 9H), 7.95 (d, 1H, J=8.7 Hz), 8.36 (s, 1H), 8.69 (s, 1H), 8.72 (s, 1H), 9.10 (s, 1H), 10.85 (s, 1H).

Example 8

7-[(4'-Trifluoromethyl-biphenyl-2-carbonyl)-amino]-quinoline-3-carboxylic acid cyclopentylamide

7-[(4'-Trifluoromethyl-biphenyl-2-carbonyl)-amino]-quinoline-3-carboxylic acid (100 mg, 0.23 mmol) was combined with cyclopentylamine (20 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with a 3:1 ethyl acetate-hexanes mixture. The product containing band was collected and eluted with 5% methanol in ethyl acetate to afford 54 mg of the title compound as a colorless solid.

MS (APCI) 504 (M+1)$^+$; 502 (M−1)$^-$ $^1$H NMR (DMSO-d$_6$) 1.50–1.59 (m, 4H), 1.60–1.75 (m, 2H), 1.80–1.95 (m, 2H), 4.20–4.30 (m, 1H), 7.50–7.71 (m, 9H), 7.94 (d, 1H, J=8.9 Hz), 8.36 (s, 1H), 8.54 (d, 1H, J=7.5 Hz), 8.64 (d, 1H, J=2.1 Hz), 9.14 (d, 1H, J=2.3 Hz), 10.85 (s, 1H).

Example 9

7[(4'-Trifluoromethyl-biphenyl-2-carbonyl)-amino]-quinoline-3-carboxylic acid 1-phenyl-propyl)-amide

7-[(4'-Trifluoromethyl-biphenyl-2-carbonyl)-amino]-quinoline-3-carboxylic acid 100 mg, 0.23 mmol) was combined with 1-phenylpropylamine (31 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was concentrated under vacuum, the residue was suspended in water, and the solid was collected by vacuum filtration. This material was purified by preparative thin-layer-chromatography on silica eluting with a 3:1 ethyl acetate-hexanes mixture. The product containing band was collected and eluted with 5% methanol in ethyl acetate to afford 66 mg of the title compound as a colorless solid.

MS (APCI) 554 (M+1)$^+$; 552 (M−1)$^-$ $^1$H NMR (DMSO-d$_6$) 0.89 (t, 3H, J=7.3 Hz), 1.75–1.85 (m, 2H), 4.92 (td, 1H J=8.7, 6.2 Hz), 7.19 (t, 1H, J=7.3 Hz), 7.29 (t, 2H, J=7.6 Hz), 7.38 (d, 2H, J=7.3 Hz). 7.50–7.75 (m, 8H), 7.97 (d, 1H, J=8.9 Hz), 8.38 (s, 1 H), 8.70 (d, 1H, J=1.9 Hz), 9.00 (d, 1H, J=8.3 Hz), 9.17 (d, 1H, J=2.3 Hz), 10.85 (s, 1H).

Example 10

(R) -7-[(4'-Trifluoromethyl-biphenyl-2-carbonyl)-amino]-quinoline-3-carboxylic acid (1-phenyl-ethyl)-amide, ethanesulfonate

7-[(4'-Trifluoromethyl-biphenyl-2-carbonyl)-amino]-quinoline-3-carboxylic acid (100 mg, 0.23 mmol) was combined with (R)-1-phenylethylamine (28 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was concentrated, the residue was suspended in water, and the solid was collected by vacuum filtration. This material was purified by preparative thin-layer-chromatography on silica eluting with a 3:1 ethyl acetate-hexanes mixture The product containing band was collected and eluted with 5% methanol in ethyl acetate to afford 62 mg of product. This material was dissolved in 5 ml of ethyl acetate, and ethanesulfonic acid (12.5 mg, 1 equivalent) was added as a solution in 1 ml of diethyl ether. After 30 min, the mixture was concentrated under vacuum to afford 68 mg of the title compound as a yellow solid.

MS (APCI) 540 (M+1)$^+$; 538 (M−1)$^-$ $^1$H NMR (DMSO-d$_6$) 1.06 (t, 3H, J=7.4 Hz), 1.53 (d, 3H, J=6.9), 2.40 (q, 2H, J=7.4 Hz), 5.24 (quintet, 1H, J=7.1 Hz), 7.22–7.27 (m, 1H), 7.33–7.38 (m, 2H), 7.45 (d, 2H, J=7.3

Hz), 7.56–7.81 (m, 9H), 8.18 (d, 1H, J=8.9 Hz), 8.65 (s, 1H), 9.11 (s, 1H), 9.25 (d, 1H, J=7.9 Hz), 9.38 (d, 1H, J=2.0 Hz), 11.15 (s, 1H).

Example 11

7-[(4'-Trifluoromethyl-biphenyl-2-carbonyl)-amino]-quinoline-3-carboxylic acid (1-pyridin-2-yl-propyl)-amide 7-[(4'-Trifluoromethyl-biphenyl-2-carbonyl)-amino]-quinoline-3-carboxylic acid (100 mg, 0.23 mmol) was combined with 1-(2-pyridyl)-propylamine (31 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with 4% methanol in dichloromethane. The product containing band was collected and eluted with 5% methanol in ethyl acetate to afford 65 mg of the title compound.

MS (APCI) 555 (M+1)$^+$; 553 (M–1)$^-$ $^1$H NMR (DMSO-$d_6$) 0.91 (t, 3H, J=7.4 Hz), 1.84–1.94 (m, 2H), 5.00–5.03 (m, 1H), 7.22 (ddd, 1H, J=7.5, 4.8, 1.0 Hz), 7.42 (d, 1H, J=7.9 Hz), 7.51–7.74 (m, 10H), 7.97 (d, 1H, J=8.9 Hz), 8.38 (d, 1H, J=1.7 Hz), 8.49 (ddd, 1H, J=4.8, 1.9, 1.0 Hz), 8.75 (d, 1H, J=1.7 Hz), 9.02 (d, 1H, J=8.1 Hz), 9.20 (d, 1H, J=2.3 Hz), 10.82 (s, 1H).

Example 11A (R)-7-[(4'-Trifluoromethyl-biphenyl-2-carbonyl)-amino]-quinoline-3-carboxylic acid (1-pyridin-2-yl-propyl)-amide 7-[(4'-Trifluoromethyl-biphenyl-2-carbonyl)-amino]-quinoline-3-carboxylic acid (100 mg, 0.23 mmol) was combined with (R)-1-(2-pyridyl)-propylamine hydrochloride (40 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to afford 112 mg of the title compound as a light yellow solid. Optical Rotation: $[\alpha]_D$=–66.8° (c=0.40 mg/ml; CH$_3$OH).

MS (APCI) 555 (M+1)$^+$; 553 (M–1)$^-$ $^1$H NMR (DMSO-$d_6$) 0.91 (t, 3H, J=7.4 Hz), 1.84–1.94 (m, 2H), 5.00–5.03 (m, 1H), 7.22 (ddd, 1H, J=7.5, 4.8, 1.0 Hz), 7.42 (d, 1H, J=7.9 Hz), 7.51–7.74 (m, 10H 7.97 (d, 1H, J=8.9 Hz), 8.38 (d, 1H, J=1.7 Hz), 8.49 (ddd, 1H, J=4.8, 1.9, 1.0 Hz) 8.75 (d, 1H, J=1.7 Hz), 9.02 (d, 1H, J=8.1 Hz), 9.20 (d, 1H, J=2.3 Hz), 10.82 (s, 1H).

Example 11B (R)-7-[(4'-Trifluoromethyl-biphenyl-2-carbonyl)-amino]-quinoline-3-carboxylic acid (1-pyridin-2-yl-propyl)-amide, ethanesulfonate (R)-7-[(4'-Trifluoromethyl-biphenyl-2-carbonyl)-amino]-quinoline-3-carboxylic acid (1-pyridin-2-yl-propyl)-amide (99 mg) was dissolved in 5 ml of ethyl acetate, and ethanesulfonic acid (20 mg, 1 equivalent) was added as a solution in 1.5 ml of ethyl acetate. After 30 min, the mixture was concentrated under vacuum to afford 117 mg of the title compound as a yellow solid.

1H NMR (DMSO-$d_6$) 0.98 (t, 3H, J=7.3 Hz), 1.06 (d, 3H, J=7.3 Hz), 1.94–2.04 (m, 2H), 2.39 (q, 2H, J=7.3 Hz), 5.15 (q, 1H, J=7.0 Hz), 7.57–7.81 (m, 11H), 8.11–8.19 (m, 2H), 8.56 (s, 1H), 8.71 (d, 1H, J=4.3 Hz), 9.00 (s, 1H), 9.32–9.35 (m, 2H), 11.02 (s, 1H).

Example 11C (S)-7-[(4'-Trifluoromethyl-biphenyl-2-carbonyl)-amino]-quinoline-3-carboxylic acid (1-pyridin-2-yl-propyl)-amide 7-[(4'-Trifluoromethyl-biphenyl-2-carbonyl)-amino]-quinoline-3-carboxylic acid (150 mg, 0.34 mmol) was combined with (S)-1-(2-pyridyl)-propylamine hydrochloride (59 mg, 0.34 mmol), 1-(3-dimethylaminopropyl)-3-ethylcarbodiimide hydrochloride (79 mg, 0.41 mmol), 1-hydroxybenzotriazole (51 mg, 0.38 mmol), and triethylamine (0.19 ml, 1.37 mmol) in 3 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to afford 175 mg of a colorless solid. This material was purified by column chromatography on silica gel eluting with 60–80% ethyl acetate in hexanes. The product containing fractions were concentrated to obtain 78 mg of the title compound as a colorless solid. Optical Rotation: $[\alpha]_D$=+75.6° (c=0.40 mg/ml; CH$_3$OH).

MS (APCI) 555 (M+1)$^+$; 553 (M–1)$^-$ $^1$H NMR (DMSO-$d_6$) 0.91 (t, 3H, J=7.4 Hz), 1.84–1.94 (m, 2H), 5.00–5.03 (m, 1H), 7.22 (ddd, 1H, J=7.5, 4.8, 1.0 Hz), 7.42 (d, 1H, J=7.9 Hz), 7.51–7.74 (m, 10H), 7.97 (d, 1H, J=8.9 Hz), 8.38 (d, 1H, J=1.7 Hz), 8.49 (ddd, 1H, J=4.8, 1.9, 1.0 Hz), 8.75 (d, 1H, J=1.7 Hz), 9.02 (d, 1H, J=8.1 Hz), 9.20 (d, 1H, J=2.3 Hz), 10.82 (s,1H).

Example 11D (S)-7-[(4'-Trifluoromethyl-biphenyl-2-carbonyl)-amino]-quinoline-3-carboxylic acid (1-pyridin-2-yl-propyl)-amide ethanesulfonate (S)-7-[(4'-Trifluoromethyl-biphenyl-2-carbonyl)-amino]-quinoline-3-carboxylic acid (1-pyridin-2-yl-propyl)-amide (67 mg) was dissolved in 5 ml of ethyl acetate, and ethanesulfonic acid (13 mg, 1 equivalent) was added as a solution in 1.5 ml of ethyl acetate. After 60 min, the mixture was concentrated under vacuum to afford 80 mg of the title compound as a yellow solid.

$^1$H NMR (DMSO-$d_6$) 0.98 (t, 3H, J=7.3 Hz), 1.06 (d, 3H, J=7.3 Hz), 1.94–2.04 (m, 2H), 2.39 (q, 2H, J=7.3 Hz), 5.15 (q, 1H, J=7.0 Hz), 7.57–7.81 (m, 11H), 8.11–8.19 (m, 2H), 8.56 (s, 1H), 8.71 (d, 1H, J=4.3 Hz), 9.00 (s, 1H), 9.32–9.35 (m, 2H), 11.02 (s, 1H).

Example 12

7-[(4'-Trifluoromethyl-biphenyl-2-carbonyl)-amino]-quinoline-3-carboxylic acid (pyridin-2-ylmethyl)-amide, ethanesulfonate 7-[(4'-Trifluoromethyl-biphenyl-2-carbonyl)-amino]-quinoline-3-carboxylic acid (100 mg, 0.23 mmol) was combined with 2-aminomethyl-pyridine (25 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with 4% methanol in dichloromethane. The product containing band was collected and eluted with 5% methanol in ethyl acetate to afford 59 mg of product. This material was dissolved in 5 ml of ethyl acetate, and ethanesulfonic acid (12 mg, 1 equivalent) was added as a solution in 1 ml of diethyl ether. After 30 min, the mixture was concentrated under vacuum to afford 68 mg of the title compound as a yellow solid.

MS (APCI) 527 (M+1)$^+$; 525 (M−1)$^-$ $^1$H NMR (DMSO-d$_6$) 1.00 (t, 3H, J=7.4 Hz), 2.34 (q, 2H, J=7.4 Hz), 4.74 (d, 2H, J=5.2 Hz), 7.51–7.74 (m, 11H), 8.05 (t, 1H, J=9.1 Hz), 8.16 (t, 1H), 8.49 (s, 1H), 8.67 (d, 1H, J=5.0 Hz), 8.90 (s, 1H), 9.29 (s, 1H), 9.57 (s, 1H), 10.95 (s, 1H).

Example 13

7-[(4'-Trifluoromethyl-biphenyl-2-carbonyl)-amino]-quinoline-3-carboxylic acid (2-pyridin-2-yl-ethyl)-amide, ethanesulfonate 7-[(4'-Trifluoromethyl-biphenyl-2-carbonyl)-amino]-quinoline-3-carboxylic acid (100 mg, 0.23 mmol) was combined with 1-amino-2-(2-pyridyl)-ethane (28 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with 4% methanol in dichloromethane. The product containing band was collected and eluted with 5% methanol in ethyl acetate to afford 65 mg of product. This material was dissolved in 5 ml of ethyl acetate, and ethanesulfonic acid (15 mg, 1 equivalent) was added as a solution in 1 ml of diethyl ether. After 30 min, the mixture was concentrated under vacuum to afford 88 mg of the title compound as a yellow solid.

MS (APCI) 541 (M+1)$^+$; 539 (M−1)$^-$ $^1$H NMR (DMSO-d$_6$) 1.02 (t, 3H, J=7.5 Hz), 2.35 (q, 2H, J=7.5 Hz), 3.21 (t, 2H, J=6.2 Hz), 3.72 (m, 2H), 7.52–7.76 (m, 10H), 7.84 (d, 1H, J=8.1 Hz), 7.99 (d, 1H, J=8.7 Hz), 8.31 (t, 1H), 8.44 (s, 1H), 8.68 (s, 1H), 8.75 (d, 1H, J=5.4 Hz), 8.93 (d, 1H, J=5.4 Hz), 9.12 (s, 1H), 9.40 (s, 1H), 9.80 (d, 1H), 10.85 (s, 1H). cl Example 14

7-[(4'-Trifluoromethyl-biphenyl-2-carbonyl)-amino]-quinoline-3-carboxylic acid ethylamide, ethanesulfonate 7-[(4'-Trifluoromethyl-biphenyl-2-carbonyl)-amino]-quinoline-3-carboxylic acid (100 mg, 0.23 mmol) was combined with ethylamine hydrochloride (19 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with ethyl acetate The product containing band was collected and eluted with 5% methanol in ethyl acetate to afford 52 mg of product. This material was dissolved in 5 ml of ethyl acetate, and ethanesulfonic acid (12 mg, 1 equivalent) was added as a solution in 1 ml of diethyl ether. After 30 min, the mixture was concentrated under vacuum to afford 61 mg of the title compound as a yellow solid.

MS (APCI) 464 (M+1)$^+$; 462 (M−1)$^-$ $^1$H NMR (DMSO-d$_6$) 1.06 (t, 3H, J=7.4 Hz), 1.19 (t, 3H, J=7.2 Hz), 2.41 (q, 2H, J=7.4 Hz), 3.38 (qd, 2H, J=7.2, 5.6 Hz), 7.57–7.82 (m, 9H), 8.19 (d, 1H, J=8.9 Hz), 8.67 (s, 1H), 8.93 (t, 1H, J=5.4Hz), 9.10 (s, 1H), 9.37 (d, 1H, J=2.0 Hz), 11.15 (s, 1H).

Example 15

7-[(4'-Trifluoromethyl-biphenyl-2-carbonyl)-amino]-quinoline-3-carboxylic acid butylamide, ethanesulfonate 7-[(4'-Trifluoromethyl-biphenyl-2-carbonyl)-amino]-quinoline-3-carboxylic acid (100 mg, 0.23 mmol) was combined with butylamine (17 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with ethyl acetate. The product containing band was collected and eluted with 5% methanol in ethyl acetate to afford 67 mg of product. This material was dissolved in 5 ml of ethyl acetate, and ethanesulfonic acid (15 mg, 1 equivalent) was added as a solution in 1 ml of diethyl ether. After 30 min, the mixture was concentrated under vacuum to afford 75 mg of the title compound as a yellow solid.

MS (APCI) 492 (M+1)$^+$; 490 (M−1)$^-$ $^1$H NMR (DMSO-d$_6$) 0.90 (t, 3H), 1.05 (t, 3H), 1.35 (tq, 2H), 1.55 (tt, 2H), 2.40 (q, 2H), 3.35 (dt, 2H), 7.55–7.80 (m, 9H), 8.20 (d, 1H), 8.65 (s, 1H), 8.85 (t, 1H), 9.07 (s, 1H), 9.35 (s, 1H), 11.15 (s, 1H).

Example 16

7-[(4'-Trifluoromethyl-biphenyl-2-carbonyl)-amino]-quinoline-3-carboxylic acid (thiophen-2-ylmethyl)-amide, ethanesulfonate 7-[(4'-Trifluoromethyl-biphenyl-2-carbonyl)-amino]-quinoline-3-carboxylic acid (100 mg, 0.23 mmol) was combined with 2-aminomethyl-thiophen (26 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to afford 92 mg of product. This material was dissolved in 10 ml of ethyl acetate, and ethanesulfonic acid (19 mg, 1 equivalent) was added as a solution in 1 ml of diethyl ether. After 30 min, the mixture was concentrated under vacuum to afford 103 mg of the title compound as a yellow solid.

MS (APCI) 532 (M+1)$^+$; 530 (M−1)$^-$ $^1$H NMR (DMSO-d$_6$) 1.06 (t, 3H, J=7.4 Hz), 2.41 (q, 2H, J=7.4 Hz), 4.72 (d, 2H, J=5.6 Hz), 7.10 (dd, 1H, J=3.3, 1.0 Hz), 7.43 (dd, 1H, J=4.9, 1.3 Hz), 7.56–7.83 (m, 9H), 8.17 (d, 1H, J=9.8 Hz), 8.64 (s, 1H), 9.09 (s, 1H), 9.38 (d, 1H, J=2.0), 9.59 (t, 1H, J=5.6 Hz).

Example 17

7-[(4'-Trifluoromethyl-biphenyl-2-carbonyl)-amino]-quinoline-3-carboxylic acid (1-methyl-1-pyridin-2-yl-ethyl)-amide 7-[(4'-Trifluoromethyl-biphenyl-2-carbonyl)-amino]-quinoline-3-carboxylic acid (100 mg, 0.23 mmol) was combined with 2-amino-2-(2-pyridyl)-propane (47 mg, 0.35 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with 4% methanol in dichloromethane. The product containing band was collected and eluted with 5% methanol in ethyl acetate to afford 50 mg of the title compound as a yellow solid.

MS (APCI) 555 (M+1)$^+$; 553 (M−1)$^-$ $^1$H NMR (DMSO-d$_6$) 1.72 (s, 6H), 7.22 (dd, 1H, J=7.3, 4.6 Hz), 7.49 (d, 1H, J=8.2 Hz), 7.58 (t, 1H, J=7.6 Hz), 7.63–7.78 (m, 9H), 8.02 (d, 1H, J=9.2 Hz), 8.42 (s, 1H), 8.51 (d, 1H, J=4.6 Hz), 8.76 (d, 1H, J=2.0 Hz), 8.89 (s, 1H), 9.18 (d, 1H, J=2.0 Hz), 10.90 (s, 1H).

Example 18

(S)-7-[(4'-Trifluoromethyl-biphenyl-2-carbonyl)-amino]-quinoline-3-carboxylic acid (1-pyridin-2-yl-ethyl)-amide 7-[(4'-Trifluoromethyl-biphenyl-2-carbonyl)-amino]-quinoline-3-carboxylic acid (100 mg, 0.23 mmol) was combined with (S)-1-amino-1-(2-pyridyl)-ethane (51 mg, 0.41 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with ethyl acetate. The product containing band was collected and eluted with 5% methanol in ethyl acetate to afford 76 mg of the title compound. Optical Rotation [α]$_D$=+63.90° (c=0.39 mg/ml; CH$_3$OH)

MS (APCI) 541 (M+1)$^+$; 539 (M−1)$^-$ $^1$H NMR (DMSO-d$_6$) 1.52 (d, 3H, J=6.9 Hz), 5.22 (dq, 1H), 7.24 (t, 1H, J=5.9 Hz), 7.43 (d, 1H, J=7.7 Hz), 7.52–7.76 (m, 10H), 7.98 (d, 1H, J=8.6 Hz), 8.40 (s, 1H), 8.51 (d, 1H, J=5.0 Hz), 8.77 (s, 1H), 9.11 (d, 1H, J=7.3 Hz), 9.22 (s, 1H), 10.81 (s, 1H).

Example 18A (R)-7-[(4'-Trifluoromethyl-biphenyl-2-carbonyl)-amino]-quinoline-3-carboxylic acid (1-pyridin-2-yl-ethyl)-amide ethanesulfonate 7-[(4'-Trifluoromethyl-biphenyl-2-carbonyl)-amino]-quinoline-3-carboxylic acid (100 mg, 0.23 mmol) was combined with (R)-1-(2-pyridyl)-ethylamine (50 mg, 0.41 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with ethyl acetate. The product containing band was collected and eluted with 5% methanol in ethyl acetate to afford 50 mg of the title compound as a colorless solid. Optical Rotation: [α]$_D$=−86.3° (c=0.39 mg/ml; CH$_3$H). A portion of this material (40 mg) was dissolved in 5 ml of ethyl acetate, and ethanesulfonic acid (7.5 mg, 1 equivalent) was added as a solution in 1 ml of diethyl ether. After 30 min, the mixture was concentrated under vacuum to afford 38 mg of the title compound as a yellow solid.

MS (APCI) 541 (M+1)$^+$; 539 (M−1)$^-$ $^1$H NMR (DMSO-d$_6$) 1.05 (t, 3H, J=7.4 Hz), 1.62 (d, 3H, J=6.9 Hz), 2.40 (q, 2H, J=7.4 Hz), 5.34 (m, 1H), 7.56–7.87 (m, 11H), 8.14 (d, 1H, J=8.9 Hz), 8.23 (m, 1H), 8.59 (s, 1H), 8.73 (d, 1H, J=4.3 Hz), 9.04 (s, 1H), 9.35 (s, 1H), 9.45 (d, 1H, J=5.9 Hz), 11.03 (s, 1H).

Example 19

7-[(4'-Trifluoromethyl-biphenyl-2-carbonyl)-amino]-quinoline-3-carboxylic acid amide 7-[(4'-Trifluoromethyl-biphenyl-2-carbonyl)-amino]-quinoline-3-carboxylic acid (300 mg, 0.69 mmol) was combined with ammonium chloride (55 mg, 1.04 mmol), 1-(3-dimethylaminopropyl)-3-ethylcarbodiimide hydrochloride (159 mg, 0.83 mmol), 1-hydroxybenzotriazole (103 mg, 0.76 mmol), and triethylamine (0.38 ml, 2.76 mmol) in 5 ml of dichloromethane. After stirring overnight at ambient temperature, the reaction mixture was concentrated, the residue was suspended in water, and the solid was collected by vacuum filtration to afford 219 mg of the title compound as an off-white solid.

MS (APCI) 436 (M+1)$^+$; 434 (M−1)$^-$ $^1$H NMR (DMSO-d$_6$) 7.51–7.72 (m, 10H), 7.93 (d, 1H, J=8.7 Hz), 8.21 (s, 1H) 8.38 (s, 1H), 8.70 (s, 1H), 9.19 (s, 1H), 10.80 (s, 1H).

Example 20

7-[(4'-Trifluoromethyl-biphenyl-2-carbonyl)-amino]-quinoline-3-carboxylic acid benzylamide 7-[(4'-Trifluoromethyl-biphenyl-2-carbonyl)-amino]-quinoline-3-carboxylic acid (40 mg, 0.092 mmol) was combined with benzylamine (15 mg, 0.14 mmol), 1-(3-dimethylaminopropyl)-3-ethylcarbodiimide hydrochloride (21 mg, 0.11 mmol), 1-hydroxybenzotriazole (14 mg, 0.10 mmol), and triethylamine (0.051 ml, 0.37 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with 4% methanol in dichloromethane. The product containing band was collected and eluted with 5% methanol in ethyl acetate to afford 20 mg of the title compound as a colorless solid.

MS (APCI) 526 (M+1)$^+$; 524 (M−1)$^−$ $^1$H NMR (DMSO-d$_6$) 4.55 (d, 2H, J=5.9 Hz), 7.24–7.39 (m, 5H), 7.56–7.77 (m, 9H) 8.00 (d, 1H, J=8.9 Hz), 8.43 (s, 1H), 8.76 (d, 1H, J=2.0 Hz), 9.25 (d, 1H, J=2.3 Hz), 9.34 (t, 1H, J=5.9 Hz), 10.85 (s, 1H).

Example 21

7-[(4'-Trifluoromethyl-biphenyl-2-carbonyl)-amino]-quinoline-3-carboxylic acid 4-methoxy-benzylamide 7-[(4'-Trifluoromethyl-biphenyl-2-carbonyl)-amino]-quinoline-3-carboxylic acid (40 mg, 0.092 mmol) was combined with 4-methoxybenzylamine (15 mg, 0.14 mmol), 1-(3-dimethylaminopropyl)-3-ethylcarbodiimide hydrochloride (21 mg, 0.11 mmol), 1-hydroxybenzotriazole (14 mg, 0.10 mmol), and triethylamine (0.051 ml, 0.37 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with 4% methanol in dichloromethane. The product containing band was collected and eluted with 5% methanol in ethyl acetate to afford 9 mg of the title compound as a colorless solid.

MS (APCI) 556 (M+1)$^+$; 554 (M−1)$^−$ $^1$H NMR (DMSO-d$_6$) 3.73 (s, 3H), 4.47 (d, 2H, J=5.9 Hz), 6.91 (d, 2H, J=8.6 Hz), 7.30 (d, 2H, J=8.6 Hz), 7.56–7.77 (m, 9H), 8.00 (d, 1H, J=8.9 Hz), 8.43 (s, 1H), 8.74 (d, 1H, J=2.0 Hz), 9.24–9.26 (m, 2H), 10.85 (s, 1H).

Example 22

7-[(4'-Trifluoromethyl-biphenyl-2-carbonyl)-amino]-quinoline-3-carboxylic acid 4-chloro-benzylamide 7-[(4'-Trifluoromethyl-biphenyl-2-carbonyl)-amino]-quinoline-3-carboxylic acid (40 mg, 0.092 mmol) was combined with 4-chlorobenzylamine (19 mg, 0.14 mmol), 1-(3-dimethylaminopropyl)-3-ethylcarbodiimide hydrochloride (21 mg, 0.11 mmol), 1-hydroxybenzotriazole (14 mg, 0.10 mmol), and triethylamine (0.051 ml, 0.37 mmol) in 1.5 ml of dichloromethane. After stirring overnight at ambient temperature, the reaction mixture was concentrated, the residue was suspended in water, and the solid was collected by vacuum filtration. This material was then slurried in a 1:1 methanol-dichloromethane solution, and the solid collected by vacuum filtration to afford the title compound as a colorless solid.

MS (APCI) 560 & 562 (M+1)$^+$; 558 & 560 (M−1)$^−$ $^1$H NMR (DMSO-d$_6$) 4.53 (d, 2H, J=5.6 Hz), 7.40 (s, 4H), 7.55–7.77 (m, 9H), 8.00 (d, 1H, J=8.9 Hz), 8.43 (s, 1H), 8.76 (d, 1H, J=1.6 Hz), 9.25 (d, 1H, J=2.0 Hz), 9.36 (t, 1H, J=5.9 Hz), 10.85 (s, 1H).

Example 23

7-[(4'-Trifluoromethyl-biphenyl-2-carbonyl)-amino]-quinoline-3-carboxylic acid 4-methyl-benzylamide 7-[(4'-Trifluoromethyl-biphenyl-2-carbonyl)-amino]-quinoline-3-carboxylic acid (40 mg, 0.092 mmol) was combined with 4-methylbenzylamine (17 mg, 0.14 mmol), 1-(3-dimethylaminopropyl)-3-ethylcarbodiimide hydrochloride (21 mg, 0.11 mmol), 1-hydroxybenzotriazole (14 mg, 0.10 mmol), and triethylamine (0.051 ml, 0.37 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with 4% methanol in dichloromethane. The product containing band was collected and eluted with 5% methanol in ethyl acetate to afford 20 mg of the title compound as a colorless solid.

MS (APCI) 540 (M+1)$^+$; 538 (M−1)$^−$ $^1$H NMR (DMSO-d$_6$) 2.25 (s, 3H), 4.46 (d, 2H, J=5.8 Hz), 7.12 (d, 2H, J=8.0 Hz), 7.22 (d, 2H, J=8.0 Hz), 7.53–7.73 (m, 9H), 7.96 (d, 1H, J=8.9 Hz), 8.40 (s, 1H), 8.72 (d, 1H, J=2.1 Hz), 9.21 (d, 1H, J=2.3 Hz), 9.25 (t, 1H, J=5.9 Hz), 10.82 (s, 1H).

Example 24

7-[(4'-Trifluoromethyl-biphenyl-2-carbonyl)-amino]-quinoline-3-carboxylic acid cyclopropylmethyl-amide 7-[(4'-Trifluoromethyl-biphenyl-2-carbonyl)-amino]-quinoline-3-carboxylic acid (100 mg, 0.23 mmol) was combined with cyclopropylmethylamine (29 mg, 0.27 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to afford 101 mg of the title compound as a colorless solid.

MS (APCI) 490 (M+1)$^+$; 488 (M−1)$^−$ $^1$H NMR (DMSO-d$_6$) 0.24–0.29 (m, 2H), 0.44–0.50 (m, 2H), 1.03–1.09 (m, 1H), 3.21 (t, 2H, J=6.1 Hz), 7.55–7.77 (m, 9H), 8.00 (d, 1H, J=8.9 Hz), 8.43 (d, 1H, J=1.7 Hz), 8.72 (d, 1H, J=2.0 Hz), 8.87 (t, 1H, J=5.6 Hz), 9.22 (d, 1H, J=2.3 Hz), 10.85 (s, 1H).

Example 25

7-[(4'-Trifluoromethyl-biphenyl-2-carbonyl)-amino]-quinoline-3-carboxylic acid 4-fluoro-benzylamide 7-[(4'-Trifluoromethyl-biphenyl-2-carbonyl)-amino]-quinoline-3-carboxylic acid (100 mg, 0.23 mmol) was combined with 4-fluorobenzylamine (34 mg, 0.27 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was concentrated, the residue was suspended in water, and the solid was collected by vacuum filtration to afford 96 mg of the title compound as a colorless solid.

MS (APCI) 544 (M+1)$^+$; 542 (M−1)$^-$ $^1$H NMR (DMSO-d$_6$) 4.53 (d, 2H, J=5.9 Hz), 7.14–7.20 (m, 2H), 7.39–7.44 (m, 2H), 7.55–7.77 (m, 9H), 8.00 (d, 1H, J=8.9 Hz), 8.43 (d, 1H, J=1.6 Hz), 8.76 (d, 1H, J=1.6 Hz), 9.25 (d, 1H, J=2.0 Hz), 9.34 (t, 1H, J=5.9 Hz), 10.85 (s, 1H).

Example 26

7-[(4'-Trifluoromethyl-biphenyl-2-carbonyl)-amino]-quinoline-3-carboxylic acid isopropyl-amide 7-[(4'-Trifluoromethyl-biphenyl-2-carbonyl)-amino]-quinoline-3-carboxylic acid (100 mg, 0.23 mmol) was combined with isopropylamine (16 mg, 0.27 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature the reaction mixture was diluted with 50 ml of dichloromethane, and the organic phase washed sequentially with water, and brine, and then dried over anhydrous magnesium sulfate, filtered and concentrated under vacuum to afford 96 mg of the title compound as a yellow solid.

MS (APCI) 478 (M+1)$^+$; 476 (M−1)$^-$ $^1$H NMR (DMSO-d$_6$) 1.21 (d, 6H, J=6.6 Hz), 4.10–4.20 (m, 1H), 7.56–7.77 (m, 9H), 7.99 (d, 1H, J=9.2 Hz), 8.42 (d, 1H, J=1.7 Hz), 8.54 (d, 1H, J=7.6 Hz), 8.70 (d, 1H, J=1.6 Hz), 9.20 (d, 1H, J=2.0 Hz), 10.85 (s, 1H).

Example 27

7-[(4'-Trifluoromethyl-biphenyl-2-carbonyl)-amino]-quinoline-3-carboxylic acid benzhydryl-amide 7-[(4'-Trifluoromethyl-biphenyl-2-carbonyl)-amino]-quinoline-3-carboxylic acid (100 mg, 0.23 mmol) was combined with aminodiphenylmethane (42 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to provide a residue. This material was purified by preparative thin-layer-chromatography on silica eluting with ethyl acetate. The product containing band was collected and eluted with 5% methanol in ethyl acetate to afford 66 mg of the title compound as a colorless solid.

MS (APCI) 602 (M+1)$^+$; 600 (M−1)$^-$ $^1$H NMR (DMSO-d$_6$) 6.47 (d, 1H, J=8.6 Hz), 7.26–7.43 (m, 10H), 7.56–7.77 (m, 9H), 8.00 (d, 1H, J=8.9 Hz), 8.44 (s, 1H), 8.83 (d, 1H, J=2.0 Hz), 9.25 (d, 1H, J=3.3 Hz), 9.58 (d, 1H, J=8.6 Hz), 10.85 (s, 1H).

Example 28

7-[(4'-Trifluoromethyl-biphenyl-2-carbonyl)-amino]-quinoline-3-carboxylic acid cyclopropylamide 7-[(4-Trifluoromethyl-biphenyl-2-carbonyl)-amino]-quinoline-3-carboxylic acid (100 mg, 0.23 mmol) was combined with cyclopropylamine (20 mg, 0.35 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of dichloromethane, and the organic phase washed sequentially with water, and brine, and then dried over anhydrous magnesium sulfate, filtered and concentrated under vacuum to afford the title compound.

MS (APCI) 476 (M+1)$^+$; 474 (M−1)$^-$ $^1$H NMR (DMSO-d$_6$) 0.57–0.59 (m, 2H), 0.67–0.72 (m, 2H), 2.85–2.88 (m, 1H), 7.51–7.72 (m, 9H), 7.94 (d, 1H, J=8.9 Hz), 8.37 (s, 1H), 8.62 (s, 1H), 8.69 (d, 1H, J=4.2 Hz), 9.13 (s, 1H), 10.80 (s, 1H).

Example 29

7-[(4'-Trifluoromethyl-biphenyl-2-carbonyl)-amino]-quinoline-3-carboxylic acid [1-(4-fluoro-phenyl)-ethyl]-amide 7-[(4'-Trifluoromethyl-biphenyl-2-carbonyl)-amino]-quinoline-3-carboxylic acid (100 mg, 0.23 mmol) was combined with 1-(4-fluorophenyl)-ethylamine (32 mg, 0.23 mmol), 1-(3-dimethylaminopropyl)-3-ethylcarbodiimide hydrochloride (53 mg, 0.27 mmol), 1-hydroxybenzotriazole (34 mg, 0.25 mmol), and triethylamine (0.13 ml, 0.92 mmol) in 1.5 ml of dichloromethane. After stirring overnight at ambient temperature, the reaction mixture was diluted with 50 ml of ethyl acetate, and the organic phase washed sequentially with water, and brine, and then dried over anhydrous magnesium sulfate, filtered and concentrated under vacuum to afford 120 mg of the title compound as a yellow solid.

MS (APCI) 558 (M+1)$^+$; 556 (M−1)$^-$ $^1$H NMR (DMSO-d$_6$) 1.50 (d, 3H, J=6.9 Hz), 5.22 (quintet, 1H, J=6.9), 7.13–7.20 (m, 2H), 7.43–7.52 (m, 2H), 7.55–7.82 (m, 9H), 8.01 (d, 1H, J=9.2 Hz), 8.43 (d, 1H, J=1.6 Hz), 8.75 (d, 1H, J=1.6 Hz), 9.11 (d, 1H, J=7.6 Hz), 9.22 (d, 1H, J=2.3Hz, 10.85 (s, 1H).

Example 30

7-[(4'-Trifluoromethyl-biphenyl-2-carbonyl)-amino]-quinoline-3-carboxylic acid 3-methyl-benzylamide 7-[(4'-Trifluoromethyl-biphenyl-2-carbonyl)-amino]-quinoline-3-carboxylic acid (50 mg, 0.11 mmol) was combined with 3-methylbenzylamine (14 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was diluted with 30 ml of ethyl acetate, and the organic phase washed sequentially with water, and brine, and then dried over anhydrous magnesium sulfate, filtered and concentrated under vacuum to afford 52 mg of the title compound as a colorless solid.

MS (APCI) 540 (M+1)$^+$; 538 (M−1)$^-$ $^1$H NMR (DMSO-d$_6$) 2.29 (s, 3H), 4.51 (d, 2H, J=7.0 Hz), 7.06–7.25 (m, 4H), 7.55–7.77 (m, 9H), 8.00 (d, 1H, J=8.9 Hz), 8.43 (d, 1H, J=2.0 Hz), 8.76 (d, 1H, J=2.0 Hz), 9.25 (d, 1H, J=2.0 Hz), 9.30 (t, 1H, J=5.9 Hz), 10.85 (s, 1H).

Example 31

7-[(4'-Trifluoromethyl-biphenyl-2-carbonyl)-amino]-quinoline-3-carboxylic acid 3-methoxy-benzylamide 7-[(4'-Trifluoromethyl-biphenyl-2-carbonyl)-amino]-quinoline-3-carboxylic acid (50 mg, 0.11 mmol) was combined with 3-methoxybenzylamine (16 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was diluted with 30 ml of ethyl acetate, and the organic phase washed sequentially with water, and brine, and then dried over anhydrous magnesium sulfate, filtered and concentrated under vacuum to afford 53 mg of the title compound as a colorless solid.

MS (APCI) 556 (M+1)$^+$; 554 (M−1)$^−$ $^1$H NMR (DMSO-d$_6$) 3.74 (s, 3H), 4.51 (d, 2H, J=5.6 Hz), 6.83 (dd, 1H, J=7.4, 24 Hz), 6.93–6.95 (m, 2H), 7.26 (t, 1H, J=8.3), 7.55–7.77 (m, 9H), 7.99 (d, 1H, J=8.9 Hz), 8.42 (s, 1H), 8.76 (d, 1H, J=2.3 Hz), 9.25 (d, 1H, J=2.3 Hz), 9.31 (t, 1H, J=5.9), 10.83 (s, 1H).

Example 32

7-[(4'-Trifluoromethyl-biphenyl-2-carbonyl)-amino]-quinoline-3-carboxylic acid 3-chloro-benzylamide 7-[(4'-Trifluoromethyl-biphenyl-2-carbonyl)-amino]-quinoline-3-carboxylic acid (50 mg, 0.11 mmol) was combined with 3-chlorobenzylamine (16 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was diluted with 30 ml of ethyl acetate, and the organic phase washed sequentially with water, and brine, and then dried over anhydrous magnesium sulfate, filtered and concentrated under vacuum to afford 56 mg of the title compound as a colorless solid.

MS (APCI) 560 & 562 (M+1)$^+$; 558 & 560 (M−1)$^−$ $^1$H NMR (DMSO-d$_6$) 4.54 (d, 2H, J=5.9 Hz), 7.30–7.43 (m, 4H), 7.52–7.77 (m, 9H), 8.01 (d, 1H, J=8.9 Hz), 8.43 (d, 1H, J=1.6 Hz), 8.76 (d, 1H, J=2.0 Hz), 9.25 (d, H, J=2.0 Hz), 9.37 (t, 1H, J=6.0 Hz), 10.85 (s, 1H).

Example 33

7-[(4'-Trifluoromethyl-biphenyl-2-carbonyl)-amino]-quinoline-3-carboxylic acid 2-fluoro-benzylamide 7-[(4'-Trifluoromethyl-biphenyl-2-carbonyl)-amino]-quinoline-3-carboxylic acid (50 mg, 0.11 mmol) was combined with 2-fluorobenzylamine (14mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was diluted with 30 ml of ethyl acetate, and the organic phase washed sequentially with water, and brine, and then dried over anhydrous magnesium sulfate, filtered and concentrated under vacuum to afford 48 mg of the title compound as a colorless solid.

MS (APCI) 544 (M+1)$^+$; 542 (M−1)$^{31}$ $^1$H NMR (DMSO-d$_6$) 4.58 (d, 2H, J=5.6 Hz), 7.16–7.23 (m, 2H), 7.29–7.36 (m, 1H) 7.42–7.47 (m, 1H), 7.55–7.77 (m, 9H), 7.99 (d, 1H, J=8.8 Hz), 8.43 (s, 1H), 8.76 (d, 1H, J=2.3 Hz), 9.25 (d, 1H, J=2.3 Hz), 9.31 (t, 1H, J=5.6 Hz), 10.85 (s, 1H).

Example 34

7-[(4'-Trifluoromethyl-biphenyl-2-carbonyl)-amino]-quinoline-3-carboxylic acid 3-fluoro-benzylamide 7-[(4'-Trifluoromethyl-biphenyl-2-carbonyl)-amino]-quinoline-3-carboxylic acid (50 mg, 0.11 mmol) was combined with 3-fluorobenzylamine (14 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was diluted with 30 ml of ethyl acetate, and the organic phase washed sequentially with water, and brine, and then dried over anhydrous magnesium sulfate, filtered and concentrated under vacuum to afford 49 mg of the title compound as a colorless solid.

MS (APCI) 544 (M+1)$^+$; 542 (M−1)$^−$ $^1$H NMR (DMSO-d$_6$) 4.55 (d, 2H, J=5.9 Hz), 7.08 (td, 1H, J=8.3, 2.3 Hz), 7.17–7.23 m, 2H), 7.35–7.43 (m, 1H), 7.55–7.77 (m, 9H), 8.00 (d, 1H, J=8.9 Hz), 8.43 (s, 1H), 8.77 (d, 1H, J=2.0 Hz), 9.25 (d, 1H, J=2.0 Hz), 9.36 (t, 1H, J=5.9 Hz), 10.85 (s, 1H).

Example 35

7-[(4'-Trifluoromethyl-biphenyl-2-carbonyl)-amino]-quinoline-3-carboxylic acid 2-methyl-benzylamide 7-[(4'-Trifluoromethyl-biphenyl-2-carbonyl)-amino]-quinoline-3-carboxylic acid (50 mg, 0.11 mmol) was combined with 2-methylbenzylamine (14 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was concentrated, the residue was suspended in water, and the solid was collected by vacuum filtration to afford 50 mg of the title compound as a colorless solid.

MS (APCI) 540 (M+1)$^+$; 538 (M−1)$^−$ $^1$H NMR (DMSO-d$_6$) 2.35 (s, 3H), 4.52 (d, 2H, J=5.6 Hz), 7.15–7.20 (m, 3H), 7.29–7.32 (m, 1H), 7.55–7.77 (m, 9H), 7.99 (d, 1H, J=8.9 Hz), 8.43 (s, 1H), 8.77 (d, 1H, J=2.0 Hz), 9.18 (t, 1H, J=5.9 Hz), 9.25 (d, 1H, J=2.3 Hz), 10.83 (s, 1H).

Example 36

7-[(4'-Trifluoromethyl-biphenyl-2-carbonyl)-amino]-quinoline-3-carboxylic acid 2-methoxy-benzylamide 7-[(4'-Trifluoromethyl-biphenyl-2-carbonyl)-amino]-quinoline-3-carboxylic acid (50 mg, 0.11 mmol) was combined with 2-methoxybenzylamine (16 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was diluted with 30 ml of ethyl acetate, and the organic phase washed sequentially with water, and brine, and then dried over anhydrous magnesium sulfate, filtered and concentrated under vacuum to afford 46 mg of the title compound as a colorless solid.

MS (APCI) 556 (M+1)$^+$; 554 (M−1)$^−$ $^1$H NMR (DMSO-d$_6$) 3.84 (s, 3H), 4.51 (d, 2H, J=5.6 Hz), 6.92 (td, 1H, J=7.6, 1.0 Hz), 7.01 (d, 1H, J=7.6 Hz), 7.23–7.27 (m, 2H), 7.55–7.77 (m, 9H), 8.00 (d, 1H, J=8.9 Hz), 8.43 (d, 1H, J=1.6 Hz), 8.78 (d, 1H, J=2.0 Hz), 9.14 (t, 1H, J=5.8 Hz), 9.26 (d, 1H, J=2.3 Hz), 10.85 (s, 1H).

Example 37

7-[(4'-Trifluoromethyl-biphenyl-2-carbonyl)-amino]-quinoline-3-carboxylic acid 2-chloro-benzylamide 7-[(4'-Trifluoromethyl-biphenyl-2-carbonyl)-amino]-quinoline-3-carboxylic acid (50 mg, 0.11 mmol) was combined with 2-chlorobenzylamine (16 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was concentrated, the residue was suspended in water, and the solid was collected by vacuum filtration to afford 48 mg of the title compound as a colorless solid.

MS (APCI) 558 & 560 (M−1)−

$^1$H NMR (DMSO-d$_6$) 4.58 (d, 2H, J=5.6 Hz), 7.27–7.37 (m, 2H), 7.41–7.46 (m, 2H 7.53–7.74 (m, 9H), 7.99 (d, 1H, J=8.9 Hz), 8.41 (s, 1H), 8.77 (s, 1H), 9.24 (d, 1H, J=1.9 Hz), 9.31 (t, 1H, J=5.6 Hz), 10.83 (s, 1H).

Example 38

4'-Trifluoromethyl-biphenyl-2-carboxylic acid [3-(pyrrolidine-1-carbonyl)-quinolin-7-yl]-amide 7-[(4'-Trifluoromethyl-biphenyl-2-carbonyl)-amino]-quinoline-3-carboxylic acid (50 mg, 0.11 mmol) was combined with pyrrolidine (9 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane and allowed to react overnight. The reaction mixture was concentrated, the residue was suspended in water, and the solid was collected by vacuum filtration. This material was purified by preparative thin-layer-chromatography on silica eluting with ethyl acetate. The product containing band was collected and eluted with 5% methanol in ethyl acetate to afford 26 mg of the title compound as a colorless solid.

MS (APCI) 490 (M+1)+; 488 (M−1)−

$^1$H NMR (DMSO-d$_6$) 1.82–1.92 (m, 4H), 3.52 (t, 4H, J=6.3 Hz), 7.55–7.77 (m, 9H), 7.94 (d, 1H, J=8.9 Hz), 8.40 (s, 1H), 8.47 (d, 1H, J=1.7 Hz), 8.93 (d, 1H, J=1.3 Hz), 10.80 (s, 1H).

Example 39

4'-Trifluoromethyl-biphenyl-2-carboxylic acid [3-(morpholine4-carbonyl)-quinolin-7-yl]-amide 7-[(4'-Trifluoromethyl-biphenyl-2-carbonyl)-amino]-quinoline-3-carboxylic acid (50 mg, 0.11 mmol) was combined with morpholine (11 mg, 0.12 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane and allowed to react overnight. The reaction mixture was concentrated, the residue was suspended in water, and the solid was collected by vacuum filtration. This material was purified by preparative thin-layer-chromatography on silica eluting with ethyl acetate. The product containing band was collected and eluted with 5% methanol in ethyl acetate to afford 28 mg of the title compound as a colorless solid.

MS (APCI) 506 (M+1)+; 504 (M−1)−

$^1$H NMR (DMSO-d$_6$) 3.40–3.75 (m, 8H), 7.55–7.76 (m, 9H), 7.96 (d, 1H, J=8.9 Hz), 8.36 (d, 1H, J=2.0 Hz), 8.41 (d, 1H, J=1.7 Hz), 8.85 (d, 1H, J=2.3 Hz), 10.80 (s, 1H).

Example 40

7-[(4'-Trifluoromethyl-biphenyl-2-carbonyl)-amino]-quinoline-3-carboxylic acid diethylamide 7-[(4'-Trifluoromethyl-biphenyl-2-carbonyl)-amino]-quinoline-3-carboxylic acid (50 mg, 0.11 mmol) was combined with diethylamine hydrochloride (15 mg, 0.14 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was diluted with 30 ml of ethyl acetate, and the organic phase washed sequentially with water, and brine, and then dried over anhydrous magnesium sulfate, filtered and concentrated under vacuum to afford 46 mg of the title compound as a yellow solid.

MS (APCI) 492 (M+1)+; 490 (M−1)−

$^1$H NMR (DMSO-d$_6$) 1.00–1.25 (m, 6H), 3.20–3.35 (m, 2H), 3.40–3.55 (m, 2H), 7.55–7.77 (m, 9H), 7.97 (d, 1H, J=8.9 Hz), 8.31 (d, 1H, J=2.3 Hz), 8.40 (d, 1H, J=1.7 Hz), 8.79 (d, 1H, J=2.3 Hz), 10.80 (s, 1H).

Example 41

4'-Trifluoromethyl-biphenyl-2-carboxylic acid [3-(piperidine-1-carbonyl)-quinolin-7-yl]-amide 7-[(4'-Trifluoromethyl-biphenyl-2-carbonyl)-amino]-quinoline-3-carboxylic acid (50 mg, 0.11 mmol) was combined with piperidine (10 mg, 0.11 mmol), 1-(3-dimethylaminopropyl)-3-ethylcarbodiimide hydrochloride (26 mg, 0.14 mmol), 1-hydroxybenzotriazole (17 mg, 0.13 mmol), and triethylamine (0.064 ml, 0.46 mmol) in 1 ml of dichloromethane. After stirring overnight at ambient temperature, the reaction mixture was concentrated, the residue was suspended in water, and the solid was collected by vacuum filtration to afford 45 mg of the title compound as a colorless solid.

MS (APCI) 504 (M+1)+; 502 (M−1)−

$^1$H NMR (DMSO-d$_6$) 1.40–1.70 (m, 6H), 3.20–3.40 (m, 2H), 3.50–3.70 (m, 2H), 7.55–7.76 (m, 9H), 7.96 (d, 1H, J=8.9 Hz), 8.31 (d, 1H, J=2.0 Hz), 8.40 (d, 1H, J=1.7 Hz), 8.81 (d, 1H, J=2.3 Hz), 10.80 (s, 1H).

Example 42

7-[(4'-Trifluoromethyl-biphenyl-2-carbonyl)-amino]-quinoline-3-carboxylic acid [bis-(4-fluoro-phenyl)-methyl]-amide The title compound was provided by the reaction of 7-[(4'-trifluoromethyl-biphenyl-2-carbonyl)-amino]-quinoline-3-carboxylic acid and C,C-bis-(4-fluoro-phenyl)-methylamine in a procedure analogous to Examples 1–34.

MS (APCI) 638 (M+1)+; 636 (M−1)−

Example 43

7-[(4'-Trifluoromethyl-biphenyl-2-carbonyl)-amino]-quinoline-3-carboxylic acid benzyl-ethyl-amide The title compound was provided by the reaction of 7-[(4'-trifluoromethyl-biphenyl-2-carbonyl)-amino]-quinoline-3-carboxylic acid and benzyl-ethyl-amine in a procedure analogous to Examples 1–34.

MS (APCI) 554 (M+1)+; 552 (M−1)−

Example 44

7-[(4'-Trifluoromethyl-biphenyl-2-carbonyl)-amino]-quinoline-3-carboxylic acid (3-phenyl-propyl)-amide The title compound was provided by the reaction of 7-[(4'-trifluoromethyl-biphenyl-2-carbonyl)-amino]- quinoline-3-carboxylic acid and 3-phenyl-propylamine in a procedure analogous to Examples 1–34.

MS (APCI) 554 (M+1)⁺; 552 (M−1)⁻

Example 45

7-[(4'-Trifluoromethyl-biphenyl-2-carbonyl)-amino]-quinoline-3-carboxylic acid ethyl-pyridin-2-ylmethyl-amide The title compound was provided by the reaction of 7-[(4'-trifluoromethyl-biphenyl-2-carbonyl)-amino]-quinoline-3-carboxylic acid and ethyl-pyridin-2-ylmethyl-amine in a procedure analogous to Examples 1–34.

MS (APCI) 555 (M+1)⁺; 553 (M−1)⁻

Example 46

7-[(4'-Trifluoromethyl-biphenyl-2-carbonyl)-amino]-quinoline-3-carboxylic acid phenethyl-amide The title compound was provided by the reaction of 7-[(4'-trifluoromethyl-biphenyl-2-carbonyl)-amino]-quinoline-3-carboxylic acid and phenethylamine in a procedure analogous to Examples 1–34.

MS (APCI) 540 (M+1)⁺; 538 (M−1)⁻

Example 47

7-[(4'-Trifluoromethyl-biphenyl-2-carbonyl)-amino]-quinoline-3-carboxylic acid phenylamide The title compound was provided by the reaction of 7-[(4'-trifluoromethyl-biphenyl-2-carbonyl)-amino]-quinoline-3-carboxylic acid and phenylamine in a procedure analogous to Examples 1–34.

MS (APCI) 512 (M+1)⁺; 510 (M−1)⁻

Example 48

7-[(4'-Trifluoromethyl-biphenyl-2-carbonyl)-amino]-quinoline-3-carboxylic acid (2-methoxy-ethyl)-amide The title compound was provided by the reaction of 7-[(4'-trifluoromethyl-biphenyl-2-carbonyl)-amino]-quinoline-3-carboxylic acid and 2-methoxy-ethylamine in a procedure analogous to Examples 1–34.

MS (APCI) 494 (M+1)⁺; 492 (M−1)⁻

Example 49

7-[(4'-Trifluoromethyl-biphenyl-2-carbonyl)-amino]-quinoline-3-carboxylic acid (1-methyl-3-phenyl-propyl)-amide The title compound was provided by the reaction of 7-[(4'-trifluoromethyl-biphenyl-2-carbonyl)-amino]-quinoline-3-carboxylic acid and 1-methyl-3-phenyl-propylamine in a procedure analogous to Examples 1–34.

MS (APCI) 568 (M+1)⁺; 566 (M−1)⁻

Example 50

7-[(4'-Trifluoromethyl-biphenyl-2-carbonyl)-amino]-quinoline-3-carboxylic acid indan-1-ylamide The title compound was provided by the reaction of 7-[(4'-trifluoromethyl-biphenyl-2-carbonyl)-amino]-quinoline-3-carboxylic acid and indan-1-ylamine in a procedure analogous to Examples 1–34.

MS (APCI) 552 (M+1)⁺; 550 (M−1)⁻

Example 51

7-[(4'-Trifluoromethyl-biphenyl-2-carbonyl)-amino]-quinoline-3-carboxylic acid (3,3-diphenyl-propyl)-amide The title compound was provided by the reaction of 7-[(4'-trifluoromethyl-biphenyl-2-carbonyl)-amino]-quinoline-3-carboxylic acid and 3,3-diphenyl-propylamine in a procedure analogous to Examples 1–34.

MS (APCI) 630 (M+1)⁺; 628 (M−1)⁻

Example 52

7-[(4'-Trifluoromethyl-biphenyl-2-carbonyl)-amino]-quinoline-3-carboxylic acid [2-(1H-indol-3-yl)-ethyl]-amide The title compound was provided by the reaction of 7-[(4'-trifluoromethyl-biphenyl-2-carbonyl)-amino]-quinoline-3-carboxylic acid and 2-(1H-indol-3-yl)-ethylamine in a procedure analogous to Examples 1–34.

MS (APCI) 579 (M+1)⁺; 577 (M−1)⁻

Example 53

7-[(4'-Trifluoromethyl-biphenyl-2-carbonyl)-amino]-quinoline-3-carboxylic acid (4-phenyl-butyl)-amide The title compound was provided by the reaction of 7-[(4'-trifluoromethyl-biphenyl-2-carbonyl)-amino]-quinoline-3-carboxylic acid and 4-phenyl-butylamine in a procedure analogous to Examples 1–34.

MS (APCI) 568 (M+1)⁺; 566 (M−1)⁻

Example 54

[R]-7-[(4'-Trifluoromethyl-biphenyl-2-carbonyl)-amino]-quinoline-3-carboxylic acid [(4-fluoro-phenyl)-pyridin-2-yl-methyl]-amide The title compound was provided by the reaction of 7-[(4'-trifluoromethyl-biphenyl-2-carbonyl)-amino]-quinoline-3-carboxylic acid and [R]-C-(4-fluoro-phenyl)-C-pyridin-2-yl-methylamine in a procedure analogous to Examples 1–34.

MS (APCI) 621 (M+1)⁺; 619 (M−1)⁻

Example 55

[S]-7-(4'-Trifluoromethyl-biphenyl-2-carbonyl)-amino]-quinoline-3-carboxylic acid [(4-fluoro-phenyl)-pyridin-2-yl-methyl]-amide The title compound was provided by the reaction of 7-[(4'-trifluoromethyl-biphenyl-2-carbonyl)-amino]-quinoline-3-carboxylic acid and [S]-C-(4-fluoro-phenyl)-C-pyridin-2-yl-methylamine in a procedure analogous to Examples 1–34.

MS (APCI) 621 (M+1)⁺; 619 (M−1)⁻

Example 56

2-Methyl-7-[(4'-trifluoromethyl-biphenyl-2-carbonyl)-amino]-quinoline-3-carboxylic acid (2-methoxy-ethyl)-amide The title compound was provided by the reaction of 2-methyl-7-[(4'-trifluoromethyl-biphenyl-2-carbonyl)- amino]-quinoline-3-carboxylic acid and 2-methoxy-ethylamine in a procedure analogous to Examples 1–34.

MS (APCI) 508 (M+1)⁺; 506 (M−1)⁻

Example 57

[S]-2-Methyl-7-[(4'-trifluoromethyl-biphenyl-2-carbonyl)-amino]-quinoline-3-carboxylic acid (phenyl-pyridin-2-yl-methyl)-amide The title compound was provided by the reaction of 2-methyl-7-[(4'-trifluoromethyl-biphenyl-2-carbonyl)-amino]-quinoline-3-carboxylic acid and [S]-C-phenyl-C-(2-pyridyl)-methylamine in a procedure analogous to Examples 1–34.

MS (APCI) 617 (M+1)⁺; 615 (M−1)⁻

Example 58

[R]-7-[2-(5-Trifluoromethyl-pyridin-2-yl)-benzoylamino]-quinoline-3-carboxylic acid (1-pyridin-2-yl-propyl)-amide 7-[2-(5-Trifluoromethyl-pyridin-2-yl)-benzoylamino]-quinoline-3-carboxylic acid (25 mg, 0.06 mmol), [R]-1-pyridin-2-yl-propylamine (23 mg, 0.17 mmol), 1-(3-dimethylaminopropyl)-3-ethylcarbodiimide hydrochloride (33 mg, 0.17 mmol), 1-hydroxybenzotriazole (23 mg, 0.17 mmol), and triethylamine (69 mg, 0.69 mmol) were combined in 5 ml of dichloromethane. After stirring 5 h at room temperature, the mixture was diluted with dichloromethane and washed with 10 ml of 1 N HCl, the organic layer was dried (magnesium sulfate), filtered and concentrated under vacuum. Purification of the residue by silica gel chromatography eluting with 5% methanol in ethyl acetate afforded the title compound.

MS (APCI) 556 (M+1)⁺; 554 (M−1)⁻

Example 59

[R]-7-[2-(5-Trifluoromethyl-pyridin-2-yl)-benzoylamino]-quinoline-3-carboxylic acid (1-pyridin-2-yl-ethyl)-amide The title compound was provided by reaction of 7-[2-(5-trifluoromethyl-pyridin-2-yl)-benzoylamino]-quinoline-3-carboxylic acid and [R]-1-pyridin-2-yl-ethylamine in a procedure analogous to Example 58.

MS (APCI) 542 (M+1)⁺; 540 (M−1)⁻

Example 60

[S]-7-[2-(5-Trifluoromethyl-pyridin-2-yl)-benzoylamino]-quinoline-3-carboxylic acid (phenyl-pyridin-2-yl-methyl)-amide The title compound was provided by reaction of 7-[2-(5-trifluoromethyl-pyridin-2-yl)-benzoylamino]-quinoline-3-carboxylic acid and [S]-C-phenyl-C-pyridin-2-yl-methylamine in a procedure analogous to Example 58.

MS (APCI) 604 (M+1)⁺; 602 (M−1)⁻

Example 61

[R]-7-[2-(6-Methyl-pyridin-3-yl)-benzoylamino]-quinoline-3-carboxylic acid (1-pyridin-2-yl-ethyl)-amide Prepared using a procedure analogous to Example 58 using trifluoro-methanesulfonic acid 6-methyl-pyridin-3-yl ester and [R]-1-pyridin-2-yl-ethylamine, which are made using procedures analogous to preparations 9–11B.

MS (APCI) 488 (M+1)⁺; 486 (M−1)⁻

Example 62

[R]-7-[2-(5-Methyl-pyridin-2-yl)-benzoylamino]-quinoline-3-carboxylic acid (1-pyridin-2-yl-ethyl)-amide Prepared using a procedure analogous to Example 58 using 2-chloro-5-methylpyridine and [R]-1-pyridin-2-yl-ethylamine, which are made using procedures analogous to preparations 9–11B.

MS (APCI) 488 (M+1)⁺; 486 (M−1)⁻

Example 63

[S]-7-{[2-(4-Trifluoromethyl-phenyl)-pyridine-3-carbonyl]-amino}-quinoline-3-carboxylic acid (phenyl-pyridin-2-yl-methyl)-amide 7-{[2-(4-Trifluoromethyl-phenyl)-pyridine-3-carbonyl]-amino}-quinoline-3-carboxylic acid (30 mg, 0.069 mmol), [S]-C-phenyl-C-pyridin-2-yl-methylamine (15 mg, 0.082 mmol), 1-(3-dimethylaminopropyl)-3-ethylcarbodiimide hydrochloride (16 mg, 0.082 mmol), 1-hydroxybenzotriazole (10 mg, 0.075 mmol), and triethylamine (0.038 ml, 0.27 mmol) were combined in 1 ml of dichloromethane. After stirring overnight at room temperature, the mixture was diluted with 30 ml of dichloromethane and washed with 2×20 ml of water, the organic layer was dried (magnesium sulfate), filtered and concentrated under vacuum to provide 39 mg of a yellow solid. Purification by preparative thin-layer-chromatography on silica gel eluting with 4% methanol in dichloromethane. The product-containing band was collected and eluted with 5% methanol in ethyl acetate to afford 22 mg of the title compound as a colorless solid.

MS (APCI) 593 (M+1)⁺; 591 (M−1)⁻

Example 64

[R]-7-{[2-(4-Trifluoromethyl-phenyl)-pyridine-3-carbonyl]-amino}-quinoline-3-carboxylic acid (1-pyridin-2-yl-ethyl)-amide The title compound was provided by reaction of 7-{[2-(4-trifluoromethyl-phenyl)-pyridine-3-carbonyl]-amino}-quinoline-3-carboxylic acid and [R]-1-pyridin-2-yl-ethylamine in a procedure analogous to Example 63.

MS (APCI) 542 (M+1)⁺; 540 (M−1)⁻

Example 65

[R]-7-{[2-(4-Trifluoromethyl-phenyl)-pyridine-3-carbonyl]-amino}-quinoline-3-carboxylic acid (1-pyridin-2-yl-propyl)-amide The title compound was provided by reaction of 7-{[2-(4-trifluoromethyl-phenyl)-pyridine-3-carbonyl]-amino}-quinoline-3-carboxylic acid and [R]-1-pyridin-2-yl-propylamine in a procedure analogous to Example 63.

MS (APCI) 556 (M+1)⁺; 554 (M−1)⁻

Example 66

[R]-7-[(2-p-Tolyl-pyridine-3-carbonyl)-amino]-quinoline-3-carboxylic acid (1-pyridin-2-yl-ethyl)-amide The title compound was prepared by the reactions with 4-methylphenylboronic acid and [R]-1-pyridin-2-ylethylamine, which are made using procedures analogous to preparations 12–15, in a procedure analogous to Example 63.

MS (APCI) 488 (M+1)$^+$; 486 (M−1)$^−$

Example 67

[R]-7-{[2-(4-Isopropyl-phenyl)-pyridine-3-carbonyl]-amino}-quinoline-3-carboxylic acid (1-pyridin-2-yl-ethyl)-amide The title compound was prepared by the reactions with 4-isopropylphenylboronic acid and [R]-1-pyridin-2-yl-ethylamine, which are made using procedures analogous to preparations 12–15, in a procedure analogous to Example 63.

MS (APCI) 516 (M+1)$^+$; 514 (M−1)$^−$

Example 68

[R]-7-{[2-(4-tert-Butyl-phenyl)-pyridine-3-carbonyl]-amino}-quinoline-3-carboxylic acid (1-pyridin-2-yl-ethyl)-amide The title compound was prepared by the reactions with 4-tert-butylphenylboronic acid and [R]-1-pyridin-2-yl-ethylamine, which are made using procedures analogous to preparations 12–15, in a procedure analogous to Example 63.

MS (APCI) 530 (M+1)$^+$; 528 (M−1$^{31}$ )−

Example 69

[R]-7-{[2-(4-Methoxy-phenyl)-pyridine-3-carbonyl]-amino}-quinoline-3-carboxylic acid (1-pyridin-2-yl-ethyl)-amide The title compound was prepared by the reactions with 4-methoxy-phenylboronic acid and [R]-1-pyridin-2-yl-ethylamine, which are made using procedures analogous to preparations 12–15, in a procedure analogous to Example 63.

MS (APCI) 504 (M+1)$^+$; 502 (M−1)$^−$

Example 70

[R]-7-{[2-(4-Ethyl-phenyl)-pyridine-3-carbonyl]-amino}-quinoline-3-carboxylic acid (1-pyridin-2-yl-ethyl)-amide The title compound was prepared by the reactions with 4-ethyl-phenylboronic acid and [R]-1-pyridin-2-yl-ethylamine, which are made using procedures analogous to preparations 12–15, in a procedure analogous to Example 63.

MS (APCI) 502 (M+1)$^+$; 500 (M−1)$^−$

Example 71

7-[(4'-tert-Butyl-biphenyl-2-carbonyl)-amino]-quinoline-3-carboxylic acid (phenyl-pyridin-2-yl-methyl)-amide To 2.5 ml of dichloromethane was added in sequence, 7-[(4'-tert-butyl-biphenyl-2-carbonyl)-amino]-quinoline-3-carboxylic acid (73.4 mg, 0.17 mmol), phenyl-pyridin-2-yl-methylamine (38.2 mg, 0.17 mmol), 1-hydroxybenzotriazole (25.7 g, 0.19 mmol), triethylamine ((96.6 µl, 0.69 mmol) and 1-[3-(dimethylamino)propyl]-3-ethylcarbodiimide hydrochloride (31.8 mg, 0.16 mmol). The solution was stirred overnight at room temperature. The reaction mixture was diluted with dichloromethane and washed with water (2×), and brine, dried over anhydrous sodium sulfate, and concentrated to dryness in vacuo. The residue was purified by preparative thick layer chromatography, eluting with 95:5 chloroform/methanol to yield the title compound as a colorless gum (78 mg, 78% yield).

MS (M+1)$^+$ 591.9

The title compounds of Examples 72–103 were prepared according to procedures analogous to that described in Example 71.

Example 72

7-[(Biphenyl-2-carbonyl)-amino]-quinoline-3-carboxylic acid (phenyl-pyridin-2-yl-methyl)-amide 98% yield.

MS (M+1)$^+$ 534.6

Example 73

7-[(Biphenyl-2-carbonyl)-amino]-quinoline-3-carboxylic acid (1-pyridin-2-yl-propyl)-amide 91% yield.

MS (M+1)$^+$ 487.2

Example 74

7-[(Biphenyl-2-carbonyl)-amino]-quinoline-3-carboxylic acid (di-pyridin-2-yl-methyl)-amide 61% yield.

MS (M+1)$^+$ 535.8

Example 75

7-[(4'-Methyl-biphenyl-2-carbonyl)-amino]-quinoline-3-carboxylic acid acid (phenyl-pyridin-2-yl-methyl)-amide 57% yield.

MS (M+1)$^+$ 548.5

Example 76

7-[(4'-Methyl-biphenyl-2-carbonyl)-amino]-quinoline-3-carboxylic acid acid (di-pyridin-2-yl-methyl)-amide 67% yield.

MS (M+1)$^+$ 550.0

Example 77

7-[(4'-Methyl-biphenyl-2-carbonyl)-amino]-quinoline-3-carboxylic acid acid (1-pyridin-2-yl-propyl)-amide 61% yield.

MS (M+1)$^+$ 501.1

Example 78

7-(2-Benzofuran-2-yl-benzoylamino)-quinoline-3-carboxylic acid (phenyl-pyridin-2-yl-methyl)-amide 59% yield.

MS (M+1)$^+$ 575.5

Example 79

7-[(4'-Isopropyl-biphenyl-2-carbonyl)-amino]-quinoline-3-carboxylic acid (di-pyridin-2-yl-methyl)-amide 69% yield.
MS (M+1)$^+$ 578.5

Example 80

7-[(4'-Isopropyl-biphenyl-2-carbonyl)-amino]-quinoline-3-carboxylic acid acid (phenyl-pyridin-2-yl-methyl)-amide 76% yield.
MS (M+1)$^+$ 577.2

Example 81

7-[(4'-Isopropyl-biphenyl-2-carbonyl)-amino]-quinoline-3-carboxylic acid (1-pyridin-2-yl-propyl)-amide 72% yield.
MS (M+1)$^+$ 529.5

Example 82

7-[(3'-Methyl-biphenyl-2-carbonyl)-amino]-quinoline-3-carboxylic acid (phenyl-pyridin-2-yl-methyl)-amide 75% yield.
MS (M+1)$^+$ 549.1

Example 83

7-[(4'-Ethyl-biphenyl-2-carbonyl)-amino]-quinoline-3-carboxylic acid (phenyl-pyridin-2-yl-methyl)-amide 81% yield.
MS (M+1)$^+$ 563.5

Example 84

7-[(4'-Ethyl-biphenyl-2-carbonyl)-amino]-quinoline-3-carboxylic acid (1-pyridin-2-yl-propyl)-amide 64% yield.
MS (M+1)$^+$ 515.4

Example 85

7-[(4'-tert-Butyl-biphenyl-2-carbonyl)-amino]-quinoline-3-carboxylic acid (1-pyridin-2-yl-propyl)-amide 73% yield.
MS (M+1)$^+$ 543.3

Example 86

7-[(4'-Ethylsulfanyl-biphenyl-2-carbonyl)-amino]-quinoline-3-carboxylic acid (phenyl-pyridin-2-yl-methyl)-amide 77% yield.
MS (M+1)$^+$ 595.2

Example 87

7-[(4'-Ethylsulfanyl-biphenyl-2-carbonyl)-amino]-quinoline-3-carboxylic acid (1-pyridin-2-yl-propyl)-amide 77% yield.
MS (M+1)$^+$ 547.3

Example 88

7-(2-Naphthalen-2-yl-benzoylamino)-quinoline-3-carboxylic acid (phenyl-pyridin-2-yl-methyl)-amide 76% yield.
MS (M+1)$^+$ 585.0

Example 89

7-(2-Benzo[1,3]dioxol-5-yl-benzoylamino)-quinoline-3-carboxylic acid (phenyl-pyridin-2-yl-methyl)-amide 84% yield.
MS (M+1)$^+$ 579.8

Example 90

7-[(3',4'-Dimethyl-biphenyl-2-carbonyl)-amino]-quinoline-3-carboxylic acid (phenyl-pyridin-2-yl-methyl)-amide 9.4% yield.
MS (M+1)$^+$ 563.4

Example 91

7-[(2'-Methyl-biphenyl-2-carbonyl)-amino]-quinoline-3-carboxylic acid (phenyl-pyridin-2-yl-methyl)-amide 43% yield.
MS (M+1)$^+$ 549.3

Example 92

7-[(3'-Fluoro-4'-methyl-biphenyl-2-carbonyl)-amino]-quinoline-3-carboxylic acid (phenyl-pyridin-2-yl-methyl)-amide 69% yield.
MS (M+1)$^+$ 567.4

Example 93

7-[(4'-Ethoxy-biphenyl-2-carbonyl)-amino]-quinoline-3-carboxylic acid (phenyl-pyridin-2-yl-methyl)-amide 63% yield.
MS (M+1)$^+$ 577.4

Example 94

7-[(4'-Ethoxy-biphenyl-2-carbonyl)-amino]-quinoline-3-carboxylic acid (1-pyridin-2-yl-propyl)-amide 61% yield.
MS (M+1)$^+$ 531.3

Example 95

7-[(4'-Ethoxy-biphenyl-2-carbonyl)-amino]-quinoline-3-carboxylic acid (di-pyridin-2-yl-methyl)-amide 60% yield.
MS (M+1)$^+$ 580.4

Example 96

7-[2-(2,3-Dihydro-benzofuran-5-yl)-benzoylamino]-quinoline-3-carboxylic acid (phenyl-pyridin-2-yl-methyl)-amide 59% yield.
MS (M+1)$^+$ 577.3

Example 97

7-[(4'-Propoxy-biphenyl-2-carbonyl)-amino]-quinoline-3-carboxylic acid (phenyl-pyridin-2-yl-methyl)-amide 80% yield.
MS (M+1)$^+$ 591.0

Example 98

7-[(4'-Propoxy-biphenyl-2-carbonyl)-amino]-quinoline-3-carboxylic acid (1-pyridin-2-yl-propyl)-amide 47% yield.
MS (M+1)$^+$ 545.4

Example 99

7-[(4'-Butoxy-biphenyl-2-carbonyl)-amino]-quinoline-3-carboxylic acid (phenyl-pyridin-2-yl-methyl)-amide 79% yield.
MS (M+1)$^+$ 607.4

Example 100

7-[(4'-Butoxy-biphenyl-2-carbonyl)-amino]-quinoline-3-carboxylic acid (1-pyridin-2-yl-propyl)-amide 56% yield.
MS (M+1)$^+$ 559.4

Example 101

7-[(3-Methyl-4-oxo-2-phenyl-4H-chromene-8-carbonyl)-amino]-quinoline-3-carboxylic acid (1-pyridin-2-yl-propyl)-amide 5 46% yield.
MS (M+1)$^+$ 568.7

Example 102

7-[(3-Methyl-4-oxo-2-phenyl4H-chromene-8-carbonyl)-amino]-quinoline-3-carboxylic acid (phenyl-pyridin-2-yl-methyl)-amide 41% yield.
MS (M+1)$^+$ 661.5

Example 103

7-[(3-Methyl-4-oxo-2-phenyl-4H-chromene-8-carbonyl)-amino]-quinoline-3-carboxylic acid (di-pyridin-2-yl-methyl)-amide 56% yield.
MS (M+1)$^+$ 616.

The title compounds of Examples 104–121 were prepared according to procedures analogous to that described in Example 71.

Example 104

7-(2-Cyclohexylmethoxy-benzoylamino)-quinoline-3-carboxylic acid (di-pyridin-2-yl-methyl)-amide 68% yield.
MS (M+1)$^+$ 571.9

Example 105

7-(2-Cyclohexylmethoxy-benzoylamino)-quinoline-3-carboxylic acid (phenyl-pyridin-2-yl-methyl)-amide 25% yield.
MS (M+1)$^+$ 571.0

Example 106

7-(2-Cyclohexylmethoxy-benzoylamino)-quinoline-3-carboxylic acid (1-pyridin-2-yl-propyl)-amide 2% yield.
MS (M+1)$^+$ 522.9

Example 107

7-(2-Cyclohexylmethoxy-3-methoxy-benzoylamino)-quinoline-3-carboxylic acid (phenyl-pyridin-2-yl-methyl)-amide 68% yield.
MS (M+1)$^+$ 601.0

Example 108

7-(2-Cyclohexylmethoxy-3-methoxy-benzoylamino)-quinoline-3-carboxylic acid (di-pyridin-2-yl-methyl)-amide 50% yield.
MS (M+1)$^+$ 601.6

Example 109

7-(2-Cyclohexylmethoxy-3-methoxy-benzoylamino)-quinoline-3-carboxylic acid (1-pyridin-2-yl-propyl)-amide 40% yield.
MS (M+1)$^+$ 553.2

Example 110

7-[2-(Bicyclo[2.2.1]hept-2-ylmethoxy)-benzoylamino]-quinoline-3-carboxylic acid (di-pyridin-2-yl-methyl)-amide 71% yield.
MS (M+1)$^+$ 583.9

Example 111

7-[2-(Bicyclo[2.2.1]hept-2-ylmethoxy)-benzoylamino]-quinoline-3-carboxylic acid (phenyl-pyridin-2-yl-methyl)-amide 24% yield.
MS (M+1)$^+$ 582.9

Example 112

7-[2-(Bicyclo[2.2.1]hept-2-ylmethoxy)-benzoylamino]-quinoline-3-carboxylic acid (1-pyridin-2-yl-propyl)-amide 60% yield.
MS (M+1)$^+$ 534.8

Example 113

7-[2-(Bicyclo[2.2.1]hept-2-ylmethoxy)-3-methoxy-benzoylamino]-quinoline-3-carboxylic acid (di-pyridin-2-yl-methyl)-amide 58% yield.
MS (M+1)$^+$ 613.8

Example 114

7-[2-(Bicyclo[2.2.1]hept-2-ylmethoxy)-3-methoxy-benzoylamino]-quinoline-3-carboxylic acid (phenyl-pyridin-2-yl-methyl)-amide 95% yield.
MS (M+1)$^+$ 612.4

Example 115

7-[2-(Bicyclo[2.2.1]hept-2-ylmethoxy)-3-methoxy-benzoylamino]-quinoline-3-carboxylic acid (1-pyridin-2-yl-propyl)-amide

79% (M+1)$^+$ 564.7

Example 116

7-(2-Pentyloxy-benzoylamino)-quinoline-3-carboxylic acid (di-pyridin-2-yl-methyl)-amide 72% yield.
MS (M+1)$^+$ 546.1

Example 117

7-(2-Pentyloxy-benzoylamino)-quinoline-3-carboxylic (phenyl-pyridin-2-yl-methyl)-amide 53% yield.
MS (M+1)$^+$ 545.1

Example 118

7-(2-Pentyloxy-benzoylamino)-quinoline-3-carboxylic acid (1-pyridin-2-yl-propyl)-amide 93% yield.
MS (M+1)$^+$ 497.3

Example 119

7-(3-Methoxy-2-pentyloxy-benzoylamino)-quinoline-3-carboxylic acid (di-pyridin-2-yl-methyl)-amide 2% yield.
MS (M+1)$^+$ 576.0

Example 120

7-(3-Methoxy-2-pentyloxy-benzoylamino)-quinoline-3-carboxylic acid (phenyl-pyridin-2-yl-methyl)-amide 57% yield.
MS (M+1)$^+$ 574.4

Example 121

7-(3-Methoxy-2-pentyloxy-benzoylamino)-quinoline-3-carboxylic acid (1-pyridin-2-yl-propyl)-amide 97% yield,
MS (M+1)$^+$ 526.8

Example 122

7-(2-Benzyloxy-3-methoxy-benzoylamino)-quinoline-3-carboxylic acid (di-pyridin-2-yl-methyl)-amide A mixture of 2-benzyloxy-3-methoxybenzoic acid (109 mg, 0.42 mmol), thionyl chloride (5 ml) and 1 drop dimethylformamide was heated under reflux for 2 hr. The thionyl chloride was removed in vacuo, with traces being removed by adding methylene chloride and concentrating the solution in vacuo. The resulting 2-benzyloxy-3-methoxybenzoyl chloride was dissolved in chloroform and the solution was added dropwise to a solution of 7-amino-quinoline-3-carboxylic acid (di-pyridin-2-yl-methyl)-amide (75 mg, 0.21 mmol), 4-(N,N-dimethylaminopyridine) (DIMAP) (3 mg, 0.02 mmol) and pyridine (0.068 ml, 0.84 mmol) in chloroform at room temperature. The resulting solution was heated under reflux for 3 hr, then cooled to room temperature and concentrated to dryness in vacuo. The residue was dissolved in ethyl acetate, washed sequentially with water and brine, dried over anhydrous sodium sulfate and concentrated to dryness in vacuo. The residue (960 mg) was purified by column chromatography on silica gel, eluting with 98:2 chloroform/methanol to yield the title compound as a solid (40.3 mg, 34% yield).

The title compounds of Examples 123–131 were prepared according to procedures analogous to that described in Example 122.

Example 123

7-(2-Cyclopentylethoxy-3-methoxy-benzoylamino)-quinoline-3-carboxylic acid (di-pyridin-2-yl-methyl)-amide 62% yield.
MS (M+1)$^+$ 602.3

Example 124

7-[3-Methoxy-2-(4,4,4-trifluoro-butoxy)-benzoylamino]-quinoline-3-carboxylic acid (di-pyridin-2-yl-methyl)-amide 63% yield.
MS (M+1)$^+$ 616.1

Example 125

7-[3-Methoxy-2-(3-methyl-butoxy)-benzoylamino]-quinoline-3-carboxylic acid (di-pyridin-2-yl-methyl)-amide 65% yield.
MS (M+1)$^+$ 576.3

Example 126

7-(2-Cyclobutylmethoxy-3-methoxy-benzoylamino)-quinoline-3-carboxylic acid (di-pyridin-2-yl-methyl)-amide 53% yield.
MS (M+1)$^+$ 574.1

Example 127

7-(2-Cyclopentylmethoxy-3-methoxy-benzoylamino)-quinoline-3-carboxylic acid (di-pyridin-2-yl-methyl)-amide 65% yield.
MS (M+1)$^+$ 588.2

Example 128

2-Hexyloxy-3-methoxy-benzoylamino)-quinoline-3-carboxylic acid (di-pyridin-2-yl-methyl)-amide 73% yield.
MS (M+1)$^+$ 576.0

Example 129

7-(2-Cyclohexylethoxy-3-methyl-benzoylamino)-quinoline-3-carboxylic acid (di-pyridin-2-yl-methyl)-amide 49% yield.
MS (M+1)$^+$ 600.5

Example 130

7-(2-Cyclohexylmethoxy-3-methyl-benzoylamino)-quinoline-3-carboxylic acid (di-pyridin-2-yl-methyl)-amide 51% yield.
MS (M+1)$^+$ 586.3

Example 131

7-(3-Chloro-2-cyclohexylmethoxy-benzoylamino)-quinoline-3-carboxylic acid (di-pyridin-2-yl-methyl)-amide 36% yield.
MS (M+1)$^+$ 606.3

Example 132

(+)-(S)-7-[(4'-trifluoroethyl-biphenyl-2-carbonyl)-amino]-quinoline-3-carboxylic acid (phenyl-pyridin-2-yl-methyl)-amide:

Step 1

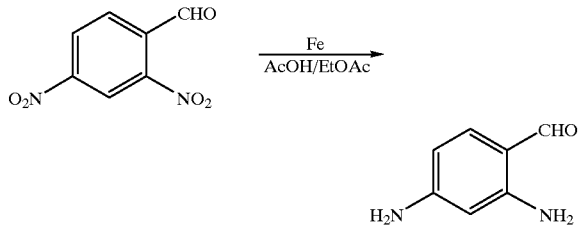

2,4-Diaminobenzaldehyde

To a nitrogen purged 5 liter 4-neck flask fitted with a condenser, mechanical stirrer, addition funnel, and temperature probe, was added 325 mesh iron dust, which can be obtained from Aldrich, Milwaukee, Wis. (220 g, 3.9 mol, 8 equiv), water (800 mL), and glacial acetic acid (5 mL). Over the next hour, some frothing occurred and the temperature rose to 28° C. In a separate container, 2,4-dinitrobenzaldehyde (97 g, 0.49 mol, 1 equiv) was dissolved in 1:1 glacial acetic acid/ethyl acetate (800 mL). 2,4-Dinitrobenzaldehyde can be purchased from Aldrich, Milwaukee, Wis. About 5 mL of the 2,4-dinitrobenzaldehyde solution was added dropwise to the iron mixture, which led to a dissipation of the frothing. The reaction mixture was warmed to 35° C with a steam bath. Without further heating, the remaining dinitrobenzaldehyde solution was added at such a rate as to maintain the temperature below 50° C. The addition was completed after 6 hours. The reaction mixture was diluted with water (1 L) and diatomaceous earth (BNL Fine Chemicals and Reagents, Meriden, Conn.) was added (100 g). The reaction mixture was stirred an additional 3 hours at which point the temperature had dropped to 25° C. The solids were removed by filtration. The organic layer was separated and the aqueous layer was extracted with ethyl acetate (3×400 mL). The extracts were then used to wash the solids from the initial filtration. The organic layers were combined and washed with water (400 mL) and saturated aqueous NaHCO$_3$ (3×400 mL). The combined organic layers were dried over MgSO$_4$ and Darco G-60® (activated charcoal; BNL Fine Chemicals and Reagents, Meriden, Conn.) (10 g). After filtration to remove the drying agents, the organic layers were concentrated in vacuo to a slurry and diluted with 1 L of hexanes. The precipitated solids were collected by suction filtration and dried in air to give 2,4-diaminobenzaldehyde (48 g, 71%) as a light yellow solid.

$^1$H NMR (acetone-d$_6$) δ5.48 (br s, 2H), 5.94 (d, 1H, J=1.9 Hz), 6.08 (dd, 1H, J=2.0, 8.6 Hz), 6.75 (br s, 2H), 7.20 (d, 1H, J=8.6 Hz), 9.51 (s, 1H).

Step 2

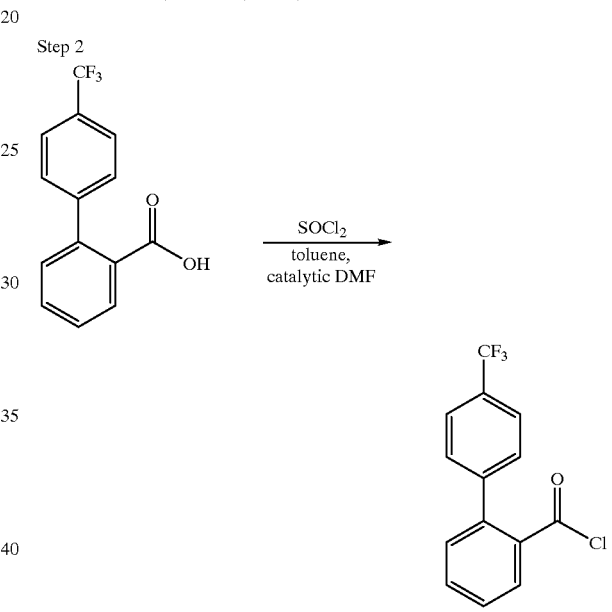

4'-Trifluoromethyl-biphenyl-2-carbonyl chloride

To a nitrogen purged 3 liter 4-neck flask fitted with a condenser, mechanical stirrer, temperature probe, and connected to a 2M aqueous NaOH scrubber was added toluene (1 L), 4'-trifluoromethyl-biphenyl-2-carboxylic acid (250 g, 0.94 mol, 1 equiv), and DMF (5 mL). 4'-Trifluoromethyl-biphenyl-2-carboxylic acid can be obtained from Aldrich, Milwaukee, Wis. The solution was heated to 60° C. and thionyl chloride (110 mL, 1.5 mol, 1.6 equiv) was added at such a rate as to maintain the temperature below 65° C. The addition was complete after 30 minutes and the reaction was heated to reflux. After 4 hours, the heating was stopped and the reaction was allowed to stir overnight at room temperature. The reaction mixture was concentrated in vacuo and the residue was used in the next step without further purification. The material crystallized to a solid at room temperature.

$^1$H NMR (CDCl$_3$) δ7.37 (dd, 1H, J=1.1, 7.6 Hz), 7.43 (d, 2H, J=8.1 Hz), 7.55 (td, 1H, J=1.3, 7.7 Hz), 7.66 (td, 1H, J=1.3, 7.5 Hz), 7.68 (d, 2H, J=8.1 Hz), 8.11 (dd, 1H, J=1.2, 7.9 Hz).

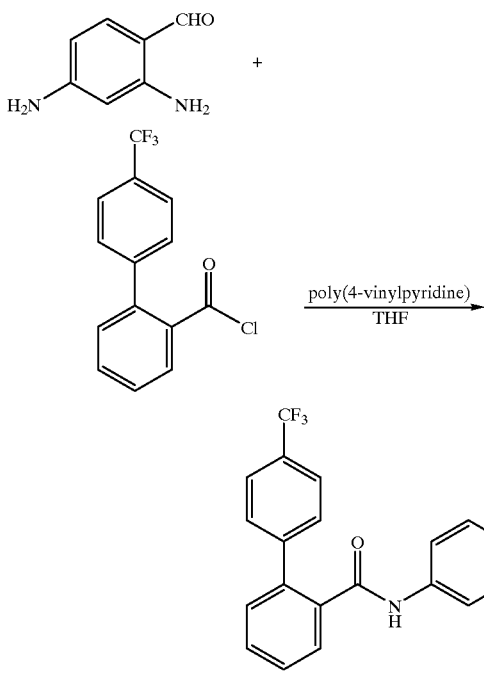

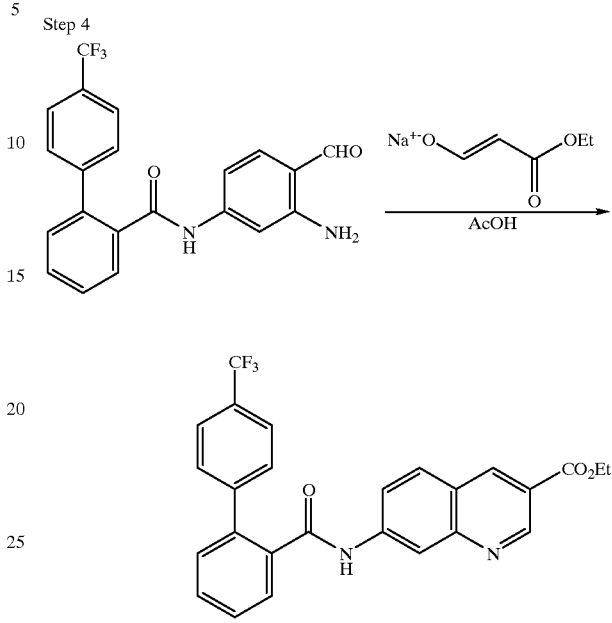

4'-Trifluoromethyl-biphenyl-2-carboxylic acid (3-amino-4-formyl-phenyl)-amide

To a nitrogen purged 12 liter 3-neck flask fitted with a mechanical stirrer and temperature probe was added THF (4.3 L) and 2,4-diaminobenzaldehyde (50 g, 0.37 mol, 1 equiv). After cooling the solution to -70° C. (dry ice/acetone bath), poly(4-vinylpyridine), which can be obtained from Aldrich, Milwaukee, Wis., 25% cross-linked, (210 g) was added. A solution of 4'-trifluoromethyl-biphenyl-2-carbonyl chloride (105 g, 0.37 mol, 1 equiv) in THF (1 L) was added at such a rate as to maintain the temperature below −60° C. The light orange reaction mixture was allowed to warm to room temperature over 4 hours to give a dark red reaction mixture. (HPLC analysis showed an 18:1 mixture of mono- (retention time (rt)=4.8 min) to di- (rt=3.1 min) acylated products along with 5% residual starting material (rt=18.8 min), (Zorbax SIL (150 mm) from Agilent Technologies, Palo Alto, Calif. 2 mL/min 90:10 hexanes/isopropanol, 0.1% diethylamine, 250 nm, 40° C.). The reaction was quenched with 1 N NaOH (450 mL) and allowed to stir overnight at 25° C. The reaction mixture was filtered and the solids were washed with ethyl acetate (5×200 mL) and the combined organic layers were concentrated in vacuo to give a brown oil. The oil was dissolved in $CH_2Cl_2$ (1.5 L) and silica gel (EM Science, Gibbstown, N.J., 230–400 mesh or 0.04–0.06 mm particle size) (410 g) and Darco G-60® (10 g, BNL Fine Chemicals and Reagents) were added. The slurry was stirred for 15 minutes and filtered. The silica was washed with $CH_2Cl_2$ (5×200 mL). The combined organic layers were concentrated in vacuo and the methylene chloride was displaced with 1:1 hexanes/diisopropylether. The precipitated product was collected by suction filtration and dried in air to give 4'-trifluoromethyl-biphenyl-2-carboxylic acid (3-amino-4-formyl-phenyl)-amide (40 g, 30%, 43:1 mono-:bis acylated by HPLC) as a light yellow solid.

MS (APCI) 385 $(M+1)^+$; 383 $(M-1)^-$ $^1$H NMR (DMSO-$d_6$) δ6.65 (dd, 1H, J=1.7, 8.7 Hz), 7.15 (br s, 2H), 7.25 (s, 1H), 7.38 (d, 1H, J=8.7 Hz), 7.46–7.68 (m, 6H), 7.74 (d, 2H, J=8.3 Hz), 9.57 (s, 1H), 10.51 (s, 1H).

Step 4

7-[(4'-Trifluoromethyl-biphenyl-2-carbonyl)-amino]-quinoline-3-carboxylic acid ethyl ester

A solution of 4'-trifluoromethyl-biphenyl-2-carboxylic acid (3-amino-4-formyl-phenyl)-amide (7 g, 18.2 mmol, 1 equiv) and 3-hydroxy-acrylic acid ethyl ester, sodium salt (2.52 g, 18.2 mmol, 1 equiv) in glacial acetic acid (70 mL, 10 volumes) was heated at 80° C. for 2 hours. Additional 3-hydroxy-acrylic acid ethyl ester, sodium salt (2.52 g, 18.2 mmol, 1 equiv) was added and the solution heated for 15 hours. Again, additional 3-hydroxy-acrylic acid ethyl ester, sodium salt (1.26 g, 9.1 mmol, 0.5 equiv) was added and the solution heated for another 4 hours. The reaction mixture was concentrated in vacuo. The residue was dissolved in EtOAc (300 mL) and the organic layer was washed with a saturated aqueous sodium carbonate solution (2×200 mL) and 1 N NaOH solution (200 mL). The combined aqueous layers were back extracted with ethyl acetate (200 mL). The combined organic layers were dried over sodium sulfate and treated with Darco G-60® (7 g). The solids were removed by filtration and the filtrate was concentrated to afford crude 7-[(4'-trifluoromethyl-biphenyl-2-carbonyl)-amino]-quinoline-3-carboxylic acid ethyl ester, which was used in the next step without further purification.

MS (APCI) 465 $(M+1)^+$; 463 $(M-1)^-$ $^1$H NMR (DMSO-$d_6$) δ1.34 (t, 3H, J=7.1 Hz), 4.36 (q, 2H, J=7.1 Hz), 7.53–7.73 (m, 9H), 8.08 (d, 1H, J=8.7 Hz), 8.44 (d, 1H, J=1.3 Hz), 8.84 (d, 1H, J=2.1 Hz), 9.21 (d, 1H, J=2.1 Hz), 10.95 (s, 1H).

Step 5

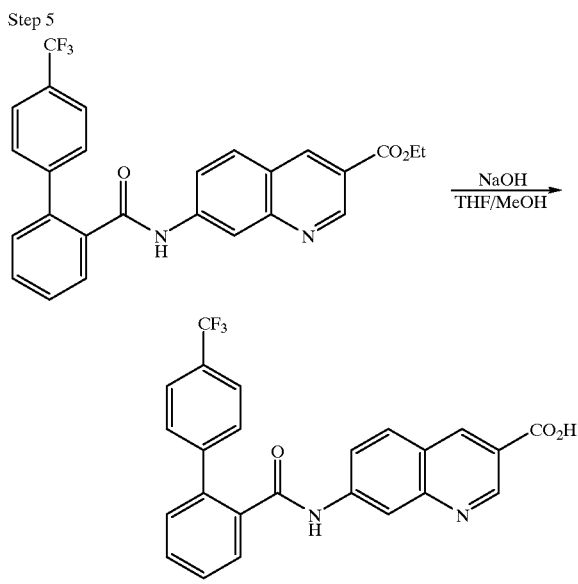

7-[(4'-Trifluoromethyl-biphenyl-2-carbonyl)-amino]-quinoline-3-carboxylic acid

To a solution of 7-[(4'-trifluoromethyl-biphenyl-2-carbonyl)-amino]-quinoline-3-carboxylic acid ethyl ester (8.45 g, 18.2 mmol, 1 equiv) in MeOH (85 mL) and THF (85 mL) was added 1 N NaOH (91 mL, 91 mmol, 5 equiv). The solution was stirred at room temperature for 4 hours. The organic layer was removed in vacuo and the aqueous layer was washed with EtOAc (100 mL). The aqueous layer was then acidified to a pH of about 4 with concentrated HCl and a precipitate formed. The mixture was stirred for 48 hours and the solids collected by filtration to provide 7-[(4'-trifluoromethyl-biphenyl-2-carbonyl)-amino]-quinoline-3-carboxylic acid (4.5 g, 57% over two steps) as a yellow solid.

MS (APCI) 437 (M+1)$^+$; 435 (M−1)$^−$ $^1$H NMR (DMSO-d$_6$) δ7.54–7.74 (m, 9H), 8.08 (d, 1H, J=8.7 Hz), 8.44 (s, 1H), 8.84 (d, 1H, J=1.7 Hz), 9.22 (d, 1H, J=2.0 Hz), 10.90 (s, 1H).

Step 6

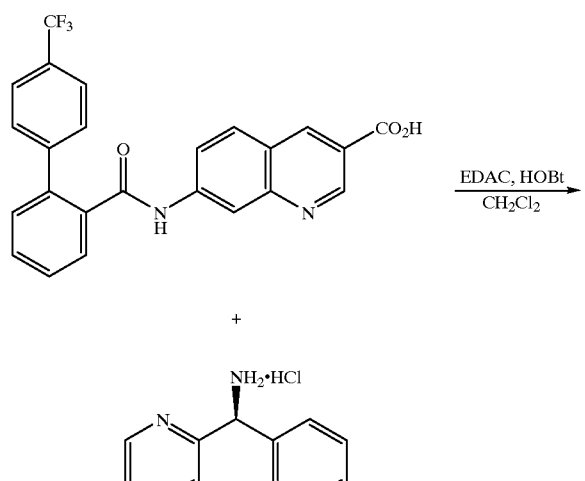

(+)-(S)-7-[(4'-Trifluoromethyl-biphenyl-2-carbonyl)-amino]-quinoline-3-carboxylic acid (phenyl-pyridin-2-yl-methyl)-amide To a suspension of 7-[(4'-trifluoromethyl-biphenyl-2-carbonyl)-amino]-3-carboxylic acid (10 g, 22.9 mmol, 1 equiv) and methylene chloride (168 mL, 16.8 volumes) was added (S)-phenyl-(2-pyridyl)-methylamine, hydrochloric acid salt (6.5 g, 29.8 mmol, 1.3 equiv), 3-ethyl-1-(3-diethylaminopropyl)-carbodiimide hydrochloride (EDAC) (5.3 g, 27.5 mmol, 1.2 equiv), and hydroxy benzotriazole (HOBT) (3.3 g, 24.1 mmol, 1.05 equiv). Diisopropylethylamine was added dropwise (11.97 g, 92.6 mmol, 4.04 equiv). The resulting solution was allowed to stir for 12 hours at room temperature. The solution was then extracted with 0.5 N hydrochloric acid (3×80 mL), saturated sodium hydrogen carbonate (2×80 mL) and saturated sodium chloride (80 mL). The organic layer was dried over sodium sulfate and concentrated in vacuo to give (+)-(S)-7-[(4'-trifluoromethyl-biphenyl-2-carbonyl)-amino]-quinoline-3-carboxylic acid (phenyl-pyridin-2-yl-methyl)-amide (12.2 g, 88.4%).

Example 133

(+)-(S)-7-[(4'-trifluoromethyl-biphenyl-2-carbonyl)-amino]-quinoline-3-carboxylic acid (phenyl-pyridin-2-yl-methyl)-amide Step 1

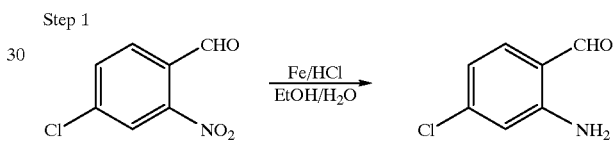

4-Chloro-2-aminobenzaldehyde

To a 3-neck flask fitted with a reflux condenser and a mechanical stirrer, were added 4-chloro-2-nitrobenzaldehyde (25 g, 135 mmol, 1 equiv), ethanol (375 mL), and water (100 mL). 4-Chloro-2-nitrobenzaldehyde can be obtained from P.H.T. International, Inc., Charlotte, N.C. Iron dust (225 mesh, Aldrich, Milwaukee, Wis.) (22.6 g, 405 mmol, 3 equiv) and concentrated hydrochloric acid (5.7 mL, 67.5 mmol, 0.5 equiv) was added. The slurry was heated to 85° C. for two hours, cooled to room temperature,

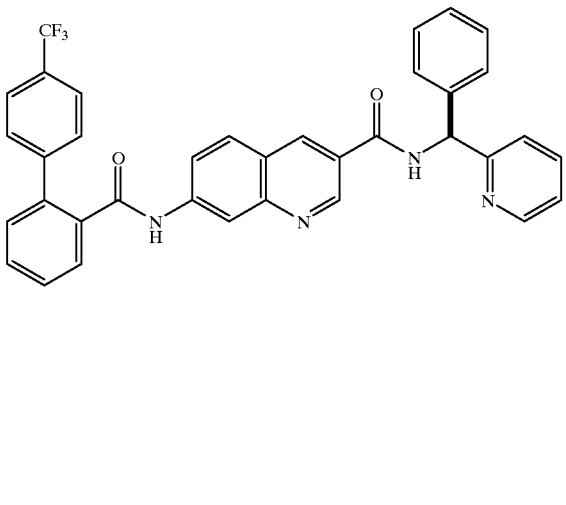

filtered through diatomaceous earth and rinsed with ethanol (100 mL) and toluene (100 mL). The solution was transferred to a separatory funnel and toluene (300 mL) were added. The organic layer was washed with saturated sodium bicarbonate solution (300 mL) and brine (300 mL), then dried over sodium sulfate and then concentrated to provide 4-chloro-2-aminobenzaldehyde (17.4 g, 83%) as a yellow solid.

$^1$H NMR (CDCl$_3$) δ7.58 (dd, 1H, J=2.1, 8.7 Hz), 7.89 (d, 1H, J=8.7 Hz), 8.17 (s, 1H), 8.83 (d, 1H, J=1.7 Hz), 9.45 (br s, 2H).

Step 2

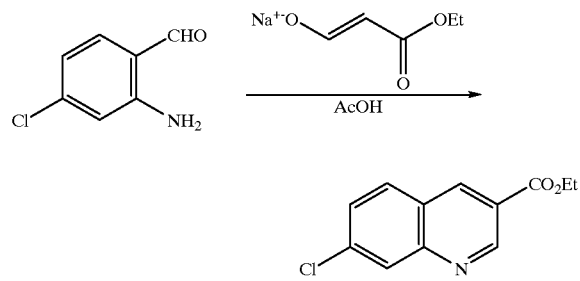

7-Chloro-quinoline-3-carboxylic acid ethyl ester

A solution of 4-chloro-2-aminobenzaldehyde (15 g, 96 mmol, 1 equiv) and 3-hydroxy-acrylic acid ethyl ester, sodium salt (6.65 g, 48 mmol, 0.5 equiv) in glacial acetic acid (175 mL), was heated at reflux for 3 hours. Additional 3-hydroxy-acrylic acid ethyl ester, sodium salt (6.65 grams, 48 mmol, 0.5 equivalents) was added and the reaction was heated at reflux for another 2.5 hours. Additional 3-hydroxy-acrylic acid ethyl ester, sodium salt (4 g, 28.8 mmol, 0.3 equiv) was added and the reaction was heated at reflux for an additional 12 hours. Additional 3-hydroxy-acrylic acid ethyl ester, sodium salt (4 g, 28.8 mmol, 0.3 equiv) was added and the reaction was heated at reflux for 4 hours. The reaction mixture was cooled and concentrated in vacuo. The residue was dissolved in ethyl acetate (200 mL) and washed with saturated sodium bicarbonate solution (200 mL). The organic layer was then washed with brine (200 mL), dried over sodium sulfate, and treated with activated charcoal (Darco G-60®) (20 g). The mixture was filtered through diatomaceous earth. Silica gel (15 g) (EM Science, Gibbstown, N.J., 230–400 mesh, 0.04–0.06 mm particle size) was added to the solution and stirred for 3 hours. The slurry was filtered, rinsed with toluene (100 ml) and then 10% ethyl acetate in toluene (200 mL). The combined organic layers were concentrated and the resulting solid was stirred in isopropanol overnight to yield 7-chloro-quinoline-3-carboxylic acid ethyl ester (3 g, 13% yield) as a pale yellow powder.

$^1$H NMR (CDCl$_3$) δ1.38 (m, 3H), 4.45 (m, 2H), 7.57 (dd, 1H, J=2.1, 8.7 Hz), 7.87 (d, 1H, J=8.7 Hz), 8.16 (d, 1H, J=1.3 Hz), 8.81 (d, 1H, J=2.1 Hz), 9.44 (d, 1H, J=2.1 Hz).

3-Hydroxy-acrylic acid ethyl ester, sodium salt can be made by the following procedure:

To a 20° C. slurry of sodium ethoxide (250 g, 3.49 mol, 1.5 equiv) and ethyl acetate (750 mL, 4.2 volumes) was dropwise added ethyl formate (178 g, 2.33 mol, 1 equiv) while keeping the internal temperature below 35° C. with external cooling. The resulting light tan slurry was stirred for 4 hours at room temperature and then diluted with hexanes (200 mL, 1.12 volumes). The off-white solids were collected by suction filtration and dried in vacuo at 20°–25° C. to provide 3-hydroxy-acrylic acid ethyl ester, sodium salt (204.4 g, 63.5 %)

Step 3

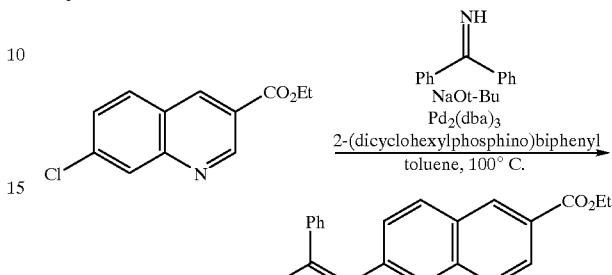

7-(Benzhydrylidene-amino)-quinoline-3-carboxylic acid ethyl ester

7-Chloro-quinoline-3-carboxylic acid ethyl ester (1 g, 4.24 mmol, 1 equiv), dry sodium t-butoxide (571 mg, 5.94 mmol, 1.4 equiv), tris(dibenzylideneacetone)dipalladium (19.5 mg, 21.2 μmol, 1 mol % equiv), and 2-(dicylcohexylphosphino)biphenyl (30 mg, 84.8 μmol, 4 mol % equiv) were placed in a round bottom flask with a magnetic stir bar. The flask was flushed with nitrogen. Benzophenone imine (783 μL, 4.66 mmol, 1.1 equiv) and toluene (8.5 mL) were added. The flask was fitted with a reflux condenser and the reaction was heated at 100° C. for 12 hours. The reaction mixture was cooled to room temperature and diluted with ethyl acetate (20 mL). The reaction mixture was washed with a saturated sodium bicarbonate solution (25 mL), saturated ammonium chloride solution (25 mL), and brine (25 mL). The organic layer was dried over sodium sulfate and then treated with activated charcoal (Darco G-60®) (1 g). The mixture was filtered through diatomaceous earth and concentrated. The residue was stirred in a minimal amount of isopropanol (about 2 mL) to provide 7-(benzhydrylidene-amino)-quinoline-3-carboxylic acid ethyl ester (199 mg, 12%) as a pale yellow solid.

MS (APCI) 381 (M+1)$^+$ $^1$H NMR (CDCl$_3$) δ1.42 (t, 3H, J=7.1 Hz), 4.42 (q, 2H, J=7.1 Hz), 7.06 (dd, 1H, J=2.1, 8.7 Hz), 7.14–7.22 (m, 5H), 7.38–7.51 (m, 4H), 7.69 (d, 1H, J=8.7 Hz), 7.79 (d, 2H, J=7.1 Hz), 8.67 (d, 1H, J=2.1 Hz), 9.31 (d, 1H, J=2.1 Hz).

Step 4

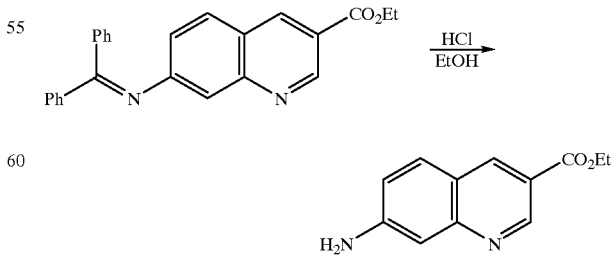

7-Amino-quinoline-3-carboxylic acid ethyl ester

Concentrated hydrochloric acid (1 mL, 2.5 volumes) was added to a solution of 7-(benzhydrylidene-amino)-quinoline-3-carboxylic acid ethyl ester (400 mg, 1.05 mmol, 1 equiv) in ethanol (4 mL, 10 volumes). The solution was stirred at room temperature for three hours and then concentrated. The residue was dissolved in ethyl acetate (20 mL, 50 volumes) and the organic layer was washed with 1 N hydrochloric acid (5×25 mL). The pH of the combined aqueous layer was then adjusted to about 8 with solid sodium hydroxide. The aqueous layer was then extracted with ethyl acetate (3×50 mL). The combined organic layers were dried over sodium sulfate and concentrated to provide 7-amino-quinoline-3-carboxylic acid ethyl ester (155 mg, 68%) as a yellow solid. The crude solid can be further purified by flash column chromatography using silica gel (EM Science, Gibbstown, N.J., 230–400 mesh) in 60% ethyl acetate in hexanes if desired.

MS (APCI) 217 (M+1)$^+$ $^1$H NMR (DMSO-d$_6$) δ1.32 (t, 3H, J=7.0 Hz), 4.31 (q, 2H, J=7.1 Hz), 6.27 (br s, 2H), 6.92 (s, 1H), 7.02 (d, 1H, J=8.7 Hz), 7.77 (d, 1H, J=8.7 Hz), 8.56 (s, 1H), 8.99 (d, 1H, J=2.1 Hz).

Step 5

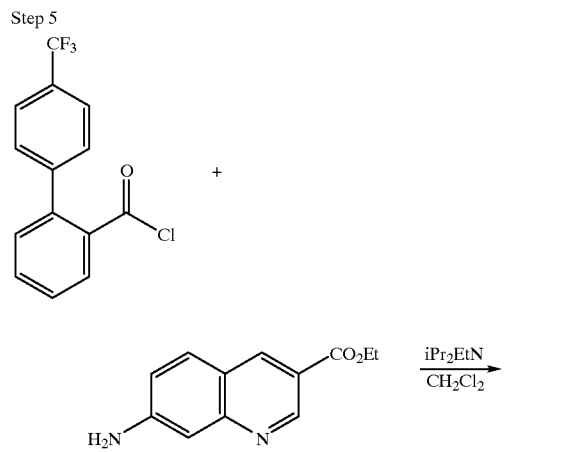

7-[(4'-Trifluoromethyl-biphenyl-2-carbonyl)-amino]-quinoline-3-carboxylic acid ethyl ester To a mixture of 7-amino-quinoline-3-carboxylic acid ethyl ester (11 g, 51 mmol, 1 equiv), dichloroethane (220 mL, 20 volumes), and diisopropylethylamine (13.15 g, 101.7 mmol, 2 equiv) was slowly added a solution of 4'-trifluoromethyl-biphenyl-2-carbonyl chloride (17.38 g, 61 mmol, 1.2 equiv) dissolved in dichloroethane (30 mL, 2.7 volumes). The reaction was heated at 84° C. overnight and then cooled to room temperature. The reaction mixture was washed with 1 N hydrochloric acid (2×150 mL) and the aqueous layer was back extracted with dichloroethane (1×150 mL). The combined organic layers were washed with 1 N sodium hydroxide (2×150 mL), water (150 mL), and saturated sodium chloride (2×150 mL). The combined organic layers were dried over sodium sulfate and concentrated in vacuo to give a red-brown oil. The oil was dissolved in hot toluene (32 mL) and isopropyl ether (16 mL) and the resulting solution was allowed to cool with stirring to give a beige slurry. The solids were collected by filtration to give 7-[(4'-trifluoromethyl-biphenyl-2-carbonyl)-amino]-quinoline-3-carboxylic acid ethyl ester (13.8 g, 58.4 %).

Step 6

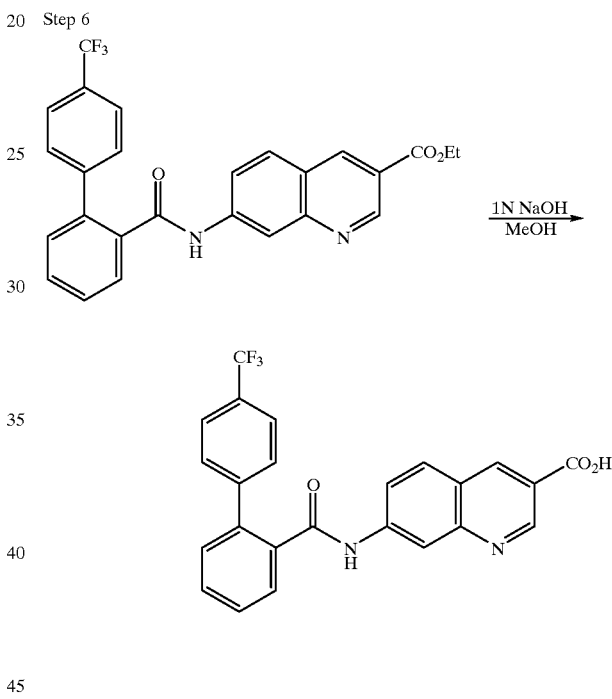

7-[(4'-trifluoromethyl-biphenyl-2-carbonyl)-amino]-quinoline-3-carboxylic acid

To a solution of 7[(4'-trifluoromethyl-biphenyl-2-carbonyl)-amino]-quinoline-3-carboxylic acid ethyl ester (50 g, 114.5 mmol, 1 equiv) and methanol (750 mL, 15 volumes) was slowly added 1 N sodium hydroxide (220 mL, 4.4 volumes). After stirring at room temperature for 2 hours, the reaction was concentrated in vacuo. Water (750 mL) was added to the residue and the pH was adjusted to 5.0 using 1 N hydrochloric acid (250 mL). The resulting slurry was stirred for 30 minutes and the precipitated solids were collected by filtration and dried in vacuo and then dissolved in methanol (75 mL) and ethyl acetate (675 mL). The solution was dried over sodium sulfate and filtered, and concentrated in vacuo. The residue was slurried in ethyl acetate (250 mL). The solids were collected by filtration to give 7-[(4'-trifluoromethyl-biphenyl-2-carbonyl)-amino]-quinoline-3-carboxylic acid (28.1 g, 60 %).

Step 7

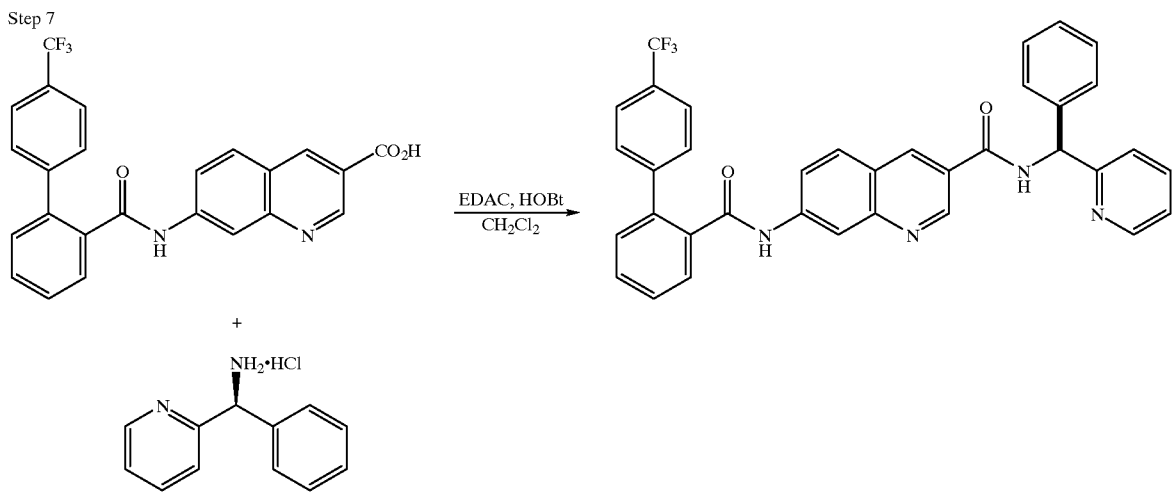

To a suspension of 7-[(4'-trifluoromethyl-biphenyl-2-carbonyl)-amino)]-3-carboxylic acid (10 g, 22.9 mmol, 1 equiv) and methylene chloride (168 mL, 16.8 volumes) was added (S)-phenyl-(2-pyridyl)-methylamine, hydrochloric acid salt (6.5 g, 29.8 mmol, 1.3 equiv), 3-ethyl-1-(3-diethylaminopropyl)-carbodiimide hydrochloride (EDAC) (5.3 g, 27.5 mmol, 1.2 equiv), and hydroxy benzotriazole (HOBT) (3.3 g, 24.1 mmol, 1.05 equiv). Diisopropylethylamine (11.97 g, 92.6 mmol, 4.04 equiv) was added dropwise. The resulting solution was allowed to stir for 12 hours at room temperature. The solution was then extracted with 0.5 N hydrochloric acid (3×80 mL), saturated sodium hydrogen carbonate (2×80 mL) and saturated sodium chloride (80 mL). The organic layer was dried over sodium sulfate and concentrated in vacuo to give (+)-(S)-7-[(4'-trifluoromethyl-biphenyl-2-carbonyl)-amino]-quinoline-3-carboxylic acid (phenyl-pyridin-2-yl-methyl)-amide (12.2 g, 88.4%).

Example 134

(+)-(S)-7-[(4'-trifluoromethyl-biphenyl-2-carbonyl)-amino]-quinoline-3-carboxylic acid (phenyl-pyridin-2-yl-methyl)-amide Step 1

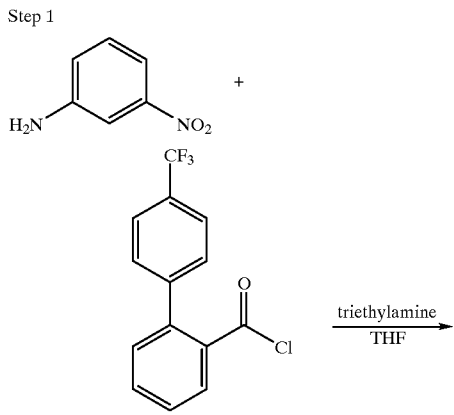

-continued

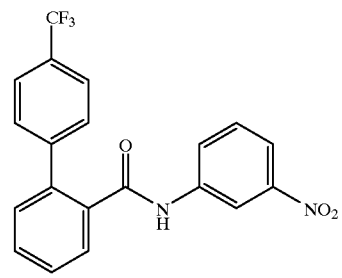

4'-Trifluoromethyl-biphenyl-2-carboxylic acid (3-nitrophenyl)-amide

To a solution of 3-nitroaniline (28.8 g, 209 mmol, 1 equiv) in THF (1000 mL, 35 volumes), was added triethylamine (70 mL, 500 mmol, 2.4 equiv). 3-Nitroaniline can be obtained from Aldrich, Milwaukee, Wis. A solution of 4'-trifluoromethyl-biphenyl-2-carbonyl chloride (71.3 g, 250 mmol, 1.2 equiv) in THF (250 mL, 3.5 volumes) was added dropwise over 30 minutes. The reaction was stirred at room temperature for 48 hours. The slurry was then filtered through diatomaceous earth and the filtrate was concentrated. Water (700 mL, 24 volumes) was added and the slurry was stirred at room temperature for 12 hours. The solids were collected by filtration and dried under vacuum at 40° C. to provide 4'-trifluoromethyl-biphenyl-2-carboxylic acid (3-nitro-phenyl)-amide (80.7 g, 100%) as a pale yellow powder.

MS (APCI) 387 (M+1)$^+$; 385 (M−1)$^-$ $^1$H NMR (DMSO-d$_6$) δ7.25–7.77 (m, 9H), 7.85 (dd, 1 H, J=2.0, 8.3 Hz), 7.92 dd, 1H, J=2.1,7.9Hz), 8.56 (t, 1H, J=2.0Hz), 10.92 (s, 1H).

Step 2

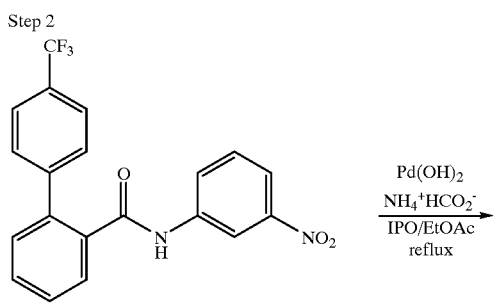

4'-Trifluoromethyl-biphenyl-2-carboxylic acid (3-amino-phenyl)-amide

Ammonium formate (16.3 g, 258 mmol, 3 equiv), followed by Pearlman's catalyst [Pd(OH)$_2$] (6.03 g, 4.30 mmol, 0.05 equiv) was added to a solution of 4'-trifluoromethyl-biphenyl-2-carboxylic acid (3-nitro-phenyl)-amide (33.2 g, 85.9 mmol, 1 equiv) in isopropanol (330 mL, 10 volumes) and ethyl acetate (170 mL, 5 volumes). The mixture was heated at reflux for 3 hours. After cooling, THF (500 mL) was added to the reaction mixture to help solubilize the product. The reaction mixture was filtered through diatomaceous earth and the filtrate was concentrated to about 100 mL. Ethyl acetate (600 mL) and THF (200 mL) were added. The organic layer was washed with saturated sodium bicarbonate solution (300 mL), dried over sodium sulfate, filtered, and concentrated to afford 4'-trifluoromethyl-biphenyl-2-carboxylic acid (3-amino-phenyl)-amide (28.7 g, 94%) as an off-white solid.

MS (APCI) 357 (M+1)$^+$; 355 (M−1)$^-$ $^1$H NMR (DMSO-d$_6$) δ5.00 (br s, 2H), 6.22 (dd, 1H, J=1.7, 9.5 Hz), 6.55 (d, 1H, J=8.7 Hz), 6.84 (t, 1H, J=7.9 Hz), 6.90 (s, 1 H), 7.04–7.61 (m, 6H), 7.73 (d, 2H, J=8.3 Hz), 10.05 (s, 1H).

Step 3

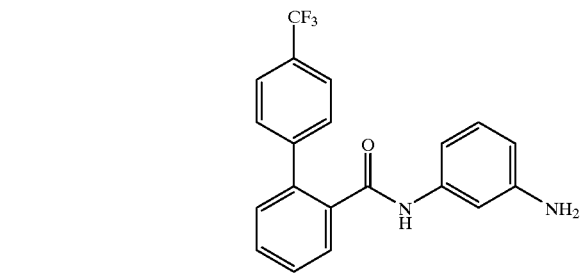

2-Dimethylaminomethylene-1,3-bis(dimethylimmonio) propane bis(tetrafluoroborate)

To a 2 L 3-neck round bottom flask equipped with a reflux condenser and a mechanical stirrer, was added bromoacetic acid (50 g, 360 mmol, 1 equiv) and phosphorus oxychloride (100 mL, 1.08 mol, 3 equiv). The solution was cooled to 0° C. and DMF (167 mL, 2.16 mol, 6 equiv) was added dropwise over 30 minutes via an addition funnel. The resulting solution was heated at 110° C. for 3 hours, then was cooled to 0° C. A solution of aqueous 48% tetrafluoroboric acid in MeOH (200 mL) was added slowly over 1 hour via an addition funnel. Isopropanol (200 mL) was added to the dark viscous solution. Solids precipitated out and the slurry was stirred at 0° C. for 2 hours. The solids were collected by filtration to provide 2-dimethylaminomethylene-1,3-bis (dimethylimmonio)propane bis(tetrafluoroborate) (94.2 g, 73%) as a pale yellow solid.

$^1$H NMR (DMSO-d$_6$) δ3.35 (s, 6H), 3.51 (s, 12H), 8.38 (s, 3H).

Step 4

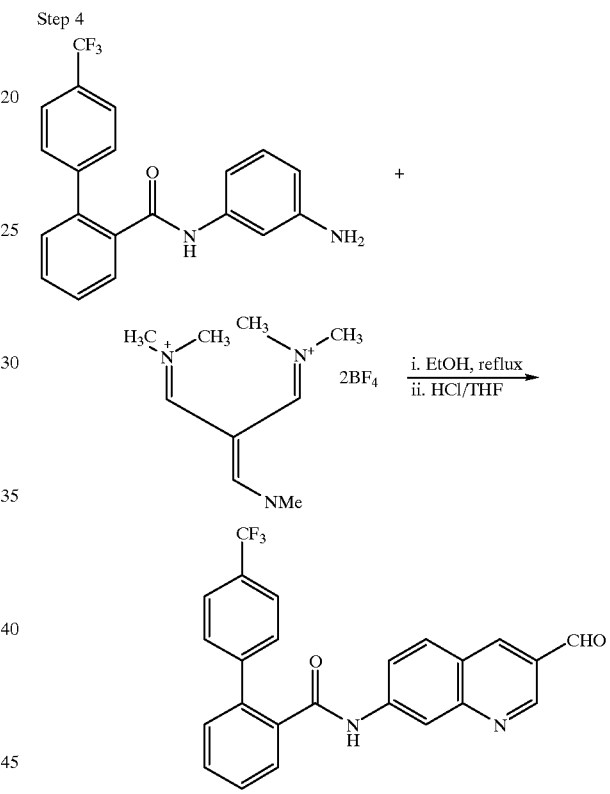

4'-Trifluoromethyl-biphenyl-2-carboxylic acid (3-formyl-quinolin-7-yl)-amide

A slurry of 4'-trifluoromethyl-biphenyl-2-carboxylic acid (3-amino-phenyl)-amide (6.5 g, 18.2 mmol, 1 equiv) and 2-dimethylaminomethylene-1,3-bis(dimethylimmonio) propane bis(tetrafluoroborate) (19.5 g, 54.7 mmol, 3 equiv) in ethanol (200 mL, 30 volumes) was heated at reflux for 24 hours. The reaction became homogeneous after heating for 4 hours. The solution was concentrated and the residue was dissolved in THF (100 mL, 15 volumes) and 1 N HCl (100 mL, 15 volumes). The reaction mixture was stirred at room temperature for 3 hours, then poured into a saturated solution of sodium bicarbonate (100 mL), and extracted with ethyl acetate (2×100 mL). The combined organic layers were dried over sodium sulfate, treated with activated charcoal, filtered, (6.5 g, 1 weight equiv) and concentrated to afford 4'-trifluoromethyl-biphenyl-2-carboxylic acid (3-formyl-quinolin-7-yl)-amide (7.65 g, 100% crude yield) as a yellow foam. The crude product was clean by $^1$H NMR and used in the next step without further purification.

MS (APCI) 421 (M+1)$^+$; 419 (M-1)$^-$ $^1$H NMR (DMSO-d$_6$) δ7.54–7.77 (m, 9H), 8.10 (d, 1H, J=8.7 Hz), 8.46 (s, 1H), 8.80 (d, 1H, J=2.1 Hz), 9.20 (d, 1H, J=2.1 Hz), 10.20 (s, 1H), 10.95 (s, 1H).

Step 5

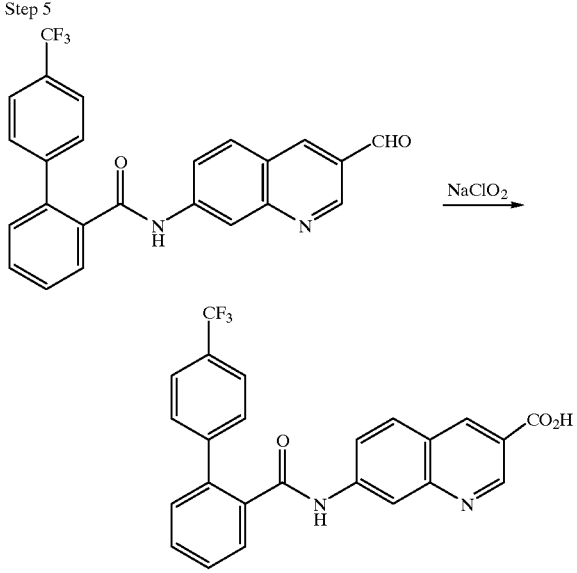

7-[(4'-Trifluoromethyl-biphenyl-2-carbonyl)-amino]-quinoline-3-carboxylic acid

To a solution of 4'-trifluoromethyl-biphenyl-2-carboxylic acid (3-formyl-quinolin-7-yl)-amide (7.65 g, 18.2 mmol, 1 equiv) in acetonitrile (100 mL, 15 volumes) was added an aqueous solution of potassium dihydrogen phosphate (1.25 M, 72.8 mL, 91 mmol, 5 equiv), followed by sodium chlorite (6.17 g, 54.6 mmol, 3 equiv). The slurry was stirred at room temperature for 12 hours. An aqueous solution of sodium sulfite (1 M, 75 mL, 75 mmol, 4.1 equiv) was added and the resulting slurry was stirred at room temperature for 15 minutes. 1 N HCl (50 mL) was added to bring the pH to about 3 to 4. The aqueous layer was extracted with ethyl acetate (2×100 mL). The combined organic layers were dried over sodium sulfate and concentrated to about 75 mL of ethyl acetate. Hexanes (about 75 mL) was added to the slurry and the resulting slurry was allowed to stir at room temperature for 2 hours. The precipitate was collected by filtration to provide 7-[(4'-trifluoromethyl-biphenyl-2-carbonyl)-amino]-quinoline-3-carboxylic acid (6.32 g, 80% over two steps) as a yellow powder.

MS (APCI) 437 (M+1)$^+$; 435 (M-1)$^-$ $^1$H NMR (DMSO-d6) δ7.54–7.74 (m, 9H), 8.08 (d, 1H, J=8.7 Hz), 8.44 (s, 1H), 8.84 (d, 1H, J=1.7 Hz), 9.22 (d, 1H, J=2.0 Hz), 10.90 (s, 1H).

Step 6

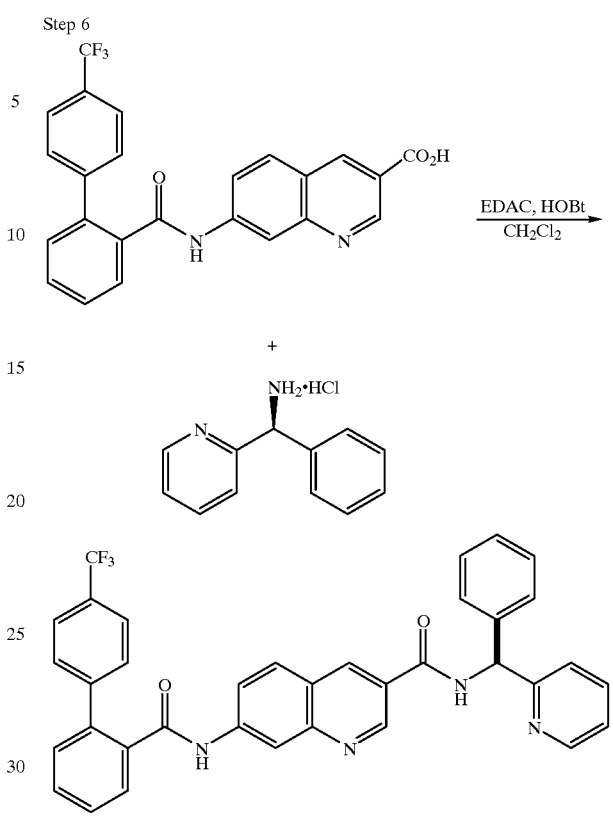

(+)-(S)-7-[(4'-Trifluoromethyl-biphenyl-2-carbonyl)-amino]-quinoline-3-carboxylic acid (phenyl-pyridin-2-yl-methyl)-amide To a suspension of 7-[(4'-trifluoromethyl-biphenyl-2-carbonyl)-amino]-3-carboxylic acid (10 g, 22.9 mmol, 1 equiv) and methylene chloride (168 mL, 16.8 volumes) was added (S)-phenyl-(2-pyridyl)-methylamine, hydrochloric acid salt (6.5 g, 29.8 mmol, 1.3 equiv), 3-ethyl-1-(3-diethylaminopropyl)-carbodiimide hydrochloride (EDAC) (5.3 g, 27.5 mmol, 1.2 equiv), and hydroxy benzotriazole (HOBT) (3.3 g, 24.1 mmol, 1.05 equiv). Diisopropylethylamine (11.97 g, 92.6 mmol, 4.04 equiv) was added dropwise. The resulting solution was allowed to stir for 12 hours at room temperature. The solution was then extracted with 0.5 N hydrochloric acid (3×80 mL), saturated sodium hydrogen carbonate (2×80 mL) and saturated sodium chloride (80 mL). The organic layer was dried over sodium sulfate and concentrated in vacuo to give (+)-(S)-7-[(4'-trifluoromethyl-biphenyl-2-carbonyl)-amino]-quinoline-3-carboxylic acid (phenyl-pyridin-2-yl-methyl)-amide (12.2 g, 88.4%).

Example 135

Resolution of phenyl-(2-pyridyl)-methylamine

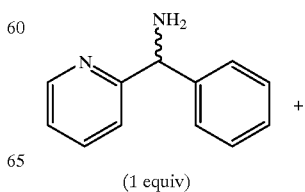

(1 equiv)

-continued

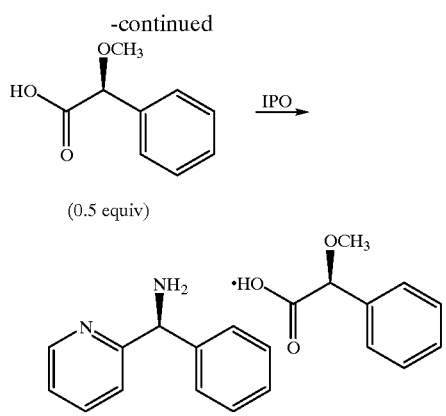

(0.5 equiv)

(S)-Phenyl-(2-pyridyl)-methylamine, (S)-(+)-α-methoxyphenylacetic acid salt (S)-(+)-α-Methoxyphenylacetic acid (22.5 g, 136 mmol, 0.5 equiv) was added to a solution of phenyl-(2-pyridyl)-methylamine (50 g, 271 mmol, 1 equiv) in isopropanol (800 mL, 16 volumes) and a precipitate formed. Racemic phenyl-(2-pyridyl)-methylamine can be obtained from Alfa Aesar, Ward Hill, Mass. After stirring overnight, the precipitate was collected to provide (S)-phenyl-(2-pyridyl)-methylamine, (S)-(+)-α- methoxyphenylacetic acid salt as a 75/25 ratio of enantiomeric salts. Recrystallization of the collected solid in 16 volumes of isopropanol improved the ratio to 95.3/4.7. An additional recrystallization in 10 volumes of ispropanol then improved the ratio to 99.6/0.4. (S)-Phenyl-(2-pyridyl)-methylamine, (S)-(+)-α-methoxyphenylacetic acid salt was isolated as a white solid (16.2 g, 34.2%).

Example 136

(S)-Phenyl-(2-pyridyl)-methylamine, hydrochloride salt

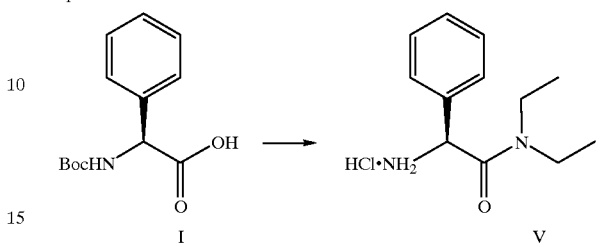

(S)-Phenyl-(2-pyridyl)-methylamine, hydrochloride salt

To a mixture of (S)-phenyl-(2-pyridyl)-methylamine, (S)-α-methoxyphenylacetic acid salt (10 g, 28.5 mmol, 1 equiv) and isopropyl ether (100 mL, 10 volumes) was added 1 N sodium hydroxide (1.14 g, 28.5 mmol, 1 equiv). The mixture was stirred until two transparent layers appeared (1 hour). The layers were separated and the aqueous layer was extracted with isopropyl ether (2×25 mL). The combined organic phases were concentrated in vacuo at 35° to 40° C. to 100 mL. Gaseous HCl (1.6 g, 44.4 mmol, 3 equiv) was bubbled into the solution and white solids precipitated immediately. After stirring the mixture for 15 hours with slow agitation, the solids were collected by filtration and dried in vacuo for 2 hours and 50° C. to give (S)-phenyl-(2-pyridyl)-methylamine, hydrochloric acid salt (5.0 g, 95.5%).

Example 137

7-[(4'-Trifluoromethyl-biphenyl-2-carbonyl)-amino]-quinoline-3-carboxylic acid-S-(diethylcarbamoyl-phenyl-methyl)-amide Step 1

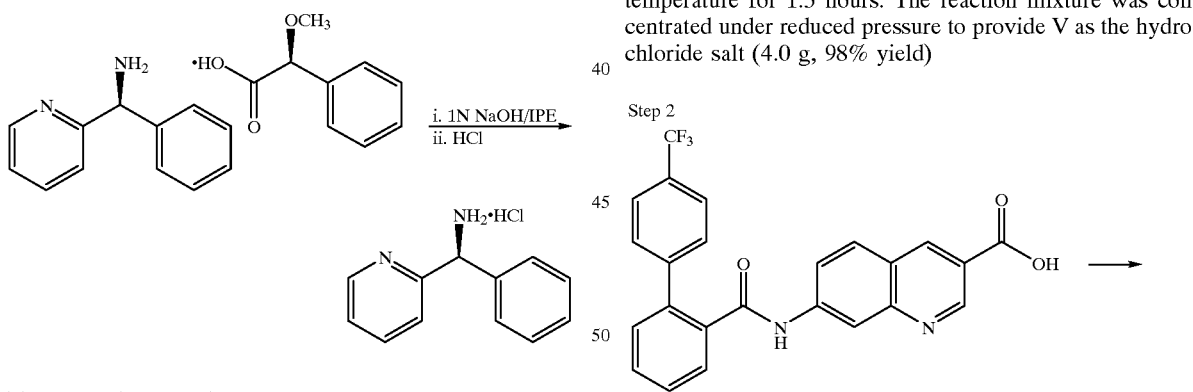

To a solution of Boc-D-phenylglycine I (5 g, 19.9 mmol) and bromo-tris-pyrrolidino-phosphonium hexaflourophosphate (PyBrOP) (9.28 9, 19.9 mmol) and diethylamine amine (2.26 mL, 21.89 mmol) in methylene chloride (70 mL) at 0° C. was added diisopropylethylamine (10.4 mL, 59.7 mmol). The mixture was stirred at 0° C. for 30 minutes and then allowed to warm to room temperature. The mixture stirred at room temperature for 1 hour. The reaction mixture was transferred to a 500 mL separatory flask and diluted with ether (200 mL). The mixture was washed successively with 1N HCl (100 mL), water (50 mL) and brine (50 mL). The ether fraction was dried over magnesium sulfate and filtered. The filtrate was concentrated to a colorless foam. The foam was dissolved in a mixture of 30% ethyl acetate in hexanes and filtered through a pad of silica gel. The silica gel was washed with additional 30% ethyl acetate in hexanes (250 mL). The filtrate was concentrated to provide a colorless solid (6.0 g). The solid was dissolved in 4M HCl in dioxanes (20 mL) and the mixture was stirred at room temperature for 1.5 hours. The reaction mixture was concentrated under reduced pressure to provide V as the hydrochloride salt (4.0 g, 98% yield)

Step 2

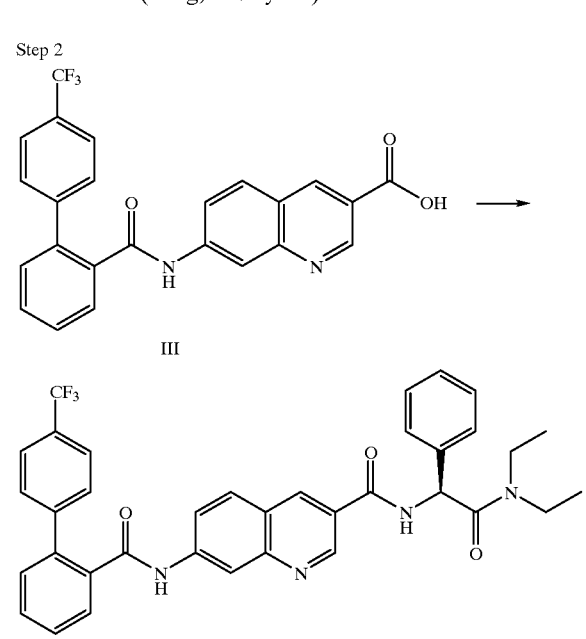

The compound V from step 1 (1.34 g, 6.52 mM), III (2.37 g, 5.4 mM), and PyBrOP (2.52 g, 5.4 mM), were dissolved in DMF (60 mL). The mixture was cooled to 0° C. and then treated with diisopropylethylamine (2.82 mL, 16.2 mM). The mixture was stirred at 0° C. for 30 minutes and then allowed to warm to room temperature, stirring was continued for 24 hours. The mixture was poured into water (200 mL) and the precipitate was collected by vacuum filtration. The solid was dissolved in ethyl acetate (100 mL) and the mixture was dried with magnesium sulfate. The mixture was filtered and the filtrate was concentrated under reduced pressure. The residue was purified by flash chromatography on silica gel eluting with 40% ethyl acetate in hexanes to provide 7-[(4'-trifluoromethyl-biphenyl-2-carbonyl)-amino]-quinoline-3-carboxylic acid-S-(diethylcarbamoyl-phenyl-methyl)-amide (2.92 g, 87%). MS (APCI) 625 (M+1).

Example 138

7-[(4'-Trifluoromethyl-biphenyl-2-carbonyl)-amino]-quinoline-3-carboxylic acid-S-(pentylcarbamoyl-phenyl-methyl)-amide Step 1

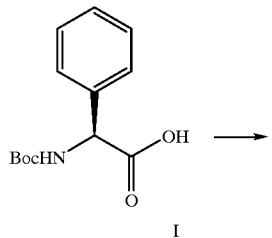

I

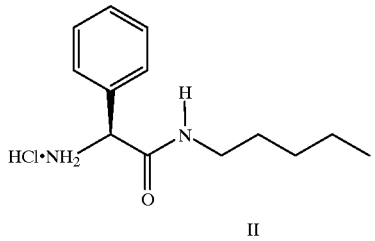

II

To a solution of Boc-D-phenylglycine I (5 g, 19.9 mmol) and bromo-tris-pyrrolidino-phosphonium hexaflourophosphate (PyBrOP) (9.28 g, 19.9 mmol) and amyl amine (2.54 mL, 21.89 mmol) in methylene chloride (70 mL) at 0° C. was added diisopropylethylamine (10.4 mL, 59.7 mmol). The mixture was stirred at 0° C. for 30 minutes and then allowed to warm to room temperature. The mixture stirred at room temperature for 1 hour. The reaction mixture was transferred to a 500 mL separatory flask and diluted with ether (200 mL). The mixture was washed successively with 1 N HCl (100 mL), water (50 mL) and brine (50 mL). The ether fraction was dried over magnesium sulfate and filtered. The filtrate was concentrated to a colorless foam. The foam was dissolved in a mixture of 30% ethyl acetate in hexanes and filtered through a pad of silica gel. The silica gel was washed with additional 30% ethyl acetate in hexanes (250 mL). The filtrate was concentrated to provide a viscous oil (6.37 g). The oil was dissolved in 4M HCl in dioxanes (20 mL) and the mixture was stirred at room temperature for 1.5 hours. The reaction mixture was concentrated under reduced pressure to provide II as the hydrochloride salt (5.1 g, 100% yield).

Step 2

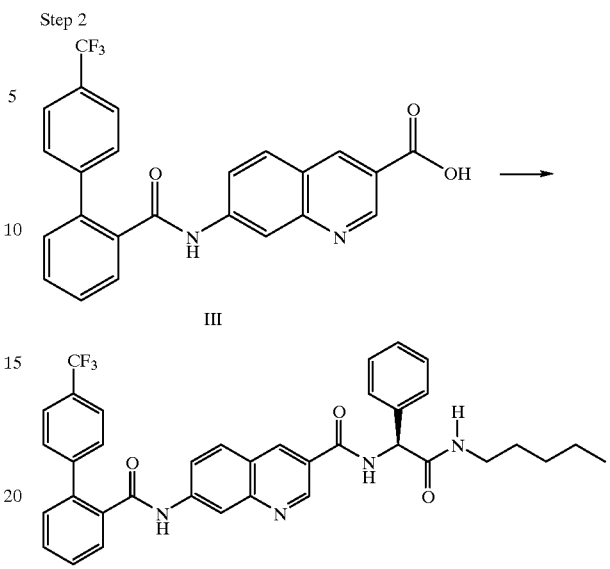

Compound II from Step 1 (1.67 g, 6.52 mM), III (2.37 g, 5.4 mM), and PyBrOP (2.52 g, 5.4 mM), were dissolved in DMF (60 mL). The mixture was cooled to 0° C. and then treated with diisopropylethylamine (2.82 mL, 16.2 mM). The mixture was stirred at 0° C. for 30 minutes and then allowed to warm to room temperature, stirring was continued for 24 hours. The mixture was poured into water (200 mL) and the precipitate was collect by vacuum filtration. The solid was dissolved in ethyl acetate (100 mL) and the mixture was dried with magnesium sulfate. The mixture was filtered and the filtrate was concentrated under reduced pressure. The residue was purified by flash chromatography on silica gel eluting with 50% ethyl acetate in hexanes to provide 7-[(4'-Trifluoromethyl-biphenyl-2-carbonyl)-amino]-quinoline-3-carboxylic acid-S-(pentylcarbamoyl-phenyl-methyl)-amide (3.03 g, 90%). MS (APCI) 639 (M+1).

The following compounds can be synthesized using procedures analogous to those set forth above:
7-[(4'-trifluoromethyl-biphenyl-2-carbonyl)-amino]-quinoline-3-carboxylic acid (pentylcarbamoyl-phenyl-methyl)-amide;
7-[(4'-trifluoromethyl-biphenyl-2-carbonyl)-amino]-quinoline-3-carboxylic acid (diethylcarbamoyl-phenyl-methyl)-amide;
7-[(4'-trifluoromethyl-biphenyl-2-carbonyl)-amino]-quinoline-3-carboxylic acid-S-(pentylcarbamoyl-phenyl-methyl)-amide;
7-[(4'-trifluoromethyl-biphenyl-2-carbonyl)-amino]-quinoline-3-carboxylic acid -S-(diethylcarbamoyl-phenyl-methyl)-amide;
7-[(4'-trifluoromethyl-biphenyl-2-carbonyl)-amino]-quinoline-3-carboxylic acid -R-(pentylcarbamoyl-phenyl-methyl)-amide;
7-[(4'-trifluoromethyl-biphenyl-2-carbonyl)-amino]-quinoline-3-carboxylic acid -R-(diethylcarbamoyl-phenyl-methyl)-amide;
2-methyl-7-[2-(5-trifluoromethyl-pyridin-2-yl)-benzoylamino]-quinoline-3-carboxylic acid (1-pyridin-2-yl-ethyl)-amide;
2-methyl-7-{[2-(4-trifluoromethyl-phenyl)-pyridine-3-carbonyl]-amino}-quinoline-3-carboxylic acid (1-pyridin-2-yl-ethyl)-amide;

2-ethyl-7-[2-(5-trifluoromethyl-pyridin-2-yl)-benzoylamino]-quinoline-3-carboxylic acid (1-pyridin-2-yl-ethyl)-amide;

2-ethyl-7-{[2-(4-trifluoromethyl-phenyl)-pyridine-3-carbonyl]-amino}-quinoline-3-carboxylic acid (1pyridin-2-yl-ethyl)-amide;

7-{[6-methyl-2-(4-trifluoromethyl-phenyl)-pyridine-3-carbonyl]-amino}-quinoline-3-carboxylic acid (1-pyridin-2-yl-ethyl)-amide;

7-[(6-methyl-4'-trifluoromethyl-biphenyl-2-carbonyl)-amino]-quinoline-3-carboxylic acid (1pyridin-2-yl-ethyl)-amide;

7-[3-methyl-2-(5-trifluoromethyl-pyridin-2-yl)-benzoylamino]-quinoline-3-carboxylic acid (1-pyridin-2-yl-ethyl)-amide; and 7-[3,5-dimethyl-2-(5-trifluoromethyl-pyridin-2-yl)-benzoylamino]-quinoline-3-carboxylic acid (1-pyridin-2-yl-ethyl)-amide.

Biological Assays

The utility of the compounds of the present invention as pharmaceutically active agents in the treatment of metabolic diseases (such as are detailed herein) in animals, particularly mammals (e.g. humans) is demonstrated by the activity of the compounds of the present invention in conventional assays and the in vitro and in vivo assays described below. Such assays also provide a means whereby the activities of the compounds of the present invention can be compared with the activities of other known compounds. The results of these comparisons are useful for determining dosage levels.

Apo B Secretion Inhibition/MTP Inhibition Assays

The ability of the compounds of the present invention to inhibit the secretion of apo B and/or inhibit MTP can be determined using the following cell based assay, which measures the secretion of apo B in HepG2 cells.

HepG2 cells (ATCC, HB-8065, Manassas, Va.) are grown in Dulbecco's Modified Eagles Medium plus 10% fetal bovine serum (Growth medium; Gibco, Grand Island, N.Y.) in 96 well culture plates in a humidified atmosphere containing 5% carbon dioxide until they are approximately 70% confluent. Test compounds are dissolved at 10–20 mM in dimethyl sulfoxide, which is then diluted to 1 $\mu$M in growth medium. Serial 1:1 dilutions of this stock are made in growth medium and 100 $\mu$l of each are added to separate wells of a 96-well culture plate containing HepG2 cells. Twenty four hours later, growth medium is collected and assayed by specific enzyme-linked immunosorbent assay (ELISA) for apo B, and as a control, apo Al concentrations. Inhibitors are identified as compounds that decrease apo B secretion into the medium without affecting the secretion of apo Al. The ELISA for apo B is performed as follows. Monoclonal antibody against human apo B (Chemicon, Temecula, Calif.) is diluted to 5 $\mu$g/ml in phosphate buffered saline/azide (PBS+0.02% Na azide) and 100 $\mu$L are added to each well of a 96-well plate (NUNC Maxisorb, Rochester, N.Y.). After an overnight incubation at room temperature, the antibody solution is removed and wells are washed three times with phosphate buffered saline (PBS)/azide. Non-specific sites on the plastic are blocked by incubating wells for 1–3 hours in a solution of 1% (w/v) bovine serum albumin (BSA) made in PBS/azide. 100 $\mu$L of various dilutions of growth medium from the HepG2 cells or apo B standards (made in 0.004% Tween 20/1% BSA in PBS/azide) are added to each well and incubated for 18 hours. Wells are aspirated and washed three times (0.1% Tween 20 in PBS) prior to adding 100 $\mu$L of a 1/1000 dilution of the secondary antibody, goat anti-human apo B (Chemicon). After 3 hours incubation at room temperature, this solution is aspirated and the wells are again washed 3 times as above. 100 $\mu$l of a 1:1600 dilution (in PBS/1% BSA/2 mM MgCl$_2$) of rabbit anti-goat IgG conjugated to alkaline phosphatase (Sigma, Milwaukee, Wis.) are then added to each well and incubated for 1 hour at room temperature. After aspirating, the wells are washed 4 times as above and 100 $\mu$l of 1 mg/ml p-nitrophenylphosphate (pNPP; Sigma) in 25 mM sodium bicarbonate/2mM MgCl$_2$, pH 9.5, are added to each well and incubated for 20–30 minutes and then the reaction is terminated by the addition of 50 $\mu$L of 0.2N NaOH. Absorbance of each well is read at 405 nm and the background at 650 nm is subtracted. Apo B concentration is calculated from a standard curve constructed from purified LDL standards that are run in parallel in the same assay. Apo Al is measured in an analogous manner except that antibodies for apo Al (Chemicon) are used in place of the antibodies for apo B and antigen incubation is at 37° C. instead of room temperature.

Activity of the compounds of the present invention can also be confirmed when a test compound inhibits MTP activity directly. Inhibition of MTP activity by a compound can be quantitated by observing the inhibition of radiolabeled triglyceride from the donor vesicles to acceptor vesicles in the presence of soluble human MTP. The procedures for preparing MTP are based on the method of Wetterau and Zilversmit (*Biochem. Biophys. Acta*, 875: 610 (1986)). Briefly, human liver chunks, frozen at −80° C., are thawed on ice, minced, and rinsed several times with ice cold 0.25M sucrose. All subsequent steps are performed on ice. A 50% homogenate in 0.25 M sucrose is prepared using a Potter-Elvehjem Teflon pestle. The homogenate is diluted 1:1 with 0.25 M sucrose and centrifuged at 10,000×g for 20 minutes at 4° C. The pellet is resuspended in sucrose and recentrifuged at 10,000×g for 20 minutes. The supernatants are combined and the microsomes pelleted by centrifugation at 105,000×g for 75 minutes. The supernatant is decanted and the microsomal pellet is suspended in a minimal volume of 0.25 M sucrose, diluted to 3 ml per gram starting liver weight with 0.15M Tris-HCl, pH 8.0. This suspension is divided into 12 fractions, and centrifuged at 105,000×g for 75 minutes. The supernatants are discarded and the microsomal pellets are stored frozen at −80° C. until needed. For preparation of MTP prior to performing the assay, a thawed pellet is suspended in 12 ml of cold 50 mM Tris-HCl, 50 mM KCl, 5 mM MgCl$_2$, pH 7.4 and 1.2 ml of a 0.54% deoxycholate (pH 7.4) solution is added slowly with mixing to disrupt the microsomal membrane. After 30 minutes incubation on ice with gentle mixing, the suspension is centrifuged at 105,000×g for 75 minutes. The supernatant containing the soluble MTP protein is dialyzed for 2–3 days with 4 changes of assay buffer (150 mM Tris-HCl, 40 mM NaCl, 1 mM EDTA, 0.02% NaN$_3$, pH 7.4). The human liver MTP is stored at 4° C. and diluted 1:5 with assay buffer just before use. MTP preparations show no notable loss of transfer activity with storage up to 30 days.

Liposomes are prepared under nitrogen by room temperature, bath sonication of a dispersion of 400 $\mu$M egg phosphatidylcholine (PC), 75 $\mu$M bovine heart cardiolipin, and 0.82 $\mu$M [$^{14}$C]-triolein (110 Ci/mol) [New England Nuclear, Boston, Mass.] in assay buffer. The lipids in chloroform are mixed together in the proportions outlined above and then dried under a nitrogen stream before hydrating with assay buffer. Acceptor liposomes are prepared under nitrogen by room temperature bath sonication of a dispersion of 1.2 mM PC, 2.3 $\mu$M triolein and 30 pM [$^3$H]-PC (50 Ci/mol) in assay buffer. The donor and acceptor liposomes are centrifuged at 160,000×g for 2 hours at 7° C. The top 80% of the supernatant containing small unilamellar liposomes are carefully removed and stored at 4° C. until used for transfer assays.

MTP activity is measured using a transfer assay that is initiated by mixing donor and acceptor vesicles together with the soluble MTP and test compound. To 100 µl of either a 5% BSA (control) or 5% BSA containing the test compound are added 500 µl assay buffer, 100 µl donor liposomes and 100 µl of diluted MTP protein. After incubation at 37° C. for 45 minutes, triglyceride transfer is terminated by adding 500 µL of a 50% (w/v) diethylaminoethyl (DEAE) cellulose suspension in assay buffer. Following 4 minutes of agitation, the donor liposomes, bound to DEAE cellulose are selectively sedimented by low speed centrifugation (3,000× g; 5 minutes). An aliquot of the supernatant containing the acceptor liposomes is counted and the $^3$H and $^{14}$C counts are used to calculate the percent recovery of acceptor liposomes and the percent triglyceride transfer using first order kinetics. Inhibition of triglyceride transfer by test compound is manifest as a decrease in $^{14}$C radioactivity compared to controls where no test compound is present.

Activity of test compounds as MTP inhibitors can also be measured in vivo according to the following procedure.

Male mice (20–30 g; various strains) are dosed by oral gavage (0.25 ml/25 g body weight) with test compound suspended in an aqueous 0.5% methyl cellulose solution. Compound solutions are dosed either multiple times or over several days, or alternatively, once 90 minutes before mice are euthanized and blood is collected for preparation of serum. The serum is assayed for triglyceride concentration by a commercial enzymatic assay (Triglyceride G: Wako Fine Chemicals, Osaka, Japan). MTP inhibitors are identified by their ability to lower serum triglycerides as compared to control mice dosed with vehicle.

Lp(a) Assay

The utility of apo B secretion/MTP inhibitors in the lowering of blood levels of lipoprotein (a) according to the practice of the methods of the invention may be demonstrated according to protocols disclosed in Nassir, et al., *J. Biol. Chem.*, 273: 17793–17800 (1998), which protocols are summarized below.

Pulse-Chase Studies

Transfected HepG2 cells are grown to 90% confluence in T-25 flasks. On the day of the experiment, the cells are washed twice with phosphate-buffered saline, preincubated in methionine- and cysteine-free DMEM for 1 hour without serum, pulse-labeled for 4 hours in the same medium containing 250 µCi/ml Tran$^{35}$S-label and the apo B secretion/MTP inhibitor and then chased in complete medium containing 3 mM cysteine and 10 mM methionine for up to one hour. The apo B secretion/MTP inhibitor is dissolved in dimethyl sulfoxide at a concentration of 100 mg/ml and diluted to an appropriate concentration in media just prior to incubation with the cells. Control cells receive dimethyl sulfoxide that lacks inhibitor. At appropriate times following radiolabeling, media are collected on ice and adjusted to a final concentration of the following protease inhibitors (100 mM leupeptin, 450 mM apoprotin, 2 mM pepstatin, 1 mM phenylmethylsulfonyl fluoride and 1 mM benzamidine, which can be obtained from Sigma, St. Louis, Mo.). The cells are washed three times with ice-cold, phosphate-buffered saline and subsequently lysed in cold lysis buffer (100 mM Tris, pH 8.0, 100 mM NaCl, 10 mM EDTA, 1% Triton X-100, 0.1% SDS) containing protease inhibitors and, for HepG2 cells, 100 mM ε-aminocaproic acid. Cell lysates and media are clarified by centrifugation at 10,000 rpm at 4° C. for 5 min to remove cellular debris and immunoprecipitations are then conducted as described hereinbelow. Incorporation of radioactivity into total protein is determined by trichloroacetic acid precipitation of cell lysates, in all cases demonstrating comparable values between control and experimental groups.

Immunoprecipitations

Both medium and lysates are precleared by incubation with protein G-agarose (Pharmacia, Piscataway, N.J.) for 2–3 hours at 4° C. Aliquots are immunoprecipitated with saturating quantities of anti-apo(a), anti-apo B, and apoA-I or anti-albumin antisera (Biodesign International, Kennebunk, Me.). After overnight incubation at 4° C., protein G-agarose beads are added and the incubation continued for another 2–3 hours at 4° C. After centrifugation (14,000×g; 4 minutes), the pellet is washed four times in immunoprecipitation wash buffer (50 mM Tris, pH 7.4, 0.65 M NaCl. 10 mM EDTA, 1% Triton X-100, 1% sodium deoxycholate, 01% SDS), two times in water and boiled for 10 minutes in SDS sample buffer (4% SDS, 20% gycerol, 0.001% bromphenol blue, 125 mM Tris, pH 6.8 and 100 mM dithiothreitol). After centrifugation (14,000×g; 4 minutes), the supernatant is analyzed by SDS-PAGE and fluorography.

Combination Assay I

The utility of the apolipoprotein B/microsomal triglyceride transfer protein-glucosidase inhibitor combination in the treatment of conditions resulting from the presence of excess triglycerides, free fatty acids, cholesterol, cholesterol esters or glucose may be demonstrated according to the methodology described by Yamamoto, et al., *Metabolism*, 48 (3): 347–354 (1999).

Standard rat chow (Orinetal Yeast, Tokyo, Japan) is pulverized into a fine powder and a microsomal triglyceride transfer protein inhibitor (75 mg/100 g chow) and a glucosidase inhibitor (75 mg/100 g chow) or a lipase inhibitor (75 mg/100 g chow) are thoroughly mixed. The powderized test compound-chow mixture is reconstituted into pellet form having a normal appearance. The chow for control rats is prepared in a similar fashion but without the addition of test compound. The experimental protocols disclosed in Yamamoto, et al., *Metabolism*, 48 (3): 347–354 (1999) are then followed and the effect of drug treatment on body weight and plasma triglyceride, cholesterol, glucose and insulin levels is determined.

The animals are fed standard rat chow until the start of the experiments. Male spontaneously diabetic rats of the OLETF strain (Kawano, et al., *Diabetes*, 41: 1422–1428, 1992) are randomly divided into four groups at 12 weeks of age (the start of the experiments). Group 1 is maintained on the MTP-glucosidase inhibitor combination-rich rat chow diet described hereinabove from 12 weeks of age, i.e. before the onset of diabetes, until the conclusion of the study at 72 weeks. Group 2 receives standard chow without the MTP-glucosidase inhibitor combination until 28 weeks of age and, thereafter, i.e. following the onset of diabetes, they receive MTP-glucosidase inhibitor combination-rich chow until the conclusion of the study. Group 3 is maintained on a diet containing the MTP-glucosidase inhibitor combination-rich chow from 12 weeks to 28 weeks of age and then standard rat chow without the MTP-glucosidase inhibitor combination-rich chow until 70 weeks of age. Group 4 (control group) receive standard rat chow free of the MTP-glucosidase inhibitor combination.

All groups are permitted ad libitum access to food and water throughout the study. Animals are weighed on a weekly basis and food intake is determined every two weeks over a 48 hour period by weighing the full food cups and then weighing the food cups again 48 hours later, correcting for spillage. The average food intake is estimated as the amount of food consumed per cage. Because the animals are fed as groups and housed two per cage, the value obtained for 48 hours is then divided by four to obtain the approximate estimate of daily food consumption per rat.

At 12, 20, 28, 36, 44, 52, 60 and 70 weeks of age, an intravenous glucose tolerance test is performed after an overnight fast. Animals are weighed before the experiments and anesthesia is induced using sodium pentobarbital (50 mg/kg body weight intraperitoneally). A bolus dose of glucose (200 mg/kg body weight) is injected into the right jugular vein immediately after blood sampling for measurement of serum concentrations of insulin, glucose, triglycerides and cholesterol. Blood samples are collected again from the left jugular vein at 5, 10, 30 and 60 minutes for measurement of serum concentrations of glucose and insulin.

Serum glucose concentrations are determined by the glucose-oxidase method using a glucose kit (Bondar, et al., *Clin. Chim. Acta.*, 20: 586–590, (1974)). Insulin concentrations in the serum are measured by radioimmunoassay using the double-antibody method described in Morgan, et al., *Diabetes,* 12: 115–126, (1963). Serum triglyceride (TG) and cholesterol concentrations are analyzed enzymatically using commercially available kits (Wako TG and cholesterol kits: Wako Pure Chemical, Tokyo, Japan).

Combination Assay II

The utility of the apolipoprotein B/microsomal triglyceride transfer protein-glucosidase inhibitor combination in the treatment of conditions resulting from the presence of excess triglycerides, free fatty acids, cholesterol, cholesterol esters or glucose may be demonstrated according to the methodology described by Hogan, et al., *International Journal of Obesity,* 11, Suppl. 3, 35–42, 1987.

Male Sprague-Dawley rats at 10 weeks of age are given ad libitum access to a moderately high-fat, energy-dense diet (4.7 kcal/g; 19.7 kJ/g) consisting of 47 percent Purina rat chow, 44 percent condensed milk, 8 percent corn oil for 17 weeks. the macronutrient composition by weight of this diet is 14.5 percent fat, 53 percent carbohydrate and 15.8 percent protein. At the start of the study, these animals are judged to be obese, since weight gain over the previous 17 week induction period is 455±12 g versus a gain of 255±7 g in a group of animals (n=36) fed a Purina rat chow diet (4.5 percent fat). A total of 16 animals (818±13 g) are used in the study, half of which receive the apolipoprotein B/microsomal triglyceride transfer protein-lipase inhibitor combination as a dietary admixture for 22 days at an average daily dose of 55 µmol.kg body weight (27 mg/kg).

Body weight and food intake are monitored daily. Intestinal fat absorption is measured by gravimetric determination of dietary and fecal fat, as described by Comai, et al., *J. Nutrition,* 108: 826–835. For these measurements, feces are collected over a 3-day period on two separate occasions, beginning on the eighth and nineteenth day of treatment. At the end of the study, in vivo rates of fatty acid synthesis in the liver and retroperitoneal adipose tissue are measured using [$^3$H] $H_2O$ according to the methodologies of Triscari, et al., *Lipids,* 12: 357–363 and Sperry, et al., *J. Biol. Chem.,* 187: 97–106 and trunk blood was collected for determination of serum parameters.

The use of these methods for assessment of synergy in the treatment of conditions resulting from the presence of excess triglycerides, free fatty acids, cholesterol, cholesterol esters or glucose is deemed appropriate where a quantitative dose-response curve for each individual test compound exists. In this instance, a synergistic response is greater than an additive quantitative response obtained with a combination of two agents compared to the same biological response at a particular dose based on the respective single agent dose-response curve.

Reduction of Intestinal Fat Absorption Assay

The utility of apo B secretion/MTP inhibitors in the reduction of intestinal fat absorption according to the practice of the methods of the invention is demonstrated according to the following protocol.

Healthy, young adult (1–2 years of age) male beagles (Marshall Farms, North Rose, New York, N.Y. 14516) weighing 11.45–12.45 kg at the start of the treatment period are employed as test subjects.

The test compound is provided as a water-soluble powder. The dosing solution, administered by oral gavage, is provided employing a 0.025 M citrate buffer (approx. pH=3) prepared using anyhdrous citric acid (0.4 g/ml) and anhydrous sodium citrate (0.1 g/ml) as the test vehicle. The dosing solution is prepared at 0.5 mg/ml activity so that 1 ml is delivered per kg body weight. Following a fourteen day acclimation period, a sixteen day evaluation study is effected.

The study consists of one group of animals containing five dogs. On Days 0 and 5–12, each dog receives the dosing solution administered as a single dose at Time 0 on each dosing day via a feeding tube. This is followed by a 10 ml water rinse to ensure total delivery of dosing solution. Each test animal is permitted ad libitum access to water and Pedigree Mealtime® (Kal Kan Foods, Inc., Vernon, Calif.) dry food each day during the study, and approximately 1–2 hours post-dose.

Fecal specimens are collected daily over approximately 24 hours (±1 hr) beginning on Day 2 and terminating on Day 16. The fecal specimens so collected are frozen and stored at −26° C. to −20° C. and then analyzed for fecal fat content.

An adaptation of the method of Freidner, et al., *Clin. Chem. Acta,* 18: 345–349 (1967) is employed for the gravimetric determination of fecal fat content. Modifications of the original procedure are as follows: (1) the 5 g fecal fat sample is weighed into a tared 50 ml centrifuge tube, rather than weighing the tube before and after the sample is added, and (2) for shaking, the tubes are placed horizontally on a flatbed shaker rather than being placed upright in a paint can on a paint shaker.

The required number of crystallizing dishes (three per sample) are weighed (to 0.0001 g accuracy). Each fecal sample is thawed overnight at room temperature and then thoroughly mixed to homogeneity by manipulation through the plastic bag. The sample is then flattened in the bag to approximately 1 cm thickness and divided into rectangles about 2 cm×3 cm. Three aliquots (approximately 5 g each) are taken from various sections of the total sample and each is transferred to a tared 50 ml centrifuge tube. Each aliquot was weighed (to 0.01 accuracy), approximately 10 g of glass beads and 10 ml of 0.4% amyl alcohol in absolute ethanol are added to each tube, and the tubes are shaken horizontally for 12 minutes at high speed on a flatbed shaker. The samples are acidified with 3 ml of 2N HCl, and 30 ml of petroleum ether is added. The tubes are shaken as above for 2 minutes and then centrifuged at 1,000 rpm for 5 minutes to separate the phases. A 25 ml aliquot of the petroleum ether layer from each tube is transferred to a pre-weighed crystallizing dish. An additional 25 ml of petroleum ether is added to each tube and the tubes are shaken 1–2 minutes and centrifuged as above. Once more, 25 ml of the petroleum ether layer is transferred to the appropriate crystallizing dish. This step is repeated. The crystallizing dishes are covered with tissue paper and left overnight in a fume hood to allow for evaporation. The following morning, the crystallizing dishes+dry residue are weighed to 0.0001 g accuracy.

The calculations of fecal fat are carried out as follows:
sample wt.=S
residue wt. (R)=(crystallizing dish+residue)−(empty crystallizing dish)
fecal fat (F)=R/S(units are grams fat/gram wet weight)
total fat=F×total grams of bulk feces Reduction of Food Intake Assay The utility of apo B secretion/MTP inhibitors in the reduction of food intake according to the practice of the methods of the invention is demonstrated according to the following protocol.

Healthy, young adult (1–2 years of age) male beagles (Marshall Farms, North Rose, New York, N.Y. 14516) weighing 11.45–12.45 kg at the start of the treatment period are employed as test subjects.

The test compound is provided as a water-soluble powder. The dosing solution, administered by oral gavage, is provided employing a 0.025 M citrate buffer (approx. pH 3) prepared using anyhdrous citric acid (0.4 g/ml) and anhydrous sodium citrate (0.1 g/ml) as the test vehicle. The dosing solution is prepared at 0.5 mg/ml activity so that 1 ml is delivered per kg body weight. Following a fourteen day acclimation period, a sixteen day evaluation study is effected.

The study consists of one group of animals containing five dogs. On Days 0 and 5–12, each dog receives the dosing solution administered as a single dose at Time 0 on each dosing day via a feeding tube. This is followed by a 10 ml water rinse to ensure total delivery of dosing solution. Each test animal is permitted ad libitum access to water and Pedigree Mealtime® (Kal Kan Foods, Inc., Vernon, Calif.) dry food each day during the study and approximately 1–2 hours post-dose.

Reduction in food intake is quantitated by weighing individual food bowls each day prior to feeding at the end of each 24 hour consumption period. The difference between the weight of the empty bowl prior to feeding and the weight of the amount of food remaining in the bowl at the end of the 24 hour consumption period represents the reduction in food intake attributable to the test compound.

What is claimed is:

1. A compound of Formula I

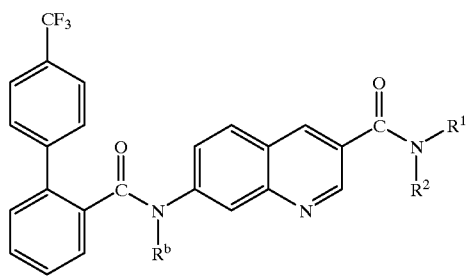

I or a stereoisomer, pharmaceutically acceptable salt or prodrug thereof, or a pharmaceutically acceptable salt of the prodrug,
wherein
each $R^a$ and $R^b$ is independently hydrogen or $C_1$–$C_8$alkyl;
each n is independently 0, 1, 2 or 3;
each X is independently aryl, substituted aryl, heteroaryl, substituted heteroaryl, cycloalkyl, substituted cycloalkyl, heterocycloalkyl, or substitited heterocycloalkyl;

$R^1$ is hydrogen or $C_1$–$C_8$alkyl; and
$R^2$ is hydrogen, —$(CR^aR^a)_n$—X, $C_1$–$C_8$alkyl, $C_1$–$C_8$substituted alkyl,

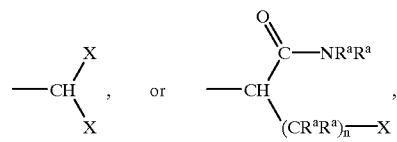

or $R^1$ and $R^2$ together with the nitrogen atom to which they are bonded form a 3 to 7 membered heterocycloalkyl ring having from 1 to 3 heteroatoms.

2. A compound of claim 1 wherein $R^b$ is hydrogen.
3. A compound of claim 1 wherein $R^b$ is hydrogen and $R^1$ is hydrogen.
4. A compound of claim 1 wherein
$R^b$ is hydrogen;
$R^1$ is hydrogen;
$R^2$ is

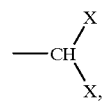

or —$C(R^aR^a)_n$—X; and
each X is independently aryl or heteroaryl.

5. A compound of claim 4 wherein aryl is phenyl and heteroaryl is pyridyl.
6. A compound of claim 4 wherein
$R^2$ is —$C(R^aR^a)_n$—X,
each $R^a$ is independently methyl, ethyl or hydrogen; and
X is phenyl or pyridyl.
7. A compound of claim 1 wherein
$R^b$ is hydrogen;
$R^1$ is hydrogen;
$R^2$ is

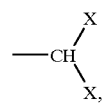

and each X is independently phenyl or pyridyl.

8. A compound of Formula I

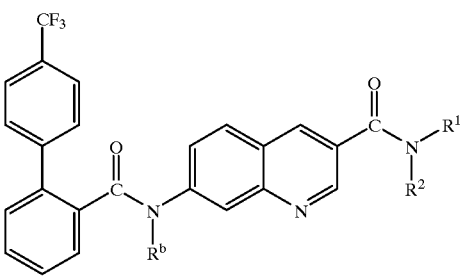

I or a stereoisomer, pharmaceutically acceptable salt or prodrug thereof, or a pharmaceutically acceptable salt of the prodrug, wherein R$^b$ is hydrogen;

R$^1$ is hydrogen;

R$^2$ is hydrogen, C$_1$–C$_8$alkyl, —(CH$_2$)$_n$—Q,

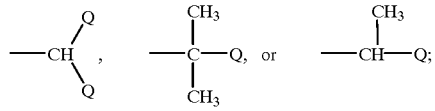

each Q is independently phenyl, pyridyl, substituted phenyl, substituted pyridyl, cycloalkyl, or heterocycloalkyl; and n is 0, 1, 2, or 3.

9. A compound of claim 8 wherein when Q is substituted phenyl or substituted pyridyl, the substituents are selected from —OC$_1$–C$_8$alkyl, C$_1$–C$_8$alkyl or halogen.

10. The compound:

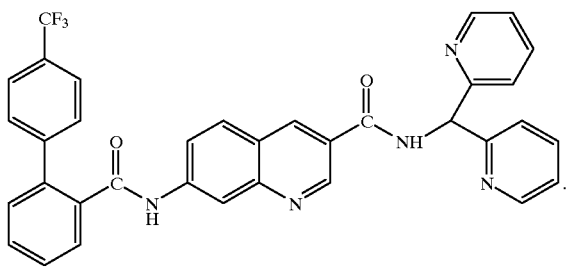

11. The compound:

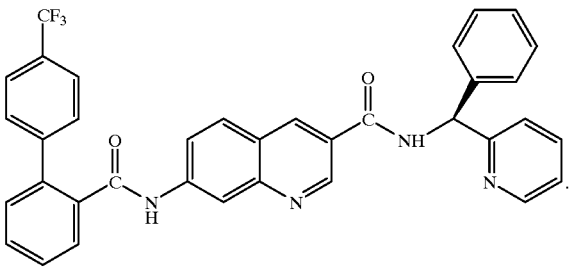

12. The compound:

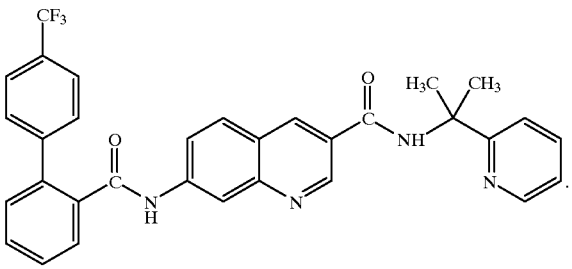

13. The compound:

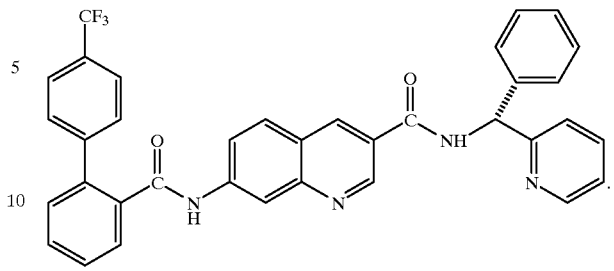

14. The compound:

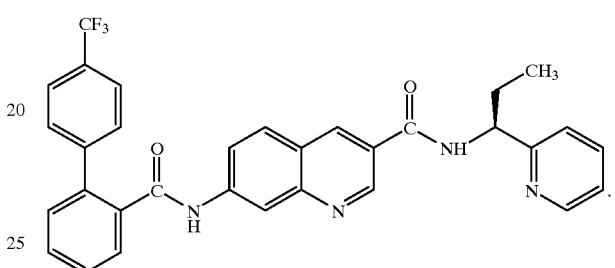

15. The compound:

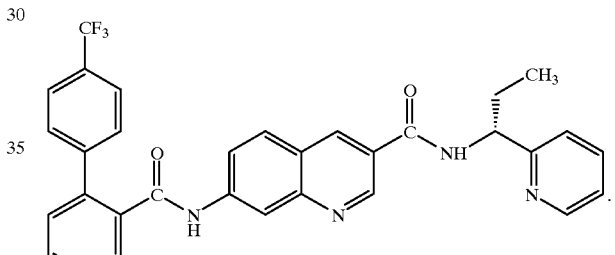

16. A method of inhibiting apolipoprotein B secretion, the method comprising administering to a patient in need of apolipoprotein B secretion inhibition an apolipoprotein B secretion inhibiting amount of a compound of claim 1, or a stereoisomer, pharmaceutically acceptable salt or prodrug thereof, or a pharmaceutically acceptable salt of the prodrug.

17. A method of inhibiting microsomal triglyceride transfer protein, the method comprising administering to a patient in need of microsomal triglyceride transfer protein inhibition a microsomal triglyceride transfer protein inhibiting amount of a compound of claim 1, or a stereoisomer, pharmaceutically acceptable salt or prodrug thereof, or a pharmaceutically acceptable salt of the prodrug.

18. A pharmaceutical composition comprising a compound of claim 1, or a stereoisomer, pharmaceutically acceptable salt or prodrug thereof, or a pharmaceutically acceptable salt of the prodrug, and a pharmaceutically acceptable carrier.

19. The compound:
7-amino-quinoline-3-carboxylic acid ethyl ester;
7-[(4'-trifluoromethyl-biphenyl-2-carbonyl)-amino]-quinoline-3-carboxylic acid ethyl ester; or
7-[(4'-trifluoromethyl-biphenyl-2-carbonyl)-amino]-quinoline-3-carboxylic acid.

20. The compound:
7-[(4'-trifluoromethyl-biphenyl-2-carbonyl)-amino]-quinoline-3-carboxylic acid (dipyridin-2-yl-methyl)-amide;

7-[(4'-trifluoromethyl-biphenyl-2-carbonyl)-amino]-quinoline-3-carboxylic acid (dipyridin-2-yl-methyl)-amide, ethanesulfonate;

7-[(4'-trifluoromethyl-biphenyl-2-carbonyl)-amino]-quinoline-3-carboxylic acid (dipyridin-2-yl-methyl)-amide, bis-ethanesulfonate;

7-[(4'-trifluoromethyl-biphenyl-2-carbonyl)-amino]-quinoline-3-carboxylic acid (phenyl-pyridin-2-yl-methyl)-amide;

7-[(4'-trifluoromethyl-biphenyl-2-carbonyl)-amino]-quinoline-3-carboxylic acid (phenyl-pyridin-2-yl-methyl)-amide, ethanesulfonate;

(S)-7-[(4'-trifluoromethyl-biphenyl-2-carbonyl)-amino]-quinoline-3-carboxylic acid (phenyl-pyridin-2-yl-methyl)-amide;

(S)-7-[(4'-trifluoromethyl-biphenyl-2-carbonyl)-amino]-quinoline-3-carboxylic acid (phenyl-pyridin-2-yl-methyl)-amide, ethanesulfonate;

(S)-7-[(4'-trifluoromethyl-biphenyl-2-carbonyl)-amino]-quinoline-3-carboxylic acid (phenyl-pyridin-2-yl-methyl)-amide, bis-ethanesulfonate;

(R)-7-[(4'-trifluoromethyl-biphenyl-2-carbonyl)-amino]-quinoline-3-carboxylic acid (phenyl-pyridin-2-yl-methyl)-amide;

(R)-7-[(4'-trifluoromethyl-biphenyl-2-carbonyl)-amino]-quinoline-3-carboxylic acid (phenyl-pyridin-2-yl-methyl)-amide, ethanesulfonate; or 7-[(4'-trifluoromethyl-biphenyl-2-carbonyl)-amino]-quinoline-3-carboxylic acid (phenyl-pyridin-2-yl-methyl)-amide, bis-ethanesulfonate, or a stereoisomer, pharmaceutically acceptable salt or prodrug thereof, or a pharmaceutically acceptable salt of the prodrug.

21. The compound:

7-[(4'-trifluoromethyl-biphenyl-2-carbonyl)-amino]-quinoline-3-carboxylic acid (1-carbamoyl-2-phenyl-ethyl)-amide;

7-[(4'-trifluoromethyl-biphenyl-2-carbonyl)-amino]-quinoline-3-carboxylic acid (carbamoyl-phenyl-methyl)-amide;

7-[(4'-trifluoromethyl-biphenyl-2-carbonyl)-amino]-quinoline-3-carboxylic acid propylamide;

7-[(4'-trifluoromethyl-biphenyl-2-carbonyl)-amino]-quinoline-3-carboxylic acid (2,2,2-trifluoro-ethyl)-amide;

7-[(4'-trifluoromethyl-biphenyl-2-carbonyl)-amino]-quinoline-3-carboxylic acid (1-methyl-1-phenyl-ethyl)-amide;

7-[(4'-trifluoromethyl-biphenyl-2-carbonyl)-amino]-quinoline-3-carboxylic acid cyclopentylamide;

7-[(4'-trifluoromethyl-biphenyl-2-carbonyl)-amino]-quinoline-3-carboxylic acid (1-phenyl-propyl)-amide;

(R)-7-[(4'-trifluoromethyl-biphenyl-2-carbonyl)-amino]-quinoline-3-carboxylic acid (1-phenyl-ethyl)-amide, ethanesulfonate; or 7-[(4'-trifluoromethyl-biphenyl-2-carbonyl)-amino]-quinoline-3-carboxylic acid (1-phenyl-ethyl)-amide, ethanesulfonate, or a stereoisomer, pharmaceutically acceptable salt or prodrug thereof, or a pharmaceutically acceptable salt of the prodrug.

22. The compound:

7-[(4'-trifluoromethyl-biphenyl-2-carbonyl)-amino]-quinoline-3-carboxylic acid (1-pyridin-2-yl-propyl)-amide;

(R)-7-[(4'-trifluoromethyl-biphenyl-2-carbonyl)-amino]-quinoline-3-carboxylic acid (1-pyridin-2-yl-propyl)-amide;

(R)-7-[(4'-trifluoromethyl-biphenyl-2-carbonyl)-amino]-quinoline-3-carboxylic acid (1-pyridin-2-yl-propyl)-amide, ethanesulfonate;

(S)-7-[(4'-trifluoromethyl-biphenyl-2-carbonyl)-amino]-quinoline-3-carboxylic acid (1-pyridin-2-yl-propyl)-amide;

(S)-7-[(4'-trifluoromethyl-biphenyl-2-carbonyl)-amino]-quinoline-3-carboxylic acid (1-pyridin-2-yl-propyl)-amide ethanesulfonate;

7-[(4'-trifluoromethyl-biphenyl-2-carbonyl)-amino]-quinoline-3-carboxylic acid (1-pyridin-2-yl-propyl)-amide, ethanesulfonate;

7-[(4'-trifluoromethyl-biphenyl-2-carbonyl)-amino]-quinoline-3-carboxylic acid (pyridin-2-ylmethyl)-amide, ethanesulfonate;

7-[(4'-trifluoromethyl-biphenyl-2-carbonyl)-amino]-quinoline-3-carboxylic acid (2-pyridin-2-yl-ethyl)-amide, ethanesulfonate;

7-[(4'-trifluoromethyl-biphenyl-2-carbonyl)-amino]-quinoline-3-carboxylic acid ethylamide, ethanesulfonate; or 7-[(4'-trifluoromethyl-biphenyl-2-carbonyl)-amino]-quinoline-3-carboxylic acid butylamide, ethanesulfonate, or a stereoisomer, pharmaceutically acceptable salt or prodrug thereof, or a pharmaceutically acceptable salt of the prodrug.

23. The compound:

7-[(4'-trifluoromethyl-biphenyl-2-carbonyl)-amino]-quinoline-3-carboxylic acid (thiophen-2-ylmethyl)-amide, ethanesulfonate;

7-[(4'-trifluoromethyl-biphenyl-2-carbonyl)-amino]-quinoline-3-carboxylic acid (1-methyl-1pyridin-2-yl-ethyl)-amide;

(S)-7-[(4'-trifluoromethyl-biphenyl-2-carbonyl)-amino]-quinoline-3-carboxylic acid (1-pyridin-2-yl-ethyl)-amide;

(R)-7-[(4'-trifluoromethyl-biphenyl-2-carbonyl)-amino]-quinoline-3-carboxylic acid (1-pyridin-2-yl-ethyl)-amide ethanesulfonate;

7-[(4'-trifluoromethyl-biphenyl-2-carbonyl)-amino]-quinoline-3-carboxylic acid (1-pyridin-2-yl-ethyl)-amide;

7-[(4'-trifluoromethyl-biphenyl-2-carbonyl)-amino]-quinoline-3-carboxylic acid (1-pyridin-2-yl-ethyl)-amide ethanesulfonate;

7-[(4'-trifluoromethyl-biphenyl-2-carbonyl)-amino]-quinoline-3-carboxylic acid amide;

7-[(4'-trifluoromethyl-biphenyl-2-carbonyl)-amino]-quinoline-3-carboxylic acid benzylamide;

7-[(4'-trifluoromethyl-biphenyl-2-carbonyl)-amino]-quinoline-3-carboxylic acid 4-methoxy-benzylamide;

7-[(4'-trifluoromethyl-biphenyl-2-carbonyl)-amino]-quinoline-3-carboxylic acid 4-chloro-benzylamide;

7-[(4'-trifluoromethyl-biphenyl-2-carbonyl)-amino]-quinoline-3-carboxylic acid 4-methyl-benzylamide; or 7-[(4'-trifluoromethyl-biphenyl-2-carbonyl)-amino]-quinoline-3-carboxylic acid cyclopropylmethyl-amide, or a stereoisomer, pharmaceutically acceptable salt or prodrug thereof, or a pharmaceutically acceptable salt of the prodrug.

24. The compound:

7-[(4'-trifluoromethyl-biphenyl-2-carbonyl)-amino]-quinoline-3-carboxylic acid 4-fluoro-benzylamide;

7-[(4'-trifluoromethyl-biphenyl-2-carbonyl)-amino]-quinoline-3-carboxylic acid isopropyl-amide;

7-[(4'-trifluoromethyl-biphenyl-2-carbonyl)-amino]-quinoline-3-carboxylic acid benzhydryl-amide;

7-[(4'-trifluoromethyl-biphenyl-2-carbonyl)-amino]-quinoline-3-carboxylic acid cyclopropylamide;

7-[(4'-trifluoromethyl-biphenyl-2-carbonyl)-amino]-quinoline-3-carboxylic acid [1(4-fluoro-phenyl)-ethyl]-amide;

7-[(4'-trifluoromethyl-biphenyl-2-carbonyl)-amino]-quinoline-3-carboxylic acid 3-methyl-benzylamide; or
7-[(4'-trifluoromethyl-biphenyl-2-carbonyl)-amino]-quinoline-3-carboxylic acid 3-methoxy-benzylamide, or a stereoisomer, pharmaceutically acceptable salt or prodrug thereof, or a pharmaceutically acceptable salt of the prodrug.

25. The compound:
7-[(4'-trifluoromethyl-biphenyl-2-carbonyl)-amino]-quinoline-3-carboxylic acid 3-chloro-benzylamide;
7-[(4'-trifluoromethyl-biphenyl-2-carbonyl)-amino]-quinoline-3-carboxylic acid 2-fluoro-benzylamide;
7-[(4'-trifluoromethyl-biphenyl-2-carbonyl)-amino]-quinoline-3-carboxylic acid 3-fluoro-benzylamide;
7-[(4'-trifluoromethyl-biphenyl-2-carbonyl)-amino]-quinoline-3-carboxylic acid 2-methyl-benzylamide;
7-[(4'-trifluoromethyl-biphenyl-2-carbonyl)-amino]-quinoline-3-carboxylic acid 2-methoxy-benzylamide;
7-[(4'-trifluoromethyl-biphenyl-2-carbonyl)-amino]-quinoline-3-carboxylic acid 2-chloro-benzylamide;
4'-trifluoromethyl-biphenyl-2-carboxylic acid [3-(pyrrolidine-1-carbonyl)-quinolin-7-yl]-amide;
4'-trifluoromethyl-biphenyl-2-carboxylic acid [3-(morpholine-4-carbonyl)-quinolin-7-yl]-amide;
7-[(4'-trifluoromethyl-biphenyl-2-carbonyl)-amino]-quinoline-3-carboxylic acid diethylamide; or
4'-trifluoromethyl-biphenyl-2-carboxylic acid [3-(piperidine-1-carbonyl)-quinolin-7-yl]-amide, or a stereoisomer, pharmaceutically acceptable salt or prodrug thereof, or a pharmaceutically acceptable salt of the prodrug.

26. A compound of Formula II

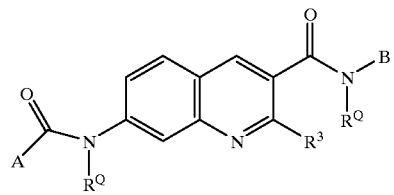

II or a stereoisomer, pharmaceutically acceptable salt or prodrug thereof, or a pharmaceutically acceptable salt of the prodrug,
wherein
each $R^3$ is independently hydrogen or $C_1$–$C_6$alkyl;
each $R^Q$ is independently hydrogen or $C_1$–$C_6$alkyl;
A is

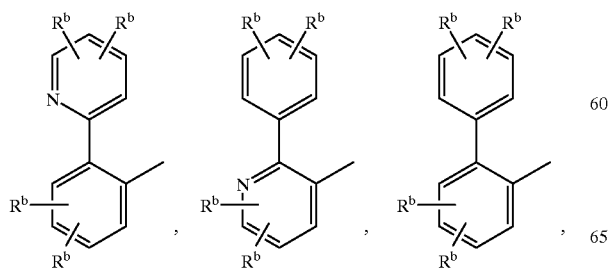

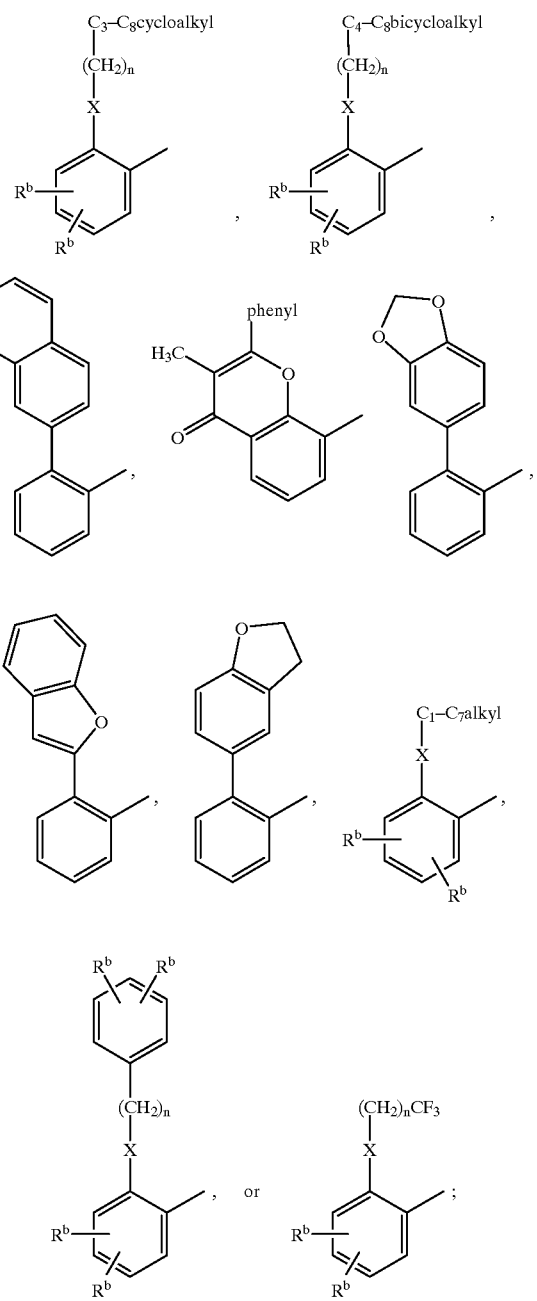

X is O or S;

n is 0 to 6;

each $R^b$ is independently hydrogen, —$CF_3$, —$OC_1$–$C_6$alkyl, halo, —SH, —$SC_1$–$C_6$alkyl, phenyl, or —$C_1$–$C_6$alkyl;

B is hydrogen,

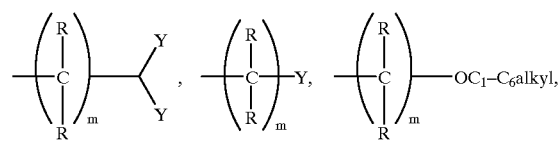

-continued

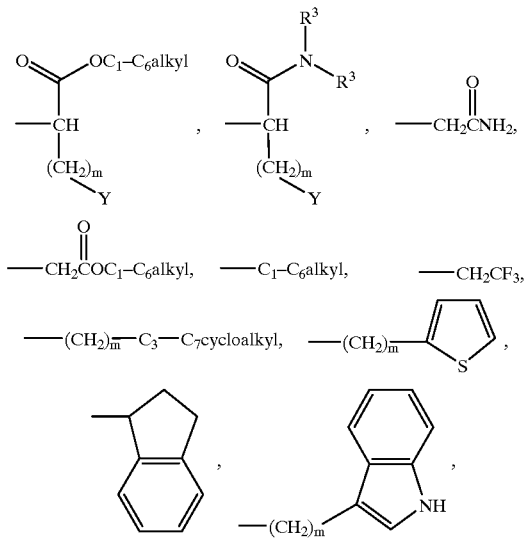

or B and $R^Q$ together with the nitrogen atom to which they are bonded form a heterocycloalkyl ring having from 1 to 3 heteroatoms;

each R is independently hydrogen or $C_1$–$C_6$alkyl;

each Y is independently phenyl, substituted phenyl, pyridyl or substituted pyridyl, wherein any substituents are independently selected from —$CF_3$, halo, —$OC_1$–$C_6$alkyl, or —$C_1$–$C_6$alkyl; and m is 0 to 5.

27. A compound of claim 26 wherein A is

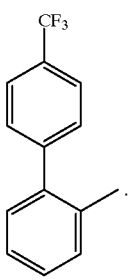

28. A compound of claim 26 wherein each $R^Q$ is hydrogen.
29. A compound of claim 26 wherein $R^3$ is hydrogen.
30. A compound of claim 26 wherein B is

and each Y is independently phenyl or pyridyl.

31. The compound:
7-[(4'-trifluoromethyl-biphenyl-2-carbonyl)-amino]-quinoline-3-carboxylic acid [bis-(4-fluoro-phenyl)-methyl]-amide;
7-[(4'-trifluoromethyl-biphenyl-2-carbonyl)-amino]-quinoline-3-carboxylic acid benzyl-ethyl-amide;
7-[(4'-trifluoromethyl-biphenyl-2-carbonyl)-amino]-quinoline-3-carboxylic acid (3-phenyl-propyl)-amide;
7-[(4'-trifluoromethyl-biphenyl-2-carbonyl)-amino]-quinoline-3-carboxylic acid ethyl-pyridin-2-ylmethyl-amide;
7-[(4'-trifluoromethyl-biphenyl-2-carbonyl)-amino]-quinoline-3-carboxylic acid phenethyl-amide;
7-[(4'-trifluoromethyl-biphenyl-2-carbonyl)-amino]-quinoline-3-carboxylic acid phenylamide;
7-[(4'-trifluoromethyl-biphenyl-2-carbonyl)-amino]-quinoline-3-carboxylic acid (2-methoxy-ethyl)-amide;
7-[(4'-trifluoromethyl-biphenyl-2-carbonyl)-amino]-quinoline-3-carboxylic acid (1-methyl-3-phenyl-propyl)-amide;
7-[(4'-trifluoromethyl-biphenyl-2-carbonyl)-amino]-quinoline-3-carboxylic acid indan-1-ylamide;
7-[(4'-trifluoromethyl-biphenyl-2-carbonyl)-amino]-quinoline-3-carboxylic acid (3,3-diphenyl-propyl)-amide;
7-[(4'-trifluoromethyl-biphenyl-2-carbonyl)-amino]-quinoline-3-carboxylic acid [2-(1H-indol-3-yl)-ethyl]-amide;
7-[(4'-trifluoromethyl-biphenyl-2-carbonyl)-amino]-quinoline-3-carboxylic acid (4-phenyl-butyl)-amide;
[R]-7-[(4'-trifluoromethyl-biphenyl-2-carbonyl)-amino]-quinoline-3-carboxylic acid [(4-fluoro-phenyl)-pyridin-2-yl-methyl]-amide;
[S]-7-[(4'-trifluoromethyl-biphenyl-2-carbonyl)-amino]-quinoline-3-carboxylic acid [(4-fluoro-phenyl)-pyridin-2-yl-methyl]-amide;
2-methyl-7-[(4'-trifluoromethyl-biphenyl-2-carbonyl)-amino]-quinoline-3-carboxylic acid (2-methoxy-ethyl)-amide;
[S]-2-methyl-7-[(4'-trifluoromethyl-biphenyl-2-carbonyl)-amino]-quinoline-3-carboxylic acid (phenyl-pyridin-2-yl-methyl)-amide;
[R]-7-[2-(5-trifluoromethyl-pyridin-2-yl)-benzoylamino]-quinoline-3-carboxylic acid (1-pyridin-2-yl-propyl)-amide;
[R]-7-[2-(5-trifluoromethyl-pyridin-2-yl)-benzoylamino]-quinoline-3-carboxylic acid (1-pyridin-2-yl-ethyl)-amide;
[S]-7-[2-(5-trifluoromethyl-pyridin-2-yl)-benzoylamino]-quinoline-3-carboxylic acid (phenyl-pyridin-2-yl-methyl)-amide;
[R]-7-[2-(6-methyl-pyridin-3-yl)-benzoylamino]-quinoline-3-carboxylic acid (1-pyridin-2-yl-ethyl)-amide;
[R]7-[2-(5-methyl-pyridin-2-yl)-benzoylamino]-quinoline-3-carboxylic acid (1-pyridin-2-yl-ethyl)-amide;
[S]-7-{[2-(4-trifluoromethyl-phenyl)-pyridine-3-carbonyl]-amino}-quinoline-3-carboxylic acid (phenyl-pyridin-2-yl-methyl)-amide;
[R]-7-{[2-(4-trifluoromethyl-phenyl)-pyridine-3-carbonyl]-amino}-quinoline-3-carboxylic acid (1-pyridin-2-yl-ethyl)-amide;
[R]-7-{[2-(4-trifluoromethyl-phenyl)-pyridine-3-carbonyl]-amino}-quinoline-3-carboxylic acid (1-pyridin-2-yl-propyl)-amide;
[R]-7-[(2-p-tolyl-pyridine-3-carbonyl)-amino]-quinoline-3-carboxylic acid (1-pyridin-2-yl-ethyl)-amide;
[R]-7-{[2-(4-isopropyl-phenyl)-pyridine-3-carbonyl]-amino}-quinoline-3-carboxylic acid (1pyridin-2-yl-ethyl)-amide;
[R]-7-{[2-(4-tert-butyl-phenyl)-pyridine-3-carbonyl]-amino}-quinoline-3-carboxylic acid (1-pyridin-2-yl-ethyl)-amide;
[R]-7-{[2-(4-methoxy-phenyl)-pyridine-3-carbonyl]-amino}-quinoline-3-carboxylic acid (1pyridin-2-yl-ethyl)-amide;
[R]-7-{[2-(4-ethyl-phenyl)-pyridine-3-carbonyl]-amino}-quinoline-3-carboxylic acid (1-pyridin-2-yl-ethyl)-amide;
7-[(4'-tert-butyl-biphenyl-2-carbonyl)-amino]-quinoline-3-carboxylic acid (phenyl-pyridin-2-yl-methyl)-amide;
7-[(biphenyl-2-carbonyl)-amino]-quinoline-3-carboxylic acid (phenyl-pyridin-2-yl-methyl)-amide;

7-[(biphenyl-2-carbonyl)-amino]-quinoline-3-carboxylic acid (1-pyridin-2-yl-propyl)-amide;
7-[(biphenyl-2-carbonyl)-amino]-quinoline-3-carboxylic acid (di-pyridin-2-yl-methyl)-amide;
7-[(4'-methyl-biphenyl-2-carbonyl)-amino]-quinoline-3-carboxylic acid acid (phenyl-pyridin-2-yl-methyl)-amide;
7-[(4'-methyl-biphenyl-2-carbonyl)-amino]-quinoline-3-carboxylic acid acid (di-pyridin-2-yl-methyl)-amide;
7-[(4'-methyl-biphenyl-2-carbonyl)-amino]-quinoline-3-carboxylic acid acid (1-pyridin-2-yl-propyl)-amide;
7-(2-benzofuran-2-yl-benzoylamino)-quinoline-3-carboxylic acid (phenyl-pyridin-2-yl-methyl)-amide;
7-[(4'-isopropyl-biphenyl-2-carbonyl)-amino]-quinoline-3-carboxylic acid (di-pyridin-2-yl-methyl)-amide;
7-[(4'-isopropyl-biphenyl-2-carbonyl)-amino]-quinoline-3-carboxylic acid acid (phenyl-pyridin-2-yl-methyl)-amide;
7-[(4'-isopropyl-biphenyl-2-carbonyl)-amino]-quinoline-3-carboxylic acid (1pyridin-2-yl-propyl)-amide;
7-[(3'-methyl-biphenyl-2-carbonyl)-amino]-quinoline-3-carboxylic acid acid (phenyl-pyridin-2-yl-methyl)-amide;
7-[(4'-ethyl-biphenyl-2-carbonyl)-amino]-quinoline-3-carboxylic acid (phenyl-pyridin-2-yl-methyl)-amide;
7-[(4'-ethyl-biphenyl-2-carbonyl)-amino]-quinoline-3-carboxylic acid (1pyridin-2-yl-propyl)-amide;
7-[(4'-tert-butyl-biphenyl-2-carbonyl)-amino]-quinoline-3-carboxylic acid (1pyridin-2-yl-propyl)-amide;
7-[(4'-ethylsulfanyl-biphenyl-2-carbonyl)-amino]-quinoline-3-carboxylic acid (phenyl-pyridin-2-yl-methyl)-amide;
7-[(4'-ethylsulfanyl-biphenyl-2-carbonyl)-amino]-quinoline-3-carboxylic acid (1-pyridin-2-yl-propyl)-amide;
7-(2-naphthalen-2-yl-benzoylamino)-quinoline-3-carboxylic acid (phenyl-pyridin-2-yl-methyl)-amide;
7-(2-benzo[1,3]dioxol-5-yl-benzoylamino)-quinoline-3-carboxylic acid (phenyl-pyridin-2-yl-methyl)-amide;
7-[(3',4'-dimethyl-biphenyl-2-carbonyl)-amino]-quinoline-3-carboxylic acid (phenyl-pyridin-2-yl-methyl)-amide;
7-[(2'-methyl-biphenyl-2-carbonyl)-amino]-quinoline-3-carboxylic acid (phenyl-pyridin-2-yl-methyl)-amide;
7-[(3'-fluoro-4'-methyl-biphenyl-2-carbonyl)-amino]-quinoline-3-carboxylic acid (phenyl-pyridin-2-yl-methyl)-amide;
7-[(4'-ethoxy-biphenyl-2-carbonyl)-amino]-quinoline-3-carboxylic acid (phenyl-pyridin-2-yl-methyl)-amide;
7-[(4'-ethoxy-biphenyl-2-carbonyl)-amino]-quinoline-3-carboxylic acid (1-pyridin-2-yl-propyl)-amide;
7-[(4'-ethoxy-biphenyl-2-carbonyl)-amino]-quinoline-3-carboxylic acid (di-pyridin-2-yl-methyl)-amide;
7-[2-(2,3-dihydro-benzofuran-5-yl)-benzoylamino]-quinoline-3-carboxylic acid (phenyl-pyridin-2-yl-methyl)-amide;
7-[(4'-propoxy-biphenyl-2-carbonyl)-amino]-quinoline-3-carboxylic acid (phenyl-pyridin-2-yl-methyl)-amide;
7-[(4'-propoxy-biphenyl-2-carbonyl)-amino]-quinoline-3-carboxylic acid (1pyridin-2-yl-propyl)-amide;
7-[(4'-butoxy-biphenyl-2-carbonyl)-amino]-quinoline-3-carboxylic acid (phenyl-pyridin-2-yl-methyl)-amide;
7-[(4'-butoxy-biphenyl-2-carbonyl)-amino]-quinoline-3-carboxylic acid (1pyridin-2-yl-propyl)-amide;
7-[(3-methyl-4-oxo-2-phenyl-4H-chromene-8-carbonyl)-amino]-quinoline-3-carboxylic acid (1-pyridin-2-yl-propyl)-amide;
7-[(3-methyl-4-oxo-2-phenyl-4H-chromene-8-carbonyl)-amino]-quinoline-3-carboxylic acid (phenyl-pyridin-2-yl-methyl)-amide;
7-[(3-methyl-4-oxo-2-phenyl-4H-chromene-8-carbonyl)-amino]-quinoline-3-carboxylic acid (di-pyridin-2-yl-methyl)-amide;
7-(2-cyclohexylmethoxy-benzoylamino)-quinoline-3-carboxylic acid (di-pyridin-2-yl-methyl)-amide;
7-(2-cyclohexylmethoxy-benzoylamino)-quinoline-3-carboxylic acid (phenyl-pyridin-2-yl-methyl)-amide;
7-(2-cyclohexylmethoxy-benzoylamino)-quinoline-3-carboxylic acid (1pyridin-2-yl-propyl)-amide;
7-(2-cyclohexylmethoxy-3-methoxy-benzoylamino)-quinoline-3-carboxylic acid (phenyl-pyridin-2-yl-methyl)-amide;
7-(2-cyclohexylmethoxy-3-methoxy-benzoylamino)-quinoline-3-carboxylic acid (di-pyridin-2-yl-methyl)-amide;
7-(2-cyclohexylmethoxy-3-methoxy-benzoylamino)-quinoline-3-carboxylic acid (1-pyridin-2-yl-propyl)-amide;
7-[2-(bicyclo[2.2.1]hept-2-ylmethoxy)-benzoylamino]-quinoline-3-carboxylic acid (di-pyridin-2-yl-methyl)-amide;
7-[2-(bicyclo[2.2.1]hept-2-ylmethoxy)-benzoylamino]-quinoline-3-carboxylic acid (phenyl-pyridin-2-yl-methyl)-amide;
7-[2-(bicyclo[2.2.1]hept-2-ylmethoxy)-benzoylamino]-quinoline-3-carboxylic acid (1-pyridin-2-yl-propyl)-amide;
7-[2-(bicyclo[2.2.1]hept-2-ylmethoxy)-3-methoxy-benzoylamino]-quinoline-3-carboxylic acid (di-pyridin-2-yl-methyl)-amide;
7-[2-(bicyclo[2.2.1]hept-2-ylmethoxy)-3-methoxy-benzoylamino]-quinoline-3-carboxylic acid (phenyl-pyridin-2-yl-methyl)-amide;
7-[2-(bicyclo[2.2.1]hept-2-ylmethoxy)-3-methoxy-benzoylamino]-quinoline-3-carboxylic acid (1-pyridin-2-yl-propyl)-amide;
7-(2-pentyloxy-benzoylamino)-quinoline-3-carboxylic acid (di-pyridin-2-yl-methyl)-amide;
7-(2-pentyloxy-benzoylamino)-quinoline-3-carboxylic (phenyl-pyridin-2-yl-methyl)-amide;
7-(2-pentyloxy-benzoylamino)-quinoline-3-carboxylic acid (1pyridin-2-yl-propyl)-amide;
7-(3-methoxy-2-pentyloxy-benzoylamino)-quinoline-3-carboxylic acid (di-pyridin-2-yl-methyl)-amide;
7-(3-methoxy-2-pentyloxy-benzoylamino)-quinoline-3-carboxylic acid (phenyl-pyridin-2-yl-methyl)-amide;
7-(3-methoxy-2-pentyloxy-benzoylamino)-quinoline-3-carboxylic acid (1pyridin-2-yl-propyl)-amide;
7-(2-benzyloxy-3-methoxy-benzoylamino)-quinoline-3-carboxylic acid (di-pyridin-2-yl-methyl)-amide;
7-(2-cyclopentylethoxy-3-methoxy-benzoylamino)-quinoline-3-carboxylic acid (di-pyridin-2-yl-methyl)-amide;
7-[3-methoxy-2-(4,4,4-trifluoro-butoxy)-benzoylamino]-quinoline-3-carboxylic acid (di-pyridin-2-yl-methyl)-amide;
7-[3-methoxy-2-(3-methyl-butoxy)-benzoylamino]-quinoline-3-carboxylic acid (di-pyridin-2-yl-methyl)-amide;
7-(2-cyclobutylmethoxy-3-methoxy-benzoylamino)-quinoline-3-carboxylic acid (di-pyridin-2-yl-methyl)-amide;
7-(2-cyclopentylmethoxy-3-methoxy-benzoylamino)-quinoline-3-carboxylic acid (di-pyridin-2-yl-methyl)-amide;
2-hexyloxy-3-methoxy-benzoylamino)-quinoline-3-carboxylic acid (di-pyridin-2-yl-methyl)-amide;
7-(2-cyclohexylethoxy-3-methyl-benzoylamino)-quinoline-3-carboxylic acid (di-pyridin-2-yl-methyl)-amide;
7-(2-cyclohexylmethoxy-3-methyl-benzoylamino)-quinoline-3-carboxylic acid (di-pyridin-2-yl-methyl)-amide;

2-methyl-7-[2-(5-trifluoromethyl-pyridin-2-yl)-benzoylamino]-quinoline-3-carboxylic acid (1-pyridin-2-yl-ethyl)-amide;

2-methyl-7-{[2-(4-trifluoromethyl-phenyl)-pyridine-3-carbonyl]-amino}-quinoline-3-carboxylic acid (1pyridin-2-yl-ethyl)-amide;

2-ethyl-7-[2-(5-trifluoromethyl-pyridin-2-yl)-benzoylamino]-quinoline-3-carboxylic acid (1pyridin-2-yl-ethyl)-amide;

2-ethyl-7-{[2-(4-trifluoromethyl-phenyl)-pyridine-3-carbonyl]-amino}-quinoline-3-carboxylic acid (1pyridin-2-yl-ethyl)-amide;

7-{[6-methyl-2-(4-trifluoromethyl-phenyl)-pyridine-3-carbonyl]-amino}-quinoline-3-carboxylic acid (1pyridin-2-yl-ethyl)-amide;

7-[(6-methyl-4'-trifluoromethyl-biphenyl-2-carbonyl)-amino]-quinoline-3-carboxylic acid (1-pyridin-2-yl-ethyl)-amide;

7-[3-methyl-2-(5-trifluoromethyl-pyridin-2-yl)-benzoylamino]-quinoline-3-carboxylic acid (1pyridin-2-yl-ethyl)-amide;

7-[3,5-dimethyl-2-(5-trifluoromethyl-pyridin-2-yl)-benzoylamino]-quinoline-3-carboxylic acid (1-pyridin-2-yl-ethyl)-amide;

7-(3-chloro-2-cyclohexylmethoxy-benzoylamino)-quinoline-3-carboxylic acid (di-pyridin-2-yl-methyl)-amide, or a stereoisomer, pharmaceutically acceptable salt or prodrug thereof, or a pharmaceutically acceptable salt of the prodrug.

32. A method of inhibiting apolipoprotein B secretion, the method comprising administering to a patient in need of apolipoprotein B secretion inhibition an apolipoprotein B secretion inhibiting amount of a compound of claim 26, or a stereoisomer, pharmaceutically acceptable salt or prodrug thereof, or a pharmaceutically acceptable salt of the prodrug.

33. A method of inhibiting microsomal triglyceride transfer protein, the method comprising administering to a patient in need of microsomal triglyceride transfer protein inhibition a microsomal triglyceride transfer protein inhibiting amount of a compound of claim 26, or a stereoisomer, pharmaceutically acceptable salt or prodrug thereof, or a pharmaceutically acceptable salt of the prodrug.

34. A pharmaceutical composition comprising a compound of claim 26, or a stereoisomer, pharmaceutically acceptable salt or prodrug thereof, or a pharmaceutically acceptable salt of the prodrug and a pharmaceutically acceptable carrier.

35. The compound:

7-[(4'-trifluoromethyl-biphenyl-2-carbonyl)-amino]-quinoline-3-carboxylic acid (pentylcarbamoyl-phenyl-methyl)-amide;

7-[(4'-trifluoromethyl-biphenyl-2-carbonyl)-amino]-quinoline-3-carboxylic acid (diethylcarbamoyl-phenyl-methyl)-amide;

7-[(4'-trifluoromethyl-biphenyl-2-carbonyl)-amino]-quinoline-3-carboxylic acid-S-(pentylcarbamoyl-phenyl-methyl)-amide;

7-[(4'-trifluoromethyl-biphenyl-2-carbonyl)-amino]-quinoline-3-carboxylic acid-S-(diethylcarbamoyl-phenyl-methyl)-amide;

7-[(4'-trifluoromethyl-biphenyl-2-carbonyl)-amino]-quinoline-3-carboxylic acid-R-(pentylcarbamoyl-phenyl-methyl)-amide;

7-[(4'-trifluoromethyl-biphenyl-2-carbonyl)-amino]-quinoline-3-carboxylic acid-R-(diethylcarbamoyl-phenyl-methyl)-amide, or a pharmaceutically acceptable salt or prodrug thereof, or a pharmaceutically acceptable salt of the prodrug.

* * * * *